United States Patent
Brown et al.

(10) Patent No.: US 7,241,764 B2
(45) Date of Patent: Jul. 10, 2007

(54) 4(PHENYL-PIPERAZINYL-METHYL) BENZAMIDE DERIVATIVES AND THEIR USE FOR THE TREATMENT OF PAIN OR GASTROINTESTINAL DISORDERS

(75) Inventors: William Brown, Blainville (CA); Andrew Griffin, Montreal (CA)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/533,764

(22) PCT Filed: Nov. 5, 2003

(86) PCT No.: PCT/SE03/01706

§ 371 (c)(1),
(2), (4) Date: May 4, 2005

(87) PCT Pub. No.: WO2004/041801

PCT Pub. Date: May 21, 2004

(65) Prior Publication Data

US 2006/0142296 A1 Jun. 29, 2006

(30) Foreign Application Priority Data

Nov. 7, 2002 (SE) .................................. 0203302

(51) Int. Cl.
C07D 241/04 (2006.01)
A61K 31/495 (2006.01)
A61P 25/04 (2006.01)

(52) U.S. Cl. ............................ 514/252.12; 514/252.13; 514/253.01; 514/253.09; 514/253.1; 514/253.11; 514/255.04; 544/396; 544/360; 544/366; 544/367; 544/370; 544/372; 544/374

(58) Field of Classification Search ................ 544/396; 514/255.04
See application file for complete search history.

(56) References Cited

U.S. PATENT DOCUMENTS

| | | | |
|---|---|---|---|
| 3,940,386 A | 2/1976 | Szabo et al. | |
| 5,574,159 A | 11/1996 | Chang et al. | |
| 5,681,830 A | 10/1997 | Chang et al. | |
| 5,807,858 A | 9/1998 | Chang et al. | |
| 5,854,249 A | 12/1998 | Chang et al. | |
| 6,130,222 A | 10/2000 | Roberts et al. | |
| 6,680,318 B2 | 1/2004 | Brown et al. | |
| 6,680,321 B1 | 1/2004 | Roberts et al. | |
| 6,696,447 B2 | 2/2004 | Brown et al. | |
| 6,784,181 B2 | 8/2004 | Brown et al. | |

FOREIGN PATENT DOCUMENTS

| | | |
|---|---|---|
| DE | 2431178 | 1/1975 |
| DE | 2900810 | 7/1980 |
| EP | 0133323 | 2/1985 |
| EP | 0166302 | 1/1986 |
| EP | 0283310 | 9/1988 |
| EP | 0289227 | 11/1988 |
| EP | 0624584 | 8/1998 |
| FR | 2696744 | 4/1994 |
| GB | 2076403 | 12/1981 |
| GB | 2210366 | 6/1989 |
| JP | 7-138230 | 5/1995 |
| WO | WO 86/04584 | 8/1986 |
| WO | WO 91/07967 | 6/1991 |
| WO | WO 93/15062 | * 2/1992 |
| WO | WO 92/04338 | 3/1992 |
| WO | WO 93/15062 | 8/1993 |
| WO | WO 95/04051 | 2/1995 |
| WO | WO 97/23466 | 7/1997 |
| WO | WO 98/28270 | 7/1998 |
| WO | WO 98/28275 | 7/1998 |

(Continued)

OTHER PUBLICATIONS

Saitoch, A.; Potential Anxiolytic and Antidepressant-Like Activities of SNC80, a Selective delta-Opioid Agonist, in Behavioral Models in Rodents; J. Pharmacol. Sci.; 2004; 95; 374-380.*
Filliol, D.; Nature Genetics; 2000; 25; 195-200.*
U.S. Appl. No. 10/533,654, filed May 4, 2005, Brown et al.
U.S. Appl. No. 10/533,744, filed May 4, 2005, Brown et al.
U.S. Appl. No. 10/714,447, filed Nov. 17, 2003, Roberts et al.
U.S. Appl. No. 10/477,642, filed Nov. 13, 2003, Brown et al.

(Continued)

*Primary Examiner*—James O. Wilson
*Assistant Examiner*—Susanna Moore
(74) *Attorney, Agent, or Firm*—Jacqueline M. Cohen

(57) ABSTRACT

Compounds of general formula:[Chemical formula should be inserted here. Please see paper copy] wherein $R_1$, $R_2$, and $R_3$ are as defined in the specification, as well as salts, enantiomers thereof and pharmaceutical compositions including the compounds are prepared. They are useful in therapy, in particular in the management of pain

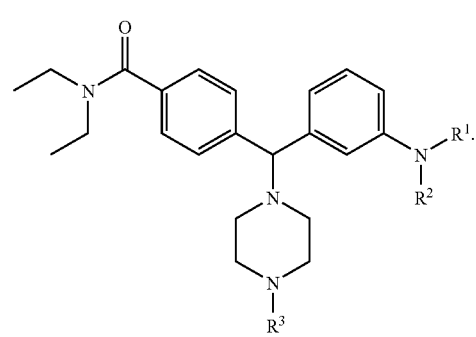

(I)

17 Claims, No Drawings

FOREIGN PATENT DOCUMENTS

| | | |
|---|---|---|
| WO | WO 99/33806 | 7/1999 |
| WO | WO 01/45637 | 6/2001 |
| WO | WO 01/46174 | 6/2001 |
| WO | WO 01/74805 | 10/2001 |
| WO | WO 02/094794 | 11/2002 |
| WO | WO 03/029215 | 4/2003 |
| WO | WO 2004/041800 | 5/2004 |
| WO | WO 2004/041801 | 5/2004 |
| WO | WO 2005/066148 | 7/2005 |

OTHER PUBLICATIONS

Bilsky et al., "SNC 80, A Selective, Nonpeptidic and Systemically Active Opioid Delta Agonist," J. Pharmacol. Experi. Ther. 273:359-366 (1995).

Takemori et al., "Selective Natrexone-Drived Opioid Receptor Antagonists," Annu. Rev. Pharmacol. Toxicol. 32:239-269 (1992).

Bilsky et al., "Characterization of Enantiomers of (+) BW373U86 and Related Compounds: Highly Selective Non-Peptidic Delta Opioid Agonists," Reg. Peptides 54:25-26 (1994).

Calderon et al., "Probes for Narcotic Receptor Mediated Phenomena. 19. Synthesis of . . . Opioid Receptor Agonist," J. Med. Chem. 37:2125-2128 (1994).

Calderon et al., "Probes for Narcotic Receptor Mediated Phenomena. 23. Synthesis . . . Opioid Receptor Ligands," J. Med. Chem. 40:695-704 (1997).

Chang et al., "A Novel, Potent and Selective Nonpeptidic Delta Opioid Receptor Agonist BW373U86," J. Pharmacol. Exper. Therap. 267:852-857 (1993).

Katrizky et al., "Benzotriazole-Mediated Arylalkylation and Heteroarylalkylation," Chem. Soc. Rev. 23:363-373 (1994).

Kingsbury et al., "Synthesis of Structural Analogs of Leukotriene B and their Receptor Binding Activity," J. Med. Chem. 36:3308-3320 (1993).

Lopez et al., "Exploring the Structure-Activity Relationships . . . Opioid Receptor Nonpeptide Agonist Ligand," J. Med. Chem. 42:5359-5368 (1999).

Plobeck et al., "New Diarylmethylpiperazines as Potent and Selective Nonpeptidic Opioid Receptor Agonists with Increased In Vitro Metabolic Stability," J. Med. Chem. 43:3878-3894 (2000).

Suggs et al., "Facile Synthesis fo 8-Substituted Quinolines," J. Org. Chem., 45:1514-1515 (1980).

Zhang et al., "Probes for Narcotic Receptor Mediated Phenomena. 26. Synthesis . . . Opioid Receptor Ligands," J. Med. Chem. 42:5455-5463 (1999).

English Abstract for Reference B16 on PTO/SB/08A, p. 4.

English Abstract for Reference B17 on PTO/SB/08A, p. 4.

English Abstract for Reference B18 on PTO/SB/08A, p. 4.

English Abstract for Reference B19 on PTO/SB/08A, p. 4.

Burkey et al., "The Efficacy of Delta-Opioid Receptor-Selective Drugs," Medline Abstract for Life Sci. 62:1531-1536 (1998).

Nagase et al., "The Pharmacological Profile of Delta Opioid Receptor Ligands, (+) and (−) TAN-67 on Pain Modulation," Medline Abstract for Life Sci. 68:2227-2231 (2001).

Green, "Protective Groups in Organic Synthesis," pp. 267-268 and 331 (1981).

Abstract for HU 217619. A corresponding English language PCT application is cited as Reference B1 listed on PTO/SB/08A, p. 1.

Abstract for HU 215487. A corresponding English language PCT application is cited as reference B2 on PTO/SB/08A, p. 1.

Nortey et al., "Piperazinyl Benzamidines: Synthesis and Affinity for the Delta Opioid Receptor," Bioorganic & Medicinal Chemistry Letters, vol. 11, pp. 1741-1743 (2001).

Snyder et al., "Historical Review: Opioid Receptors," Trends in Pharmacological Sciences, vol. 24, pp. 198-205 (2003).

Filliol, D. et al., "Mice deficient for δ- and μ-opioid receptors exhibit opposing alterations of emotional responses," Nature Genetics, vol. 25, pp. 195-200, Jun. 2000.

* cited by examiner

4(PHENYL-PIPERAZINYL-METHYL) BENZAMIDE DERIVATIVES AND THEIR USE FOR THE TREATMENT OF PAIN OR GASTROINTESTINAL DISORDERS

CROSS-REFERENCE TO RELATED APPLICATIONS

This application is a US National Stage under 35 U.S.C § 371 of International Application No. PCT/SE2003/001706, filed on 5 Nov. 2003, which claims priority under 35 U.S.C. § 119(a)-(d) to Swedish Application No. 0203302-5 filed on 7 Nov. 2002.

BACKGROUND OF THE INVENTION

1. Field of the Invention

The present invention is directed to novel compounds, to a process for their preparation, their use and pharmaceutical compositions comprising the novel compounds. The novel compounds are useful in therapy, and in particular for the treatment of pain, anxiety and functional gastrointestinal disorders.

2. Discussion of Relevant Art

The δ receptor has been identified as having a role in many bodily functions such as circulatory and pain systems. Ligands for the δ receptor may therefore find potential use as analgesics, and/or as antihypertensive agents. Ligands for the δ receptor have also been shown to possess immuno-modulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., Journal of Pharmacology and Experimental Therapeutics, 273(1), pp. 359-366 (1995)).

Many δ agonist compounds that have been identified in the prior art have many disadvantages in that they suffer from poor pharmacokinetics and are not analgesic when administered by systemic routes. Also, it has been documented that many of these δ agonist compounds show significant convulsive effects when administered systemically.

U.S. Pat. No. 6,130,222 to Roberts et al. describes some δ-agonists.

However, there is still a need for improved δ-agonists.

DETAILED DESCRIPTION OF THE INVENTION

DEFINITIONS

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures.

The term "$C_{m-n}$" or "$C_{m-n}$ group" used alone or as a prefix, refers to any group having m to n carbon atoms.

The term "hydrocarbon" used alone or as a suffix or prefix, refers to any structure comprising only carbon and hydrogen atoms up to 14 carbon atom's.

The term "hydrocarbon radical" or "hydrocarbyl" used alone or as a suffix or prefix, refers to any structure as a result of removing one or more hydrogens from a hydrocarbon.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms.

The term "arylene" used alone or as suffix or prefix, refers to a divalent hydrocarbon radical having one or more polyunsaturated carbon rings having aromatic character, (e.g., 4n+2 delocalized electrons) and-comprising 5 up to about 14 carbon atoms, which serves to link two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-6}$ hydrocarbon groups, or one or more chemical groups containing one or more heteroatoms selected from N, O, S, F, Cl, Br, I, and P. Exemplary chemical groups containing one or more heteroatoms include —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, oxo (=O), imino (=NR), thio (=S), and oximino (=N—OR), wherein each "R" is a $C_{1-6}$ hydrocarbyl. For example, substituted phenyl may refer to nitrophenyl, methoxyphenyl, chlorophenyl, aminophenyl, etc., wherein the nitro, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "amine" or "amino" used alone or as a suffix or prefix, refers to radicals of the general formula —NRR', wherein R and R' are independently selected from hydrogen or a hydrocarbon radical.

Halogen includes fluorine, chlorine, bromine and iodine.

"Halogenated," used as a prefix of a group, means one or more hydrogens on the group is replaced with one or more halogens.

"RT" or "rt" means room temperature.

DESCRIPTION OF THE EMBODIMENTS

In one aspect, the invention provides a compound of formula I, enantiomers thereof, diastereomers thereof and pharmaceutically acceptable salts thereof:

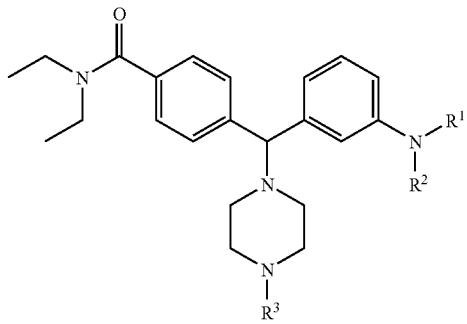

I wherein $R^1$ is selected from $C_{3-6}$alkyl, $C_{6-10}$aryl, $C_{2-9}$heteroaryl, $C_{6-10}$aryl-$C_{1-4}$alkyl, $C_{2-9}$-heteroaryl-$C_{1-4}$alkyl, $C_{3-10}$cycloalkyl, $C_{3-10}$cycloalkyl-$C_{1-4}$alkyl, $R^8$—C(=O)—, $R^8$—S(=O)$_2$—, $R^8$—S(=O)—, $R^8$—NHC(=O)—, $R^8$—C(=S)— and $R^8$—NH—C(=S)—, wherein $R^8$ is selected from $C_{3-6}$alkyl, $C_{6-10}$aryl, $C_{2-9}$-heteroaryl, $C_{6-10}$aryl-$C_{1-4}$alkyl, $C_{2-9}$heteroaryl-$C_{1-4}$alkyl, $C_{3-10}$cycloalkyl, and $C_{3-10}$cycloalkyl-$C_{1-4}$alkyl, wherein said $C_{3-6}$alkyl, $C_{6-10}$aryl, $C_{2-9}$heteroaryl, $C_{6-10}$aryl-$C_{1-4}$alkyl, $C_{2-9}$heteroaryl-$C_{1-4}$alkyl, $C_{3-10}$cycloalkyl, and $C_{3-10}$cycloalkyl-$C_{1-4}$alkyl used in defining $R^1$ and $R^8$ are optionally substituted with one or more groups selected from —R, —NO$_2$, —OR, —Cl, —Br, —I, —F, —CF$_3$, —C(=O)R, —C(=O)OH, —NH$_2$, —SH, —NHR, —NR$_2$, —SR, —SO$_3$H, —SO$_2$R, —S(=O)R, —CN, —OH, —C(=O)OR, —C(=O)NR$_2$, —NRC(=O)R, and —NRC(=O)—OR, wherein R is, independently, selected from —H, $C_{1-6}$alkyl and phenyl;

$R^2$ is selected from —H and $C_{1-6}$alkyl optionally substituted with one or more groups selected from —CF$_3$, —OH, $C_{1-3}$alkoxy, and halogen; and $R^3$ is selected from —H, $C_{1-6}$alkyl-O—C(=O)—, $C_{1-6}$alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —NO$_2$, —CF$_3$, $C_{1-6}$alkoxy and halogen.

In one embodiment, the compounds of the present invention are represented by formula I, wherein $R^1$ is selected from $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, $C_{3-10}$cycloalkyl-$C_{1-4}$alkyl, wherein said $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, $C_{3-10}$cycloalkyl-$C_{1-4}$alkyl are optionally substituted with one or more groups selected from $C_{1-4}$alkyl, —CF$_3$, —OH, $C_{1-3}$alkoxy, phenoxy, and halogen;

$R^2$ is selected from —H and $C_{1-3}$alkyl; and $R^3$ is selected from —H and $C_{1-6}$alkyl-O—C(=O)—.

In another embodiment, the compounds of the present invention are represented by formula I, wherein $R^1$ is $R^9$—CH$_2$—, wherein $R^9$ is selected from phenyl, pyridyl, thienyl, furyl, imidazolyl, triazolyl, pyrrolyl, thiazolyl, N-oxido-pyridyl, benzyl, pyridylmethyl, thienylmethyl, furylmethyl, imidazolylmethyl, triazolylmethyl, pyrrolylmethyl, thiazolylmethyl and N-oxido-pyridylmethyl, optionally substituted with one or more groups selected from $C_{1-4}$alkyl, —CF$_3$, —OH, $C_{1-3}$alkoxy, phenoxy and halogen; and $R^2$ and $R^3$ are hydrogen.

In another embodiment, the compounds of the present invention are represented by formula I, wherein $R^1$ is $R^9$—CH$_2$—, wherein $R^9$ is selected from benzyl, phenyl, pyridyl, thienyl, furyl, imidazolyl, pyrrolyl and thiazolyl, optionally substituted with one or more groups selected from $C_{1-4}$alkyl, —CF$_3$, —OH, $C_{1-3}$alkoxy, phenoxy, and halogen; and $R^2$ and $R^3$ are hydrogen.

In another embodiment, the compounds of the present invention are represented by formula I wherein $R^1$ is $R^9$—CH$_2$—, wherein $R^9$ is selected from benzyl, phenyl, pyridyl, thienyl, furyl, imidazolyl, pyrrolyl and thiazolyl; and $R^2$ and $R^3$ are hydrogen.

In another embodiment, the compounds of the present invention are represented by formula I, wherein $R^1$ is selected from $C_{3-6}$alkyl, $C_{3-10}$cycloalkyl, and $C_{3-10}$cycloalkyl-$C_{1-4}$alkyl, wherein said $C_{3-6}$alkyl, $C_{3-10}$cycloalkyl, and $C_{3-10}$cycloalkyl-$C_{1-4}$alkyl are optionally substituted with one or more groups selected from $C_{1-4}$alkyl, —CF$_3$, —OH, $C_{1-3}$alkoxy, phenoxy, and halogen;

$R^2$ is —H or $C_{1-3}$alkyl; and $R^3$ is —H, $C_{1-6}$alkyl, $C_{3-6}$cycloalkyl, and $C_{3-6}$cycloalkyl-$C_{1-4}$alkyl, wherein said $C_{1-6}$alkyl, $C_{3-6}$cycloalkyl, $C_{3-6}$cycloalkyl-$C_{1-4}$alkyl are optionally substituted with one or more groups selected from $C_{1-4}$alkyl, —CF$_3$, —OH, $C_{1-3}$alkoxy, phenoxy, and halogen.

In another embodiment, the compounds of the present invention are represented by formula I, wherein $R^1$ is selected from 1-propyl, 2-propyl, 1-butyl, 2-butyl, t-butyl, 2-methyl-1-propyl, cyclopentyl, cyclohexyl, cycloheptyl, cyclooctyl, and cyclononyl;

$R^2$ is selected from —H, methyl, ethyl, 1-propyl and 2-propyl; and $R^3$ is selected from —H, methyl, ethyl, alkyl, 3,3-dimethyl-alkyl, cyclopropylmethyl, 2-methoxy-ethyl, and 3-methoxy-1-propyl.

In another embodiment, the compounds of the present invention are represented by formula I, wherein $R^1$ is selected from $R^8$—C(=O)—, $R^8$—S(=O)$_2$—, $R^8$—S(=O)—, $R^8$—NHC(=O)—, $R^8$—C(=S)— and $R^8$—NH—C(=S)—, wherein $R^8$ is selected from $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl; wherein said $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl are optionally substituted with $C_{1-4}$alkyl, —$CF_3$, —OH, $C_{1-3}$alkoxy, phenoxy, and halogen;

$R^2$ is —H; and $R^3$ is selected from —H and $C_{1-6}$alkyl-O—C(=O)—.

In a further embodiment, the compounds of the present invention are represented by formula I, wherein $R^1$ is selected from $R^8$—C(=O)—, $R^8$—S(=O)$_2$—, $R^8$—S(=O)—, $R^8$—NHC(=O)—, $R^8$—C(=S)— and $R^8$—NH—C(=S)—, wherein $R^8$ is selected from phenyl, benzyl, phenethyl and cyclohexyl, wherein said phenyl, benzyl, phenethyl and cyclohexyl are optionally substituted with one or more groups selected from methyl, methoxy and halogen;

$R^2$ is —H; and $R^3$ is selected from —H and $C_{1-6}$alkyl-O—C(=O)—.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastrointestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction; spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be contrued accordingly. The term "therapy" within the context of the present invention further encompasses to administer an effective amount of a compound of the present invention, to mitigate either a preexisting disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: chronic pain, neuropathic pain, acute pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: chronic pain, neuropathic pain, acute pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

In a further aspect, the present invention provides a method of preparing a compound of formula I.

In one embodiment, the invention provides a process for preparing a compound of formula II, comprising:

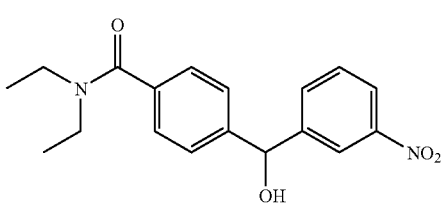

a) reacting a compound of formula III:

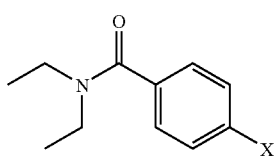

with a compound of formula IV

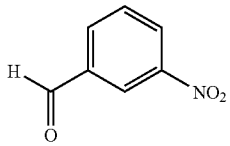

IV

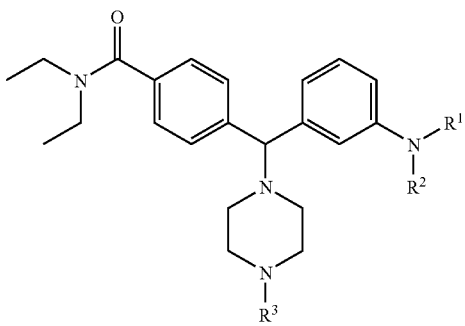

I in the presence of a base having a pKa of more than 15
wherein
X is a halogen.

In another embodiment, the invention provides a process for preparing a compound of formula VI:

VI

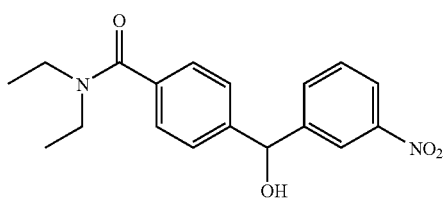

comprising: reacting a compound of formula VIII,

VIII

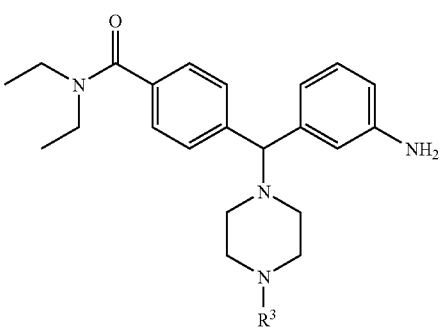

with $R^9$—CHO in the presence of a reducing agent to form the compound of formula I:

wherein $R^1$ is $R^9$—$CH_2$—, wherein $R^9$ is selected from phenyl, pyridyl, thienyl, furyl, imidazolyl, triazolyl, pyrrolyl, thiazolyl, N-oxido-pyridyl, benzyl, pyridylmethyl, thienylmethyl, furylmethyl, imidazolylmethyl, triazolylmethyl, pyrrolylmethyl, thiazolylmethyl and N-oxido-pyridylmethyl, optionally substituted with one or more groups selected from $C_{1-4}$alkyl, —$CF_3$, —OH, $C_{1-3}$alkoxy, phenoxy and halogen;

$R^2$ is —H; and $R^3$ is selected from $C_{1-6}$alkyl-O—C(=O)—, $C_{1-6}$alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —$NO_2$, —$CF_3$, $C_{1-6}$alkoxy and halogen.

In another embodiment, the invention provides a process for preparing a compound of formula IX,

IX

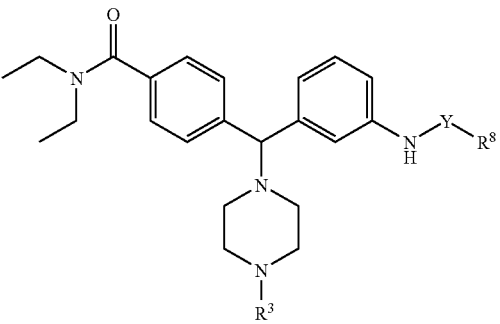

comprising: reacting a compound of formula VIII, comprising: reacting a compound of formula II

II

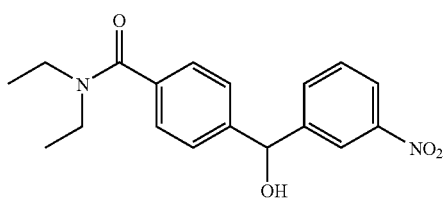

with a compound of formula VII

VII

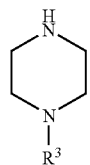

in the presence of $SOX_2$ to form the compound of formula VI, wherein $R^3$ is selected from —H, $C_{1-6}$alkyl-O—C(=O)—, $C_{1-6}$alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —$NO_2$, —$CF_3$, $C_{1-6}$alkoxy and halogen; and X is halogen.

In another embodiment, the invention provides a process for preparing a compound of formula I,

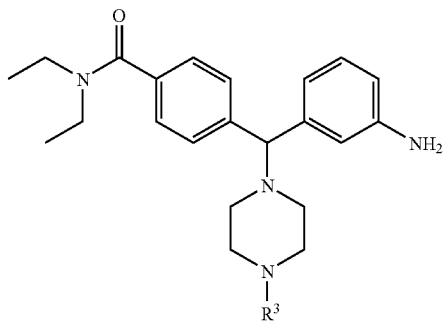

with R⁸—Y—X or R⁸—Y—O—Y—R⁸ to form the compound of formula IX:

wherein
X is halogen;
Y is selected from —C(=O)— and —S(=O)₂—;
R⁸ is selected from $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl; wherein said $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl are optionally substituted with $C_{1-4}$alkyl, —CF₃, —OH, $C_{1-3}$alkoxy, phenoxy, and halogen; and
R³ is selected from $C_{1-6}$alkyl-O—C(=O)—, $C_{1-6}$-alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —NO₂, —CF₃, $C_{1-6}$alkoxy and halogen.

In another embodiment, the invention provides a process for preparing a compound of formula IX,

IX

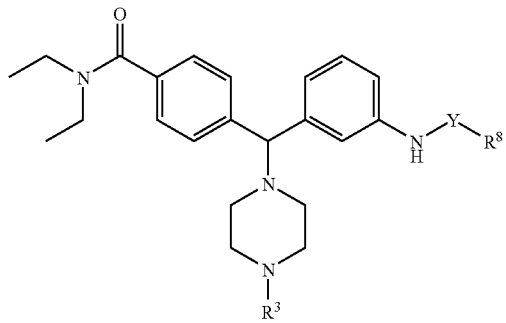

comprising: reacting a compound of formula VIII,

VIII

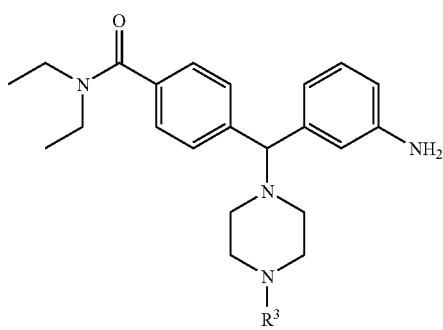

with R⁸-Z to form the compound of formula IX:

wherein
Z is selected from —NCO and —NCS;
Y is selected from —C(=O)NH— and —C(=S)NH—;
R⁸ is selected from $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl; wherein said $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl are optionally substituted with $C_{1-4}$alkyl, —CF₃, —OH, $C_{1-3}$alkoxy, phenoxy, and halogen; and
R³ is selected from $C_{1-6}$alkyl-O—C(=O)—, $C_{1-6}$-alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —NO₂, —CF₃, $C_{1-6}$alkoxy and halogen.

Particularly, the compounds of the present invention can be prepared according to the synthetic routes as exemplified in Schemes 1-10.

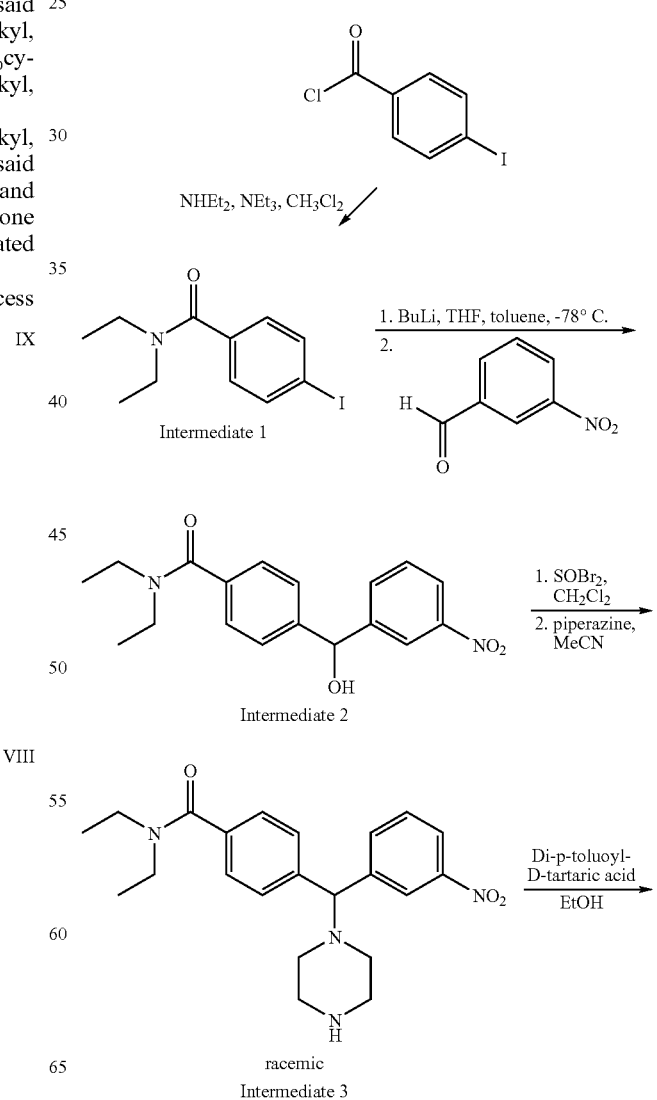

Scheme 1

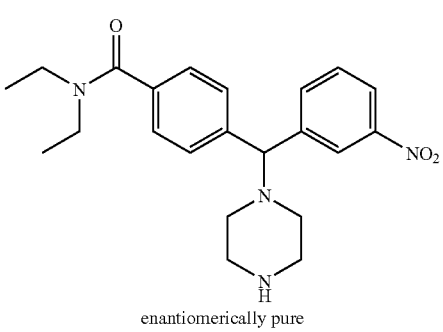

enantiomerically pure
Intermediate 4a: (S) enantiomer
Intermediate 4b: (R) enantiomer Scheme 2

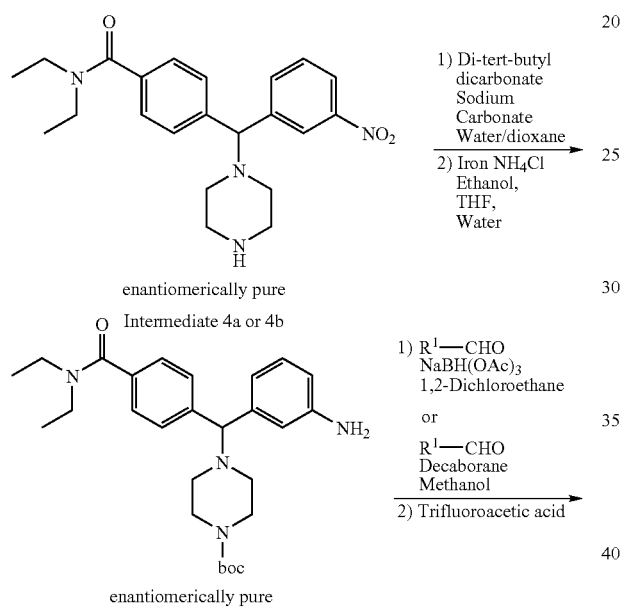

(S) enantiomers:
Compound 1: $R^9$ = 2-thiazolyl, $R^{16}$ = H;
Compound 3: $R^9$ = phenyl, $R^{16}$ = H;
Compound 5: $R^9$ = 2-thienyl, $R^{16}$ = H;
Compound 6: $R^9$ = 2-furyl, $R^{16}$ = H;
Compound 10: $R^9$ = 3-thienyl, $R^{16}$ = H;
Compound 16: $R^9$ = cyclohexyl, $R^{16}$ = H;
Compound 48: $R^9$ = ethyl, $R^{16}$ = H;
Compound 49: $R^9$ = ethyl, $R^{16}$ = propyl;
Compound 52: $R^9$ = 4-(3-pyridinyl)pheyl, $R^{16}$ = H;
Compound 53: $R^9$ = 4'(1H-imidazol-1-yl)phenyl, $R^{16}$ = H;
Compound 54: $R^9$ = 2-quinolinyl, $R^{16}$ = H;

(R) enantiomers:
Compound 2: $R^9$ = 3-thiazolyl, $R^{16}$ = H;
Compound 4: $R^9$ = 2-thienyl, $R^{16}$ = H;
Compound 7: $R^9$ = phenyl, $R^{16}$ = H;
Compound 8: $R^9$ = 2-furyl, $R^{16}$ = H;
Compound 9: $R^9$ = 3-thienyl, $R^{16}$ = H;
Compound 11: $R^9$ = 3-furyl, $R^{16}$ = H;
Compound 12: $R^9$ = benzyl, $R^{16}$ = H;
Compound 13: $R^9$ = cyclohexyl, $R^{16}$ = H;
Compound 14: $R^9$ = 4-trifluoromethyl phenyl, $R^{16}$ = H;
Compound 15: $R^9$ = cyclopentyl, $R^{16}$ = H;
Compound 17: $R^9$ = cyclohex-1-enyl, $R^{16}$ = H;
Compound 50: $R^9$ = ethyl, $R^{16}$ = H;
Compound 51: $R^9$ = ethyl, $R^{16}$ = propyl;
Compound 55: $R^9$ = 1,1-diphenylmethyl, $R^{16}$ = H;
Compound 56: $R^9$ = 4-(1,1-dimethylethyl)phenyl, $R^{16}$ = H
Compound 57: $R^9$ = 4-phenoxyphenyl, $R^{16}$ = H;

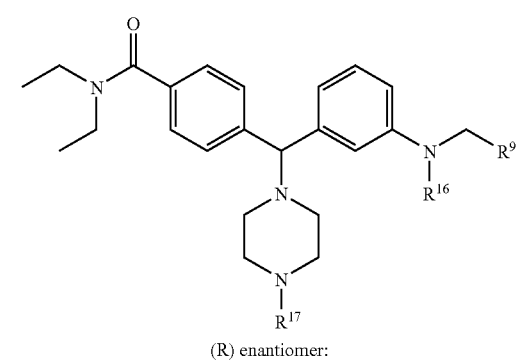

(R) enantiomer:
Compound 58: $R^9$ = ethyl, $R^{16}$ = H, $R^{17}$ = allyl;

Scheme 3

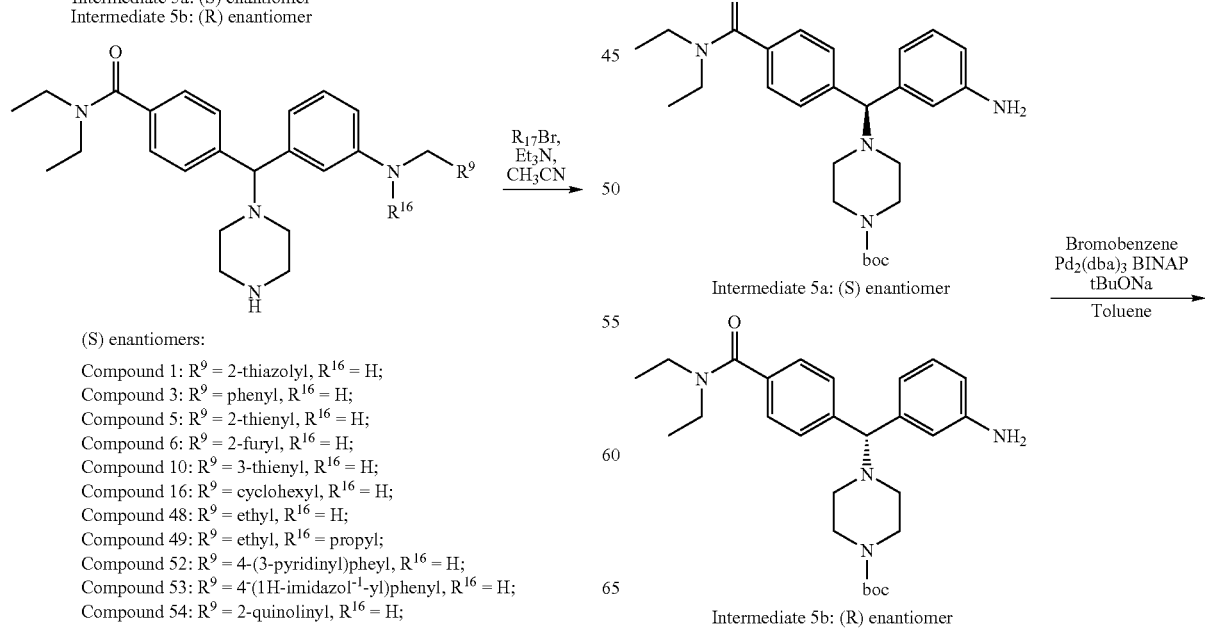

-continued

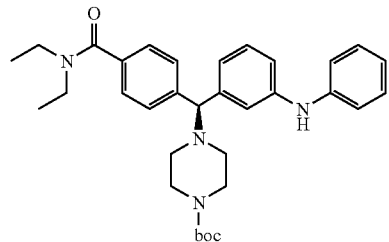

Intermediate 6a: (S) enantiomer

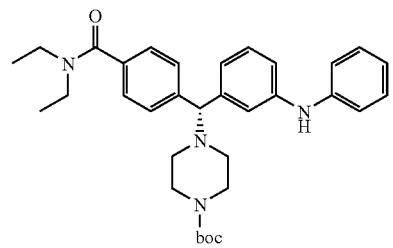

Intermediate 6b: (R) enantiomer

1) Aldehyde
Decaborane
Methanol
2) Trifluoroacetic acid
Dichloromethane

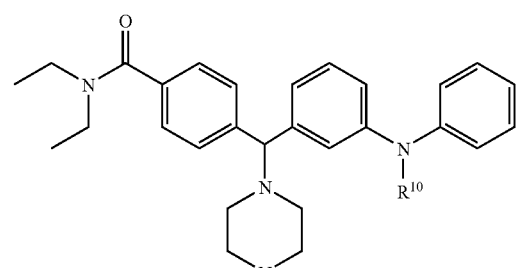

(S) enantiomers:
Compound 18: $R^{10}$ = methyl;
Compound 19: $R^{10}$ = ethyl.
(R) enantiomers:
Compound 20: $R^{10}$ = methyl;
Compound 21: $R^{10}$ = ethyl.

-continued

(S) enantiomers:
Compound 27: $R^{11}$ = cyclohexl;
Compound 63: $R^{11}$ = cycloheptyl;
Compound 64: $R^{11}$ = cyclooctyl.
(R) enantiomers:
Compound 22: $R^{11}$ = cyclohexl;
Compound 23: $R^{11}$ = cyclopentyl;
Compound 24: $R^{11}$ = cycloheptyl;
Compound 25: $R^{11}$ = cyclooctyl;
Compound 26: $R^{11}$ = cyclononyl.

$R^{20}CH_2Br$, $Et_3N$, $CH_3CN$
or
$R^{20}CHO$; $NaBH(OAc)_3$; AcOH; DCE

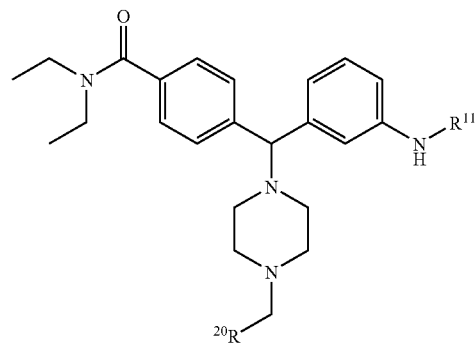

(S) enantiomers ($R^{11}$ = cyclohexyl):
Compound 72: $R^{20}$ = cyclopropyl;
Compound 73: $R^{20}$ = ethyl;
Compound 74: $R^{20}$ = methyl;
Compound 75: $R^{20}$ = vinyl.

Scheme 4

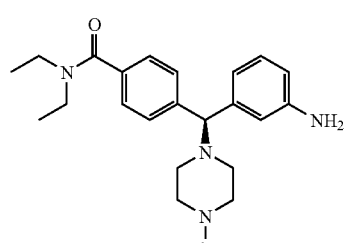

Intermediate 5a: (S) enantiomer

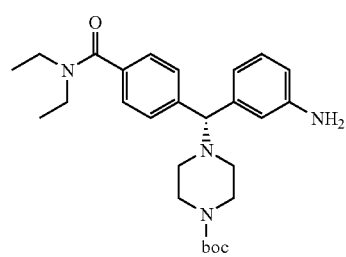

Intermediate 5b: (R) enantiomer

1) Ketone
NaBH(OAc)$_3$
1,2-Dichloroethane
or
Ketone
Decaborane
Methanol
2) Trifluoroacetic acid
Dichloromethane Scheme 5

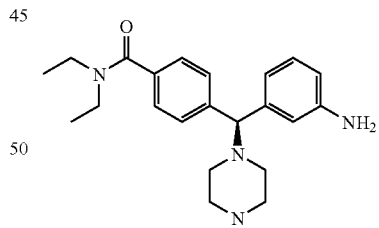

Intermediate 5a: (S) enantiomer

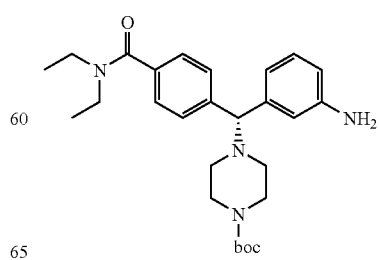

Intermediate 5b: (R) enantiomer

1) BrR$^{12}$
Pd$_2$(dba)$_3$ BINAP
tBuONa
Toluene
2) Trifluoroacetic acid
Dichloromethane -continued

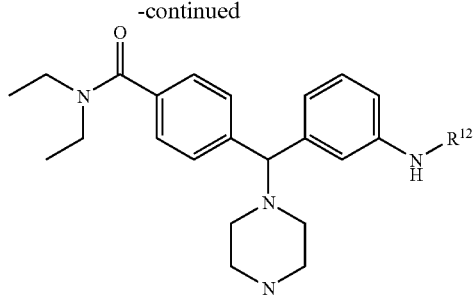

(S) enantiomers:
Compound 29: $R^{12}$ = 4-methyl phenyl;
Compound 31: $R^{12}$ = 3-chloro phenyl;
Compound 33: $R^{12}$ = 2-fluoro phenyl.

(R) enantiomers:
Compound 28: $R^{12}$ = 4-methyl phenyl;
Compound 30: $R^{12}$ = 3-chloro phenyl;
Compound 32: $R^{12}$ = 2-fluoro phenyl.

Scheme 6

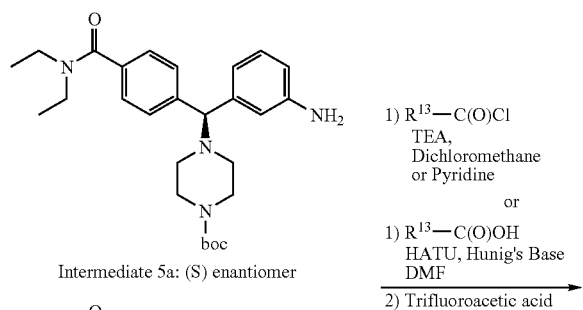

Intermediate 5a: (S) enantiomer

1) $R^{13}$—C(O)Cl
    TEA,
    Dichloromethane
    or Pyridine
    or
1) $R^{13}$—C(O)OH
    HATU, Hunig's Base
    DMF
2) Trifluoroacetic acid

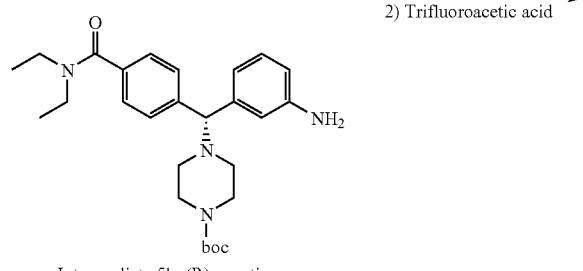

Intermediate 5b: (R) enantiomer

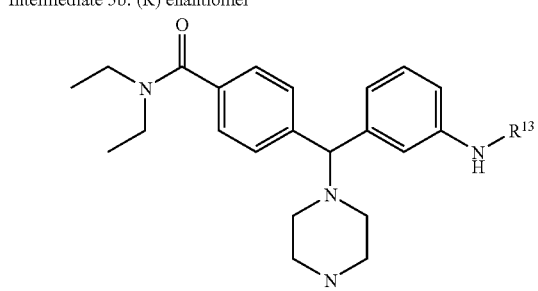

(S) enantiomers:
Compound 36: $R^{13}$ = phenyl;
Compound 37: $R^{13}$ = benzyl;
Compound 65: $R^{13}$ = phenethyl;
Compound 76: $R^{13}$ = cyclohexyl;
Compound 77: $R^{13}$ = methylcyclohexyl.

(R) enantiomers:
Compound 34: $R^{13}$ = phenyl;
Compound 35: $R^{13}$ = benzyl;
Compound 38: $R^{13}$ = alfa,alfa-methylbenzyl;
Compound 39: $R^{13}$ = 3-fluorobenzyl;
Compound 40: $R^{13}$ = methylcyclohexyl;
Compound 41: $R^{13}$ = phenethyl;
Compound 42: $R^{13}$ = cyclohexyl.

Scheme 7

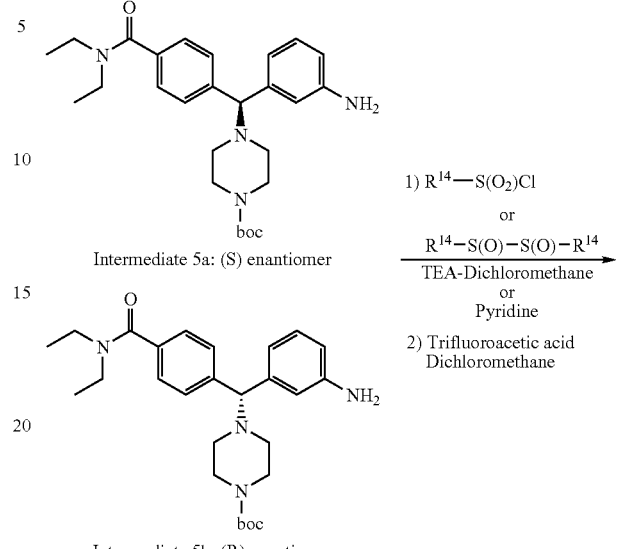

Intermediate 5a: (S) enantiomer

Intermediate 5b: (R) enantiomer

1) $R^{14}$—S($O_2$)Cl
    or
    $R^{14}$—S(O)—S(O)—$R^{14}$
    TEA-Dichloromethane
    or
    Pyridine
2) Trifluoroacetic acid
    Dichloromethane

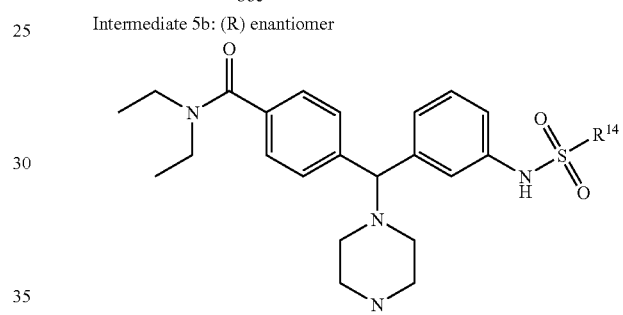

(S) enantiomers:
Compound 45: $R^{14}$ = phenyl;

(R) enantiomers:
Compound 43: $R^{14}$ = phenyl;
Compound 44: $R^{14}$ = benzyl.

Scheme 8

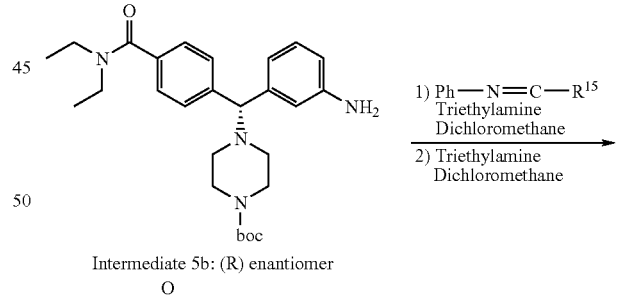

Intermediate 5b: (R) enantiomer

1) Ph—N=C—$R^{15}$
    Triethylamine
    Dichloromethane
2) Triethylamine
    Dichloromethane

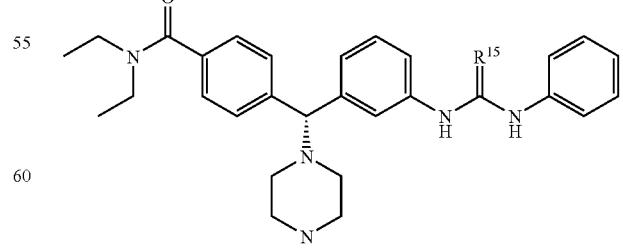

(R) enantiomers:
Compound 46: $R^{15}$ = oxygen;
Compound 47: $R^{15}$ = sulfur.

Scheme 9

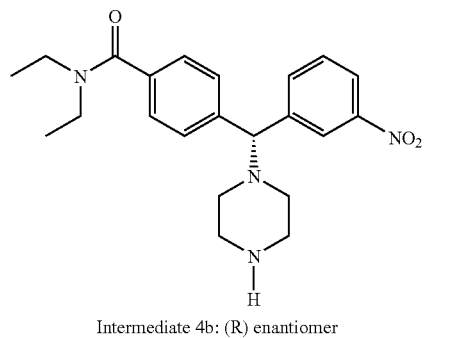

Intermediate 4b: (R) enantiomer

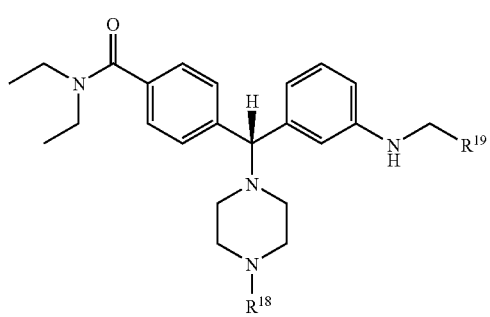

(R) enantiomers:
Compound 59: R[18] = (CH$_2$)$_2$OCH$_3$;
Compound 60: R[18] = (CH$_2$)$_3$OCH$_3$;
Compound 66: R[18] = CH$_2$CHCH$_2$;
Compound 67: R[18] = CH$_2$CHCMe$_2$;
Compound 68: R[18] = CH$_2$cyclopropyl (R) enantiomers:
Compound 61: R[18] = (CH$_2$)$_2$OCH$_3$, R[19] = ethyl;
Compound 62: R[18] = (CH$_2$)$_3$OCH$_3$; R[19] = ethyl;
Compound 69: R[18] = CH$_2$CHCH$_2$; R[19] = 2-thiophene
Compound 70: R[18] = CH$_2$CHCMe$_2$; R[19] = 2-thiophene
Compound 71: R[18] = CH$_2$cyclopropyl, R[19] = 2-thiophene Scheme 10

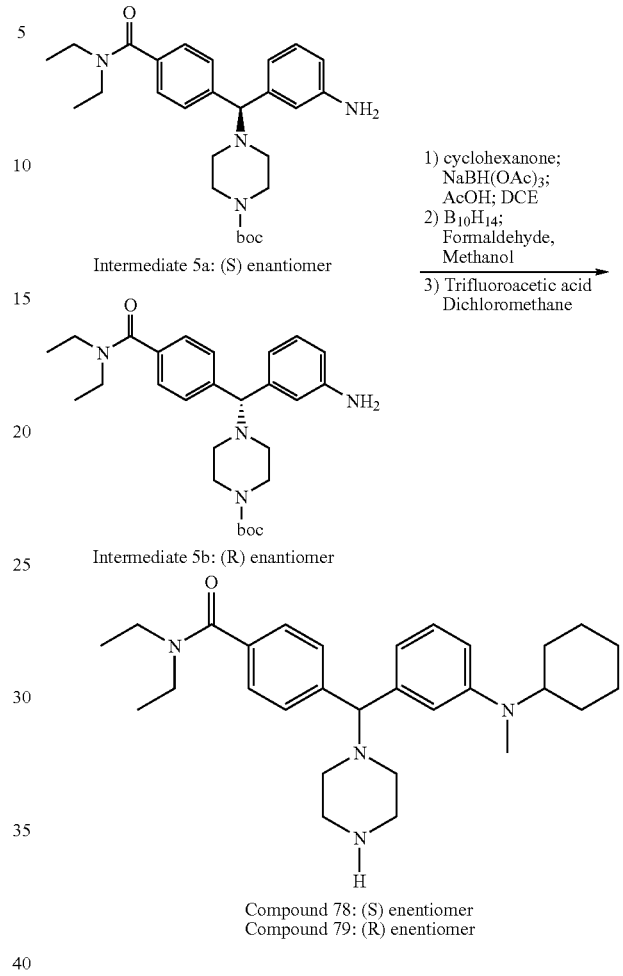

Compound 78: (S) enentiomer
Compound 79: (R) enentiomer

Biological Evaluation

The compounds of the invention are found to be active towards δ receptors in warm-blooded animal, e.g., human. Particularly the compounds of the invention are found to be effective δ receptor ligands. In vitro assays, infra, demonstrate these surprising activities, especially with regard to agonists potency and efficacy as demonstrated in the rat brain functional assay and/or the human δ receptor functional assay (low). This feature may be related to in vivo activity and may not be linearly correlated with binding affinity. In these in vitro assays, a compound is tested for their activity toward δ receptors and IC$_{50}$ is obtained to determine the selective activity for a particular compound towards δ receptors. In the current context, IC$_{50}$ generally refers to the concentration of the compound at which 50% displacement of a standard radioactive δ receptor ligand has been observed.

The activities of the compound towards κ and μ receptors are also measured in a similar assay.

In Vitro Model

Cell Culture

Human 293S cells expressing cloned human κ, δ and μ receptors and neomycin resistance are grown in suspension at 37° C. and 5% $CO_2$ in shaker flasks. containing calcium-free DMEM10% FBS, 5% BCS, 0.1% Pluronic F-68, and 600 μg/ml geneticin.

Rat brains are weighed and rinsed in ice-cold PBS (containing 2.5 mM EDTA, pH 7.4). The brains are homogenized with a polytron for 30 sec (rat) in ice-cold lysis buffer (50 mM Tris, pH 7.0, 2.5 mM EDTA, with phenylmethylsulfonyl fluoride added just prior use to 0.5 mM from a 0.5M stock in DMSO:ethanol).

Membrane Preparation

Cells are pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension is spun at 1000 g (max) for 10 min at 4° C. The supernatant is saved on ice and the pellets resuspended and spun as before. The supernatants from both spins are combined and spun at 46,000 g(max) for 30 min. The pellets are resuspended in cold Tris buffer (50 mM Tris/Cl, pH 7.0) and spun again. The final pellets are resuspended in membrane buffer (50 mM Tris, 0.32 M sucrose, pH 7.0). Aliquots (1 ml) in polypropylene tubes are frozen in dry ice/ethanol and stored at −70° C. until use. The protein concentrations are determined by a modified Lowry assay with sodium dodecyl sulfate.

Binding Assays

Membranes are thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which is stored at 4° C. after filtration through a 0.22 m filter, and to which has been freshly added 5 μg/ml aprotinin, 10 μM bestatin, 10 μM diprotin A, no DTT). Aliquots of 100 μl are added to iced 12×75 mm polypropylene tubes containing 100 μl of the appropriate radioligand and 100 μl of test compound at various concentrations. Total (TB) and nonspecific (NS) binding are determined in the absence and presence of 10 μM naloxone respectively. The tubes are vortexed and incubated at 25° C. for 60-75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters is measured with a beta counter after soaking the filters for at least 12 h in minivials containing 6-7 ml scintillation fluid. If the assay is set up in 96-place deep well plates, the filtration is over 96-place PEI-soaked unifilters, which are washed with 3×1 ml wash buffer, and dried in an oven at 55° C. for 2 h. The filter plates are counted in a TopCount (Packard) after adding 50 μl MS-20 scintillation fluid/well.

Functional Assays

The agonist activity of the compounds is measured by determining the degree to which the compounds receptor complex activates the binding of GTP to G-proteins to which the receptors are coupled. In the GTP binding assay, GTP[γ]$^{35}$S is combined with test compounds and membranes from HEK-293S cells expressing the cloned human opioid receptors or from homogenized rat and mouse brain. Agonists stimulate GTP[γ]$^{35}$S binding in these membranes. The $EC_{50}$ and $E_{max}$ values of compounds are determined from dose-response curves. Right shifts of the dose response curve by the delta antagonist naltrindole are performed to verify that agonist activity is mediated through delta receptors. For human δ receptor functional assays, $EC_{50}$ (low) is measured when the human δ receptors used in the assay were expressed at lower levels in comparison with those used in determining $EC_{50}$ (high). The $E_{max}$ values were determined in relation to the standard δ agonist SNC80, i.e., higher than 100% is a compound that have better efficacy than SNC80.

Procedure for Rat Brain GTP

Rat brain membranes are thawed at 37° C., passed 3 times through a 25-gauge blunt-end needle and diluted in the GTPγS binding (50 mM Hepes, 20 mM NaOH, 100 mM NaCl, 1 mM EDTA, 5 mM $MgCl_2$, pH 7.4, Add fresh: 1 mM DTT, 0.1% BSA). 120 μM GDP final is added membranes dilutions. The EC50 and Emax of compounds are evaluated from 10-point dose-response curves done in 300 μl with the appropriate amount of membrane protein (20 μg/well) and 100000-130000 dpm of GTPγ$^{35}$S per well (0.11-0.14 nM). The basal and maximal stimulated binding are determined in absence and presence of 3 μM SNC-80

Data Analysis

The specific binding (SB) was calculated as TB—NS, and the SB in the presence of various test compounds was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean±S.E.M. values of $IC_{50}$, $K_i$ and $n_H$ were reported for ligands tested in at least three displacement curves.

Based on the above testing protocols, we find that the compounds of the present invention and some of the intermediates used in the preparation thereof are active toward human δ receptors. Generally, the $IC_{50}$ towards human δ receptor for most compounds of the present invention is in the range of 0.15 nM-30.4 nM with an average of 2.30 nM. The $EC_{50}$ and % $E_{max}$ towards human δ receptor for these compounds are generally in the range of 2.4 nM-2325 nM and 60-114, respectively. The $IC_{50}$ towards human κ and μ receptors for these compounds is generally in the ranges of 329 nM-8457 nM and 16 nM-9560 nM, respectively.

Receptor Saturation Experiments

Radioligand $K_δ$ values are determined by performing the binding assays on cell membranes with the appropriate radioligands at concentrations ranging from 0.2 to 5 times the estimated $K_δ$ (up to 10 times if amounts of radioligand required are feasible). The specific radioligand binding is expressed as pmole/mg membrane protein. Values of $K_δ$ and $B_{max}$ from individual experiments are obtained from non-linear fits of specifically bound (B) vs. nM free (F) radioligand from individual according to a one-site model.

Determination of Mechano-Allodynia Using Von Frey Testing

Testing is performed between 08:00 and 16:00 h using the method described by Chaplan et al. (1994). Rats are placed in Plexiglas cages on top of a wire mesh bottom which allows access to the paw, and are left to habituate for 10-15 min. The area tested is the mid-plantar left hind paw, avoiding the less sensitive foot pads. The paw is touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair is applied from underneath the mesh floor perpendicular to the plantar surface with sufficient force to cause a slight buckling against the paw, and held for approximately 6-8 seconds. A positive response is noted if the paw is sharply withdrawn. Flinching immediately upon removal of the hair is also considered a positive response. Ambulation is considered an ambiguous response, and in such cases the stimulus is repeated.

Testing Protocol

The animals are tested on postoperative day 1 for the FCA-treated group. The 50% withdrawal threshold is determined using the up-down method of Dixon (1980). Testing is started with the 2.04 g hair, in the middle of the series. Stimuli are always presented in a consecutive way, whether ascending or descending. In the absence of a paw withdrawal response to the initially selected hair, a stronger stimulus is presented; in the event of paw withdrawal, the next weaker stimulus is chosen. Optimal threshold calculation by this method requires 6 responses in the immediate vicinity of the 50% threshold, and counting of these 6 responses begins when the first change in response occurs, e.g. the threshold is first crossed. In cases where thresholds fall outside the range of stimuli, values of 15.14 (normal sensitivity) or 0.41 (maximally allodynic) are respectively assigned. The resulting pattern of positive and negative responses is tabulated using the convention, X=no withdrawal; O=withdrawal, and the 50% withdrawal threshold is interpolated using the formula:

$$50\% \text{ g threshold}=10^{(Xf+k\delta)}/10,000$$

where Xf=value of the last von Frey hair used (log units); k=tabular value (from Chaplan et al. (1994)) for the pattern of positive/negative responses; and δ=mean difference between stimuli (log units). Here δ=0.224.

Von Frey thresholds are converted to percent of maximum possible effect (% MPE), according to Chaplan et al. 1994. The following equation is used to compute % MPE:

$$\% \text{ MPE} = \text{Drug treated threshold (g)} - \text{allodynia threshold (g)} \times 100 \text{Control threshold (g)} - \text{allodynia threshold (g)}$$

Administration of Test Substance

Rats are injected (subcutaneously, intraperitoneally, intravenously or orally) with a test substance prior to von Frey testing, the time between administration of test compound and the von Frey test varies depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1-100 μmol/kg.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

For the anxiety and anxiety-like indications, efficacy has been established in the geller-seifter conflict test in the rat.

For the functional gastrointestinal disorder indication, efficacy can be established in the assay described by Coutinho S V et al, in American Journal of Physiology—Gastrointestinal & Liver Physiology. 282(2):G307-16, February 2002, in the rat.

Additional in Vivo Testing Protocols

Subjects and Housing

Naïve male Sprague Dawley rats (175-200 g) are housed in groups of 5 in a temperature controlled room (22° C., 40-70% humidity, 12-h light/dark). Experiments are performed during the light phase of the cycle. Animals have food and water ad libitum and are sacrificed immediately after data acquisition.

Sample

Compound (Drug) testing includes groups of rats that do not receive any treatment and others that are treated with *E. coli* lipopolysaccharide(LPS). For the LPS-treated experiment, four groups are injected with LPS, one of the four groups is then vehicle-treated whilst the other three groups are injected with the drug and its vehicle. A second set of experiments are conducted involving five groups of rats; all of which receive no LPS treatment. The naive group receives no compound (drug) or vehicle; the other four groups are treated with vehicle with or without drug. These are performed to determine anxiolytic or sedative effects of drugs which can contribute to a reduction in USV.

Administration of LPS

Rats are allowed to habituate in the experimental laboratory for 15-20 min prior to treatment. Inflammation is induced by administration of LPS (endotoxin of gram-negative *E. coli* bacteria serotype 0111:B4, Sigma). LPS (2.4 μg) is injected intracerebro-ventricularly (i.c.v.), in a volume of 10 μl, using standard stereotaxic surgical techniques under isoflurane anaesthesia The skin between the ears is pushed rostrally and a longitudinal incision of about 1 cm is made to expose the skull surface. The puncture site is determined by the coordinates: 0.8 mm posterior to the bregma, 1.5 mm lateral (left) to the lambda (sagittal suture), and 5 mm below the surface of the skull (vertical) in the lateral ventricle. LPS is injected via a sterile stainless steel needle (26-G ⅜) of 5 mm long attached to a 100-μl Hamilton syringe by polyethylene tubing (PE20; 10-15 cm). A 4 mm stopper made from a cut needle (20-G) is placed over and secured to the 26-G needle by silicone glue to create the desired 5 mm depth.

Following the injection of LPS, the needle remains in place for an additional 10 s to allow diffusion of the compound, then is removed. The incision is closed, and the rat is returned to its original cage and allowed to rest for a minimum of 3.5 h prior to testing.

Experimental Setup for Air-Puff Stimulation

The rats remains in the experimental laboratory following LPS injection and compound (drug) administration. At the time of testing all rats are removed and placed outside the laboratory. One rat at a time is brought into the testing laboratory and placed in a clear box (9×9×18 cm) which is then placed in a sound-attenuating ventilated cubicle measuring 62(w)×35(d)×46(h) cm (BRS/LVE, Div. Tech-Serv Inc). The delivery of air-puffs, through an air output nozzle of 0.32 cm, is controlled by a system (AirStim, San Diego Intruments) capable of delivering puffs of air of fixed duration (0.2 s) and fixed intensity with a frequency of 1 puff per 10 s. A maximun of 10 puffs are administered, or until vocalisation starts, which ever comes first. The first air puff marks the start of recording.

Experimental Setup for and Ultrasound Recording

The vocalisations are recorded for 10 minutes using microphones (G.R.A.S. sound and vibrations, Vedbaek, Denmark) placed inside each cubicle and controlled by LMS (UMS CADA-X 3.5B, Data Acquisition Monitor, Troy, Mich.) software. The frequencies between 0 and 32000 Hz are recorded, saved and analysed by the same software (LMS CADA-X 3.5B, Time Data Processing Monitor and UPA (User Programming and Analysis)).

Compounds (Drugs)

All compounds (drugs) are pH-adjusted between 6.5 and 7.5 and administered at a volume of 4 ml/kg. Following compound (drug) administration, animals are returned to their original cages until time of testing.

Analysis

The recording is run through a series of statistical and Fourier analyses to filter (between 20-24 kHz) and to calculate the parameters of interest. The data are expressed as the mean±SEM. Statistical significance is assessed using T-test for comparison between naive and LPS-treated rats, and one way ANOVA followed by Dunnett's multiple comparison test (post-hoc) for drug effectiveness. A difference between groups is considered significant with a minimum p value of $\leq 0.05$. Experiments are repeated a minimum of two times.

EXAMPLES

The invention will further be described in more detail by the following Examples which describe methods whereby compounds of the present invention may be prepared, purified, analyzed and biologically tested, and which are not to be construed as limiting the invention.

INTERMEDIATE 1: 4-Iodo-N,N-diethylbenzamide

To a mixture of 4-iodo-benzoyl chloride (75 g) in 500 mL $CH_2Cl_2$ was added a mixture of $Et_3N$ (50 mL) and $Et_2NH$ (100 mL) at 0° C. After the addition, the resulting reaction mixture was warmed up to room temperature in 1 hr and was then washed with saturated ammonium chloride. The organic extract was dried ($Na_2SO_4$), filtered and concentrated. Residue was recrystallized from hot hexanes to give 80 g of INTERMEDIATE 1.

INTERMEDIATE 2: 4-[hydroxy(3-nitrophenyl)methyl]-N,N-diethylbenzamide

N,N-Diethyl-4-iodobenzamide (5.0 g, 16 mmol) was dissolved in THF (150 mL) and cooled to −78° C. under nitrogen atmosphere. n-BuLi (15 mL, 1.07 M solution in hexane, 16 mmol) was added dropwise during 10 min at −65 to −78° C. The solution was then canulated into 3-nitrobenzaldehyde (2.4 g, 16 mmol) in toluene/THF (approx. 1:1, 100 mL) at −78° C. $NH_4Cl$ (aq.) was added after 30 min. After concentration in vacuo, extraction with EtOAc/water, drying ($MgSO_4$) and evaporation of the organic phase, the residue was purified by chromatography on silica (0-75% EtOAc/heptane) to give INTERMEDIATE 2 (2.6 g, 50%). $^1H$ NMR ($CDCl_3$) δ 1.0-1.3 (m, 6H), 3.2, 3.5 (2m, 4H), 5.90 (s, 1H), 7.30-7.40 (m, 4H), 7.50 (m, 1H), 7.70 (d, J=8 Hz, 1H), 8.12 (m, 1H), 8.28 (m, 1H).

INTERMEDIATE 3: N,N-diethyl-4-[(3-nitrophenyl)(1-piperazinyl)methyl]benzamide

To a solution of alcohol INTERMEDIATE 2 (10.01 g, 30.5 mmol) in dichloromethane (200 mL) was added thionyl bromide (2.58 mL, 33.6 mmol). After one hour at room temperature the reaction was washed with saturated aqueous sodium bicarbonate (100 mL) and the organic layer was separated. The aqueous layer was washed with dichloromethane (3×100 mL) and the combined organic extracts were dried ($Na_2SO_4$), filtered and concentrated.

The crude benzyl bromide was dissolved in acetonitrile (350 mL) and piperazine (10.5 g, 122 mmol) was added. After heating the reaction for one hour at 65° C. the reaction was washed with saturated amonium chloride/ethyl acetate and the organic layer was separated. The aqueous layer was extracted with ethyl acetate (3×100 mL) and the combined organic extracts were dried ($Na_2SO_4$), filtered and concentrated to give racemic INTERMEDIATE 3.

INTERMEDIATE 4a: Enantiomerically Pure N,N-diethyl-4-[(S)-(3-nitrophenyl)(1-piperazinyl)methyl]benzamide and 4b: Enantiomerically Pure N,N-diethyl-4-[(R)-(3-nitrophenyl)(1-piperazinyl)methyl]benzamide Racemic INTERMEDIATE 3 is resolved to give enantiomerically pure INTERMEDIATE 4a and 4b as follows:

The INTERMEDIATE 3 was dissolved in ethanol (150 mL) and di-p-toluoyl-D-tartaric acid (11.79 g, 1 equivalent) was added. The product precipitated out over a 12 hour period. The solid was collected by filtration and was redissolved in refluxing ethanol until all of the solid dissolved (approximately 1200 mL ethanol). Upon cooling the solid was collected by filtration and the recrystallization repeated a second time. The solid was collected by filtration and was treated with aqueous sodium hydroxide (2 M) and was extracted with ethyl acetate. The organic extract was then dried ($Na_2SO_4$), filtered and concentrated to give 1.986 g of enantiomerically pure INTERMEDIATE 4b. This INTERMEDIATE 4b has a negative optical rotation $^1H$ NMR (400 MHz, $CDCl_3$) δ 1.11 (br s, 3H), 1.25 (br s, 3H), 2.37 (br s, 4H), 2.91 (t, J=5 Hz, 4H), 3.23 (br s, 2H), 3.52 (br s, 2H), 4.38 (s, 1H), 7.31-7.33 (m, 2H), 7.41-7.43 (m, 2H), 7.47 (t, J=8 Hz, 1H), 7.75-7.79 (m, 1H), 8.06-8.09 (m, 1H), 8.30-8.32 (m, 1H).

INTERMEDIATE 4b: Enantiomerically Pure N,N-diethyl-4-[(S)-(3-nitrophenyl)(1-piperazinyl)methyl]benzamide and 4b The (S) enantiomer INTERMEDIATE 4a may be obtained by performing the above resolution procedure with di-p-toluoyl-L-tartaric acid.

Chiral purity was determined by HPLC using the following conditions:
Chiralpack AD column (Daicel Chemical Industries);
Flow rate 1 mL/minute;
Run time 30 minutes at 25° C.;
Isocratic 15% ethanol 85% hexanes.

INTERMEDIATE 5a or 5b: tert-Butyl 4-((3-aminophenyl){4-[(diethylamino)carbonyl]phenyl}methyl)piperazine-1-carboxylate To a solution of INTERMEDIATE 4a or 4b (300 mg) in dioxane (40 mL) was added di-tert-butyl dicarbonate (247 g; 1.5 eq). Sodium carbonate (119 g; 1.5 eq) was dissolved in water (15 mL) and then added in the dioxane solution. After 12 hours the solution was concentrated and saturated sodium bicarbonate was then added. The aqueous solution was extracted with three portions of dichloromethane and the combined organics were dried over anhydrous sodium sulfate, filtered and concentrated to afford a white foam. Without further purification, the foam was then dissolved in a mixture of ethanol, tetrahydrofuran, water and saturated ammonium chloride (15 mL; ratios 4:2:1:1 v/v). Iron granules (422 g; 10 eq) were added and the solution was heated at 90° C. for 1.5 hour. The resulting mixture was cooled, filtered through celite and concentrated. Saturated sodium bicarbonate was added and the aqueous solution was extracted with three portions of dichloromethane and the combined organics were dried over anhydrous sodium sulfate, filtered and concentrated to afford a white foam INTERMEDIATE 5a or 5b, respectively. The product can be use without any further purification. (92-99% yield), $^1$H NMR (400 MHz, CDCl$_3$) 1.06-1.16 (m, 3H), 1.17-1.26 (m, 3H), 1.44 (s, 9H), 2.28-2.39 (m, 4H), 3.20-3.31 (br s, 2H), 3.37-3.44 (br s, 2H), 3.48-3.58 (br s, 2H), 3.60-3.70 (br s, 2H), 4.12 (s, 1H), 6.51-6.55 (m, 1H), 6.72 (t, J=2.13 Hz, 1H), 6.79 (d, J=8.17 Hz, 1H), 7.06 (t, J=7.46 Hz, 1H), 7.29 (d, J=7.82 Hz, 2H), 7.43 (d, J=7.82 Hz, 2H).

Intermediate 6a tert-butyl 4-((R)-(3-anilinophenyl){4-[(diethylamino)carbonyl]phenyl}methyl)piperazine-1-carboxylate or 6b tert-butyl 4-((R)-(3-anilinophenyl){4-[(diethylamino)carbonyl]phenyl}methyl)piperazine-1-carboxylate To a solution of INTERMEDIATE 5a or 5b (325 mg) in toluene (2 mL) was added bromo benzene (94 µL; 1.3 eq), Pd$_2$(dba)$_3$ (25 g; 0.04 eq), Sodium tert-butoxide (93 g; 1.4 eq) and BINAP (34 g; 0.08 eq). The solution was heated in the microwave in a sealed-tube for 5 min at 110° C. The resulting mixture filtered through celite and concentrated. The crude was purified by a normal phase MPLC with a disposable silica gel column (40 g); eluting 40% to 60% ethyl acetate in hexane. Pure fraction was collected and concentrated to afford yellow foam (338 g; 89% yield).

$^1$H NMR (400 MHz, CDCl$_3$) 1.07 (t, J=6.64 Hz, 3H), 1.19 (t, J=6.83 Hz, 3H), 1.40 (s, 9H), 2.28-2.39 (m, 4H), 3.20-3.31 (br s, 2H), 3.20-3.27 (m, 2H), 3.37-3.43 (m, 4H), 3.45-3.53 (m, 2H), 4.21 (s, 1H), 6.80 (tt, J=7.35, 1.15 Hz, 1H), 6.84-6.88 (m, 2H), 6.95-6.99 (m, 2H), 7.09 (t, J=8.00 Hz, 1H), 7.13-7.19 (m, 3H), 7.28 (d, J=8.40 Hz, 2H), 7.51 (d, J=8.20 Hz, 2H).

Compound 1: N,N-diethyl-4-((S)piperazin-1-yl{3-[(1,3-thiazol-2-ylmethyl)amino]phenyl}methyl)benzamide

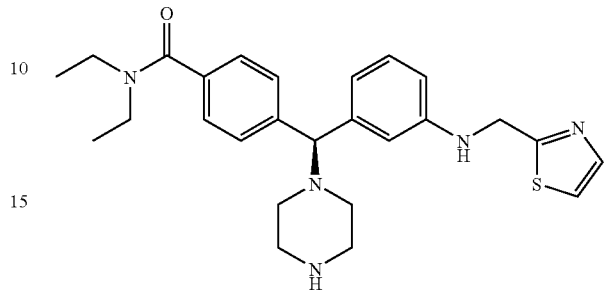

To a solution of INTERMEDIATE 5a (477 mg) in 1,2-dichloroethane (15 mL) was added 2-thiazole carboxaldehyde (179 µL; 2 eq) and sodium triacetoxyborohydride (432 g; 2 eq). The reaction was stirred at room temperature under nitrogen. After 24 hours the reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (15 mL) and trifluoroacetic acid (1.5 mL) was added. The reaction was allowed to stir overnight. The solution was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by flash chromatography eluting with 5% methanol, 1% ammonium hydroxide in dichloromethane rising to 15% methanol, 1.5% ammonium hydroxide in dichloromethane. The product obtained was further purified by reverse phase chromatography, eluting 5% to 55% acetonitrile in water containing 0.1% trifluoroacetic acid. The product was obtained as the trifluoroacetic acid salt and was lyophilized to give COMPOUND 1 (162 mg, 20% yield) as a colourless solid. Purity (HPLC): >99%; Optical purity (Chiral HPLC): >99%; $^1$H NMR (400 MHz, CD$_3$OD) 1.07 (br s, 1H), 1.2 (br s, 1H), 2.55 (br s, 4H), 3.09-3.31 (m, 6H), 3.49 (br s, 2H), 4.26 (s, 1H), 4.61 (s, 2H), 6.5 (d, J=8.51 Hz, 1H), 6.69 (s, 2H), 7.01 (t, J=7.57 Hz, 1H), 7.22-7.28 (m, 2H), 7.40-7.47 (m, 3H), 7.73 (s, 1H). Found: C, 53.09; H, 5.52; N, 10.07. C$_{26}$H$_{33}$N$_5$OS×1.6CF$_3$CO$_2$H×0.8H$_2$O has C, 53.10 H, 5.52; N, 10.60%.

Compound 2: N,N-diethyl-4-((R)-piperazin-1-yl{3-[(1,3-thiazol-2-ylmethyl)amino]phenyl}methyl)benzamide

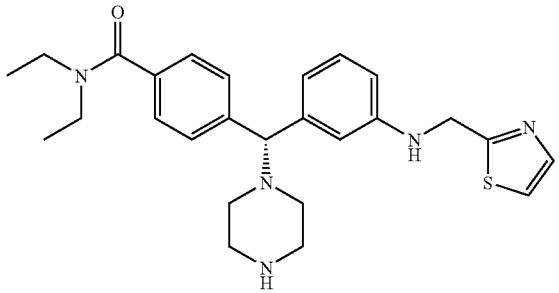

To a solution of INTERMEDIATE 5b (167 mg) in 1,2-dichloroethane (10 mL) was added 2-thiazole carboxaldehyde (62 µL; 2 eq) and sodium triacetoxyborohydride (152 g; 2 eq). The reaction was stirred at room temperature under nitrogen. After 18 hours the reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (10 mL) and trifluoroacetic acid (1 mL) was added. After 18 hours the solution was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 5% to 50% acetonitrile in water containing 0.1% trifluoroacetic acid. The product was obtained as the trifluoroacetic acid salt and was lyophilized to give COMPOUND 2 (90 mg, 31% yield) as a colourless solid. Purity (HPLC): >99%; Optical purity (Chiral HPLC): >99%; $^1$H NMR (400 MHz, CD$_3$OD) 1.07 (br s, 1H), 1.2 (br s, 1H), 2.55 (br s, 4H), 3.09-3.31 (m, 6H), 3.49 (br s, 2H), 4.26 (s, 1H), 4.61 (s, 2H), 6.5 (d, J=8.51 Hz, 1H), 6.69 (s, 2H), 7.01 (t, J=7.57 Hz, 1H), 7.22-7.28 (m, 2H), 7.40-7.47 (m, 3H), 7.73 (s, 1H). Found: C, 48.90; H, 5.12 N, 9.13. $C_{26}H_{33}N_5OS \times 2.4CF_3CO_2H \times 1.1H_2O$ has C, 48.86 H, 5.01; N, 9.25%. $[\alpha]_D = -23.68$ deg [c 0.625, MeOH].

Compound 3: 4-[(S)-[3-(benzylamino)phenyl](piperazin-1-yl)methyl]-N,N-diethylbenzamide

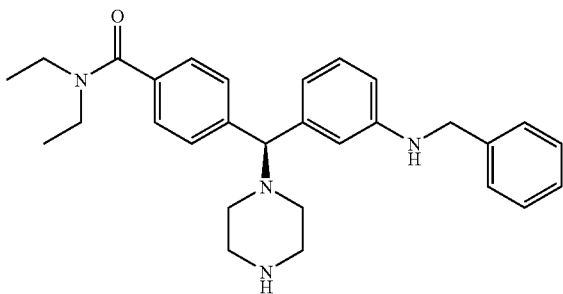

To a solution of INTERMEDIATE 5a (176 mg) in 1,2-dichloroethane (10 mL) was added benzaldehyde (77 µL; 2 eq) and sodium triacetoxyborohydride (159 g; 2 eq). The reaction was stirred at room temperature under nitrogen. After 18 hours the reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (10 mL) and trifluoroacetic acid (1 mL) was added. After 18 hours the solution was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 5% to 50% acetonitrile in water containing 0.1% trifluoroacetic acid. The product was obtained as the trifluoroacetic acid salt and was lyophilized to give COMPOUND 3 (127 mg, 42% yield) as a colourless solid. Purity (HPLC): >99%; Optical purity (Chiral HPLC): >99%; $^1$H NMR (400 MHz, CD$_3$OD) 1.07 (m, 3H), 1.20 (m, 3H), 2.53 (br s, 4H), 3.13 (q, J=5.1 Hz, 4H), 3.20-3.25 (m, 2H), 3.45-3.51 (m, 2H), 4.31 (s, 1H), 4.38, (s, 2H), 6.73-6.78 (m, 1H), 6.85-6.93 (m, 2H), 7.14 (t, J=7.6 Hz, 1H), 7.23-7.33 (m, 7H), 7.43 (d, J=8.0 Hz, 2H). Found: C, 53.88; H, 5.25; N, 7.40. $C_{29}H_{36}N_4O \times 2.6CF_3CO_2H \times 0.5H_2O$ has C, 53.90; H, 5.24; N, 7.35%. $[\alpha]_D^{20} = +25.74$ deg [c0.672, MeOH].

Compound 4: N,N-diethyl-4-((R)-piperazin-1-yl{3-[(thien-2-ylmethyl)amino]phenyl}methyl)benzamide

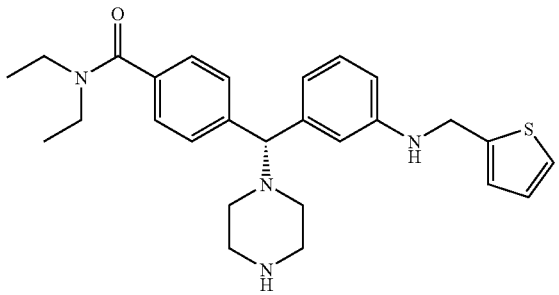

To a solution of INTERMEDIATE b (158 mg) in 1,2-dichloroethane (10 mL) was added 2-thiophene carboxaldehyde (63 µL; 2 eq) and sodium triacetoxyborohydride (144 g; 2 eq). The reaction was stirred at room temperature under nitrogen. After 18 hours the reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (10 mL) and trifluoroacetic acid (1 mL) was added. After 18 hours the solution was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 5% to 50% acetonitrile in water containing 0.1% trifluoroacetic acid. The product was obtained as the trifluoroacetic acid salt and was lyophilized to give COMPOUND 4 (62 mg, 12% yield) as a colourless solid. Purity (HPLC): >99%; Optical purity (Chiral HPLC): >99%; $^1$H NMR (400 MHz CD$_3$OD) 1.07 (m, 3H), 1.20 (m, 3H), 2.51-2.61 (m, 4H), 3.13-3.18 (m, 4H), 3.19-3.25 (m, 2H), 3.45-3.52 (m, 2H), 4.30 (s, 1H), 4.50 (s, 2H), 6.62 (ddd, J=8.14, 2.26, 0.94 Hz, 1H), 6.76 (d, J=7.59 Hz, 1H), 6.82 (t, J=2.16 Hz, 1H), 6.92 (dd, J=5.03, 3.45 Hz, 1H), 6.95-6.98 (m, 1H), 7.06 (t, J=7.91 Hz, 1H), 7.23 (dd, J=5.03, 1.15 Hz, 1H), 7.27 (d, J=8.34 Hz, 2H), 7.47 (d, J=8.20 Hz, 2H). Found: C, 53.07; H, 5.26; N, 8.22. $C_{27}H_{34}N_4OS \times 2.0CF_3CO_2H \times 0.6H_2O$ has C, 53.08; H, 5.35 N, 7.39%. $[\alpha]_D^{20} = -27.71$ deg [c0.635, MeOH].

Compound 5: N,N-diethyl-4-((S)-piperazin-1-yl{3-[(thien-2-ylmethyl)amino]phenyl}methyl)benzamide

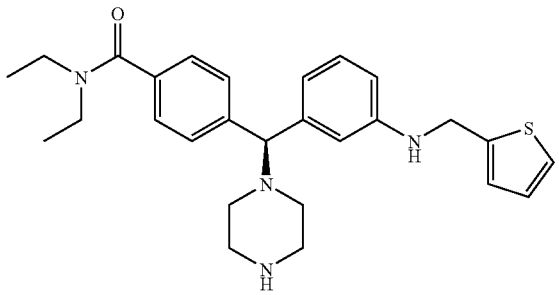

To a solution INTERMEDIATE 5a (150 mg) in 1,2-dichlorethane (10 mL) was added 2-thiophenecarboxaldehyde (33 µL; 1.1 eq) and sodium triacetoxyborohydride (74 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography with a gradient from 5% to 45% acetonitrile in water containing 0.1%,trifluoroacetic acid. The product was obtained as the trifluoroacetic acid salt and was lyophilized to give COMPOUND 5 (118 mg, 46% yield) as a colourless solid. Purity (HPLC): >99%; Optical purity (Chiral HPLC): >99%; $^1$H NMR (400 MHz, CD$_3$OD) 1.07 (m, 3H), 1.20 (m, 3H), 2.51-2.61 (m, 4H), 3.13-3.18 (m, 4H), 3.19-3.25 (m, 2H), 3.45-3.52 (m, 2H), 4.30 (s, 1H), 4.50 (s, 2H), 6.62 (ddd, J=8.14, 2.26, 0.94 Hz, 1H), 6.76 (d, J=7.59 Hz, 1H), 6.82 (t, J=2.16 Hz, 1H), 6.92 (dd, J=5.03, 3.45 Hz, 1H), 6.95-6.98 (m, 1H), 7.06 (t, J=7.91 Hz, 1H), 7.23 (dd, J=5.03, 1.15 Hz, 1H), 7.27 (d, J=8.34 Hz, 2H), 7.47 (d, J=8.20 Hz, 2H). Found: C, 48.42; H, 4.70; N, 6.91. C$_{27}$H$_{34}$N$_4$OS×3.0CF$_3$CO$_2$H×0.8H$_2$O has C, 48.39 H, 4.75; N, 6.84%. [α]$_D$=+21.30 deg [c 0.784, MeOH].

Compound 6: N,N-diethyl-4-[(S)-{3-[(2-furylmethyl)amino]phenyl}(piperazin-1-yl)methyl]benzamide

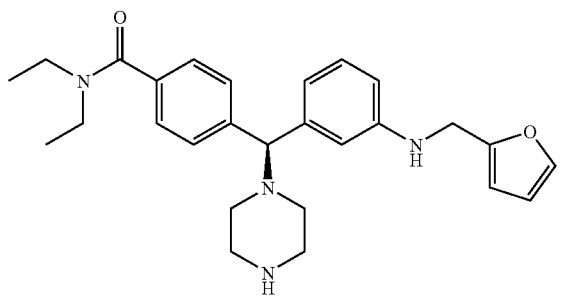

To a solution of INTERMEDIATE 5a (150 mg) in 1,2-dichloroethane (10 mL) was added 2-furaldehyde (29 μL; 1.1 eq) and sodium triacetoxyborohydride (74 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 5% to 45% acetonitrile in water containing 0.1% trifluoroacetic acid. The product was obtained as the trifluoroacetic acid salt and was lyophilized to give COMPOUND 6 (82 mg, 33% yield) as a colourless solid. Purity (HPLC): >99%; Optical purity (Chiral HPLC): >99%; $^1$H NMR (400 MHz, CD$_3$OD) 1.09 (t, J=6.80 Hz, 3H), 1.21 (t, J=6.7 Hz, 3H), 2.58-2.65 (m, 4H), 3.19-3.26 (m, 6H), 3.51 (q, J=7.50 Hz, 2H), 4.38 (s, 2H), 4.39 (s, 1H), 6.23 (d, J=2.93 Hz, 1H), 6.31-6.34 (m, 1H), 6.75-6.79 (m, 1H), 6.96 (d, J=7.42 Hz, 2H), 7.17 (t, J=7.60 Hz, 1H), 7.31 (d, J=8.20 Hz, 2H), 7.44 (s, 1H), 7.52 (d, J=8.20 Hz, 2H). Found: C, 51.70; H, 5.20; N, 7.53. C$_{27}$H$_{34}$N$_4$O$_2$×2.5CF$_3$CO$_2$H×0.6H$_2$O×0.1 CH$_2$OH has C, 51.71; H, 5.15; N, 7.51%. [α]$_D$=+14.72 deg [c 0.679, MeOH].

Compound 7: 4-[(R)-[3-(benzylamino)phenyl](piperazin-1-yl)methyl]-N,N -diethylbenzamide

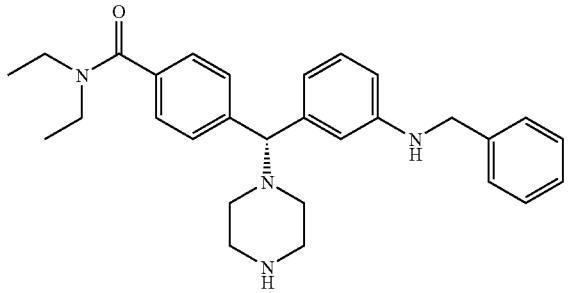

To a solution of INTERMEDIATE 5b (90 mg) in 1,2-dichloroethane (5 mL) was added benzaldehyde (21 μL; 1.1 eq) and sodium triacetoxyborohydride (45 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of the dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 7 (48 mg, 31% yield) as a colourless solid. Purity (HPLC): >99%; Optical purity (Chiral HPLC): >99%; $^1$H NMR (400 MHz, CD$_3$OD) 1.07 (m, 3H), 1.20 (m, 3H), 2.53 (br s, 4H), 3.13 (q, J=5.1 Hz, 4H), 3.20-3.25 (m, 2H), 3.45-3.51 (m, 2H), 4.31 (s, 1H), 4.38, (s, 2H), 6.73-6.78 (m, 1H), 6.85-6.93 (m, 2H), 7.14 (t, J=7.6 Hz, 1H), 7.23-7.33 (m, 7H), 7.43 (d, J=8.0 Hz, 2H). Found: C, 58.49; H, 5.69; N, 8.58. C$_{29}$H$_{36}$N$_4$O×1.8CF$_3$CO$_2$H×0.4H$_2$O has C, 58.52; H, 5.82; N, 8.37%. [α]$_D$=−32.24 deg [c 0.943, MeOH].

Compound 8: N,N-diethyl-4-[(R)-{3-[(2-furylmethyl)amino]phenyl}(piperazin-1-yl)methyl]benzamide

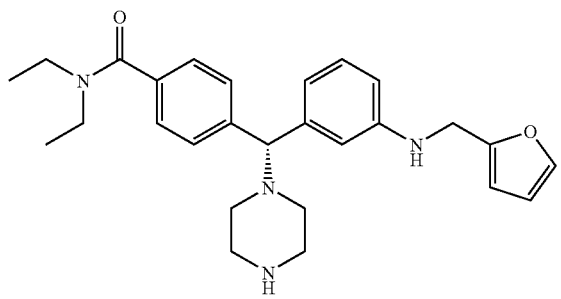

To a solution of INTERMEDIATE 5b (90 mg) in 1,2-dichloroethane (5 mL) was added 2-furaldehyde (18 μL; 1.1 eq) and sodium triacetoxyborohydride (45 g; 1.1 eq). The reaction was stirred at room temperature under nitrogen.

After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 8 (35 mg, 31% yield) as a colourless solid. PurityW (HLC): >99%; Optical purity (Cuiral HPLC): >99%, $^1$HNMR(400 MHz, CD$_3$OD) 1.09 (t, J=6.80 Hz; 3H), 1.21 (t, J=6.7 Hz, 3H), 2.58-2.65 (m, 4H), 3.19-3.26 (m, 6H), 3.51 (q, J=7.50 Hz, 2H), 4.38 (s, 2H), 4.39 (s, 1H), 6.23 (d, J=2.93 Hz, 1H), 6.31-6.34 (m, 1H), 6.75-6.79 (m, 1H), 6.96 (d, J=7.42 Hz, 2H), 7.17 (t, J=7.60 Hz, 1H), 7.31 (d, J=8.20 Hz, 2H), 7.44 (s, 1H), 7.52 (d, J=8.20 Hz, 2H). Found: C, 48.96; H, 4.90; N, 7.02. C$_{27}$H$_{34}$O$_2$×3.0CF$_3$CO$_2$H×1.1H$_2$O has C, 49.03; H, 4.89; N, 6.93%. [α]$_D$=−12.55 deg [c 10.02, MeOH].

Compound 9: N,N-diethyl-4-((R)-piperazin-1-yl{3-[(thien-3-ylmethyl)amino]phenyl}methyl)benzamide

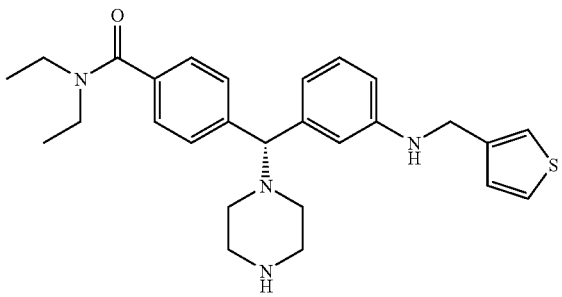

To a solution of INTERMEDIATE 5b (90 mg) in 1,2-dichloroethane (5 mL) was added 3-thiophene carboxaldehyde (19 μL; 1.1 eq) and sodium triacetoxyborohydride (45 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 9 (44 mg, 28% yield) as a colourless solid. Purity (HPLC): >99%; Optical purity (Chiral HPLC): >99%; $^1$H NMR (400 MHz, CD$_3$OD) 1.09 (t, J=6.68 Hz, 3H), 1.22 (t, J=6.68 Hz, 3H), 2.53-2.61 (m, 4H), 3.17-3.27 (m, 6H), 3.47-3.55 (m, 2H), 4.38 (s, 1H), 4.43 (s, 2H), 6.83-6.89 (m, 1H), 6.98-7.08 (m, 3H), 7.22 (t, J=7.68 Hz, 1H), 7.22-7.27 (m, 1H), 7.30 (d, J=8.35 Hz, 2H), 7.37 (dd, J=4.67, 3.24 Hz, 1H), 7.48 (d, J=8.01 Hz, 2H). Found: C, 51.83; H, 5.14; N, 7.78. C$_{27}$H$_{34}$N$_4$OS×2.CF$_3$CO$_2$H×0.8H$_2$O has C, 51.81; H, 5.23; N, 7.70%. [α]$_D$=−20.06 deg [c 0.708, MeOH].

Compound 10: N,N-diethyl-4-((S)-piperazin-1-yl{3-[(thien-3-ylmethyl)amino]phenyl}methyl)benzamide

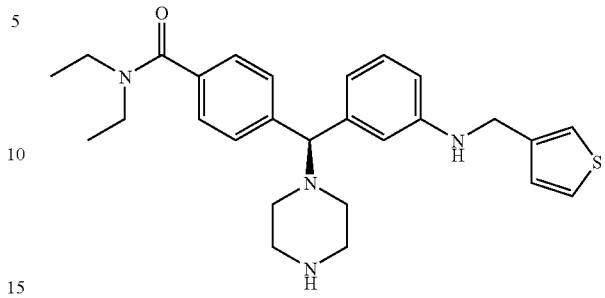

To a solution of INTERMEDIATE 5a (168 mg) in 1,2-dichloroethane (5 mL) was added 3-thiophene carboxaldehyde (34 μL; 1.1 eq) and sodium triacetoxyborohydride (82 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography eluting with 10% to 45% acetonitrile in water containing 0.1% trifluoroacetic acid. The product was obtained as the trifluoroacetic acid salt and was lyophilized to give COMPOUND 10 (69 mg, 24% yield) as a colourless solid. Purity (HPLC): >99%; Optical purity (Chiral HPLC): >99%; $^1$H NMR (400 MHz, CD$_3$OD) 1.09 (t, J=6.68 Hz, 3H), 1.22 (t, J=6.68 Hz, 3H), 2.53-2.61 (m, 4H), 3.17-3.27 (m, 6H), 3.47-3.55 (m, 2H), 4.38 (s, 1H), 4.43 (s, 2H), 6.83-6.89 (m, 1H), 6.98-7.08 (m, 3H), 7.22 (t, J=7.68 Hz, 1H), 7.22-7.27 (m, 1H), 7.30 (d, J=8.35 Hz, 2H), 7.37 (dd, J=4.67, 3.24 Hz, 1H), 7.48 (d, J=8.01 Hz, 2H). Found: C, 49.26; H, 4.84; N, 7.24. C$_{27}$H$_{34}$N$_4$OS×2.8CF$_3$CO$_2$H×0.7H$_2$O has C, 49.28; H, 4.85; N, 7.05%. [a]$_D^{20}$=+13.98 deg [c 0.615, MeOH].

Compound 11: N,N-diethyl-4-[(R)-{3-[(3-furylmethyl)amino]phenyl}(piperazin-1-yl)methyl]benzamide

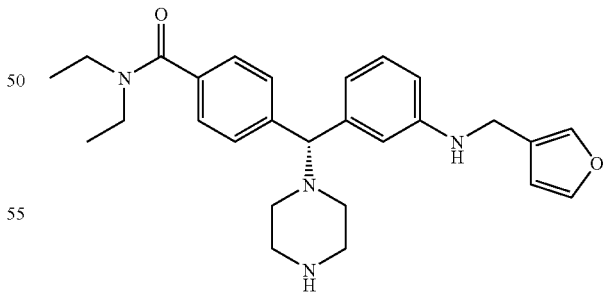

To a solution of INTERMEDIATE 5b (168 mg) in 1,2-dichloroethane (5 mL) was added 3-furaldehyde (34 μL; 1.1 eq) and sodium triacetoxyborohydride (82 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 11 (34 mg, 11% yield) as a colourless solid. Purity (HPLC): >99%; Optical purity (Chiral HPLC): >99%; $^1$H NMR (400 MHz, CD$_3$OD) 1.09 (t, J=6.66 Hz, 3H), 1.21 (t, J=6.60 Hz, 3H), 2.55-2.66 (m, 4H), 3.15-3.27(m, 6H), 3.47-3.55 (m, 2H), 4.18 (s, 2H), 4.33 (s, 1H), 6.37-6.39 (m, 1H), 6.64-6.68 (m, 1H), 6.81-6.87 (m, 3H), 7.11 (t, J=7.65 Hz, 1H), 7.30 (d, J=8.65 Hz, 2H), 7.38-7.43 (m, 1H), 7.51 (d, J=7.98 Hz, 2H). Found: C, 56.40; H, 5.39; N, 8.75. C$_{27}$H$_{34}$N$_4$O$_2$×1.8CF$_3$CO$_2$H×1.0H$_2$O has C, 56.38; H, 5.54; N, 8.60%. $[a]_D^{20}$=-12.24 deg [c 0.580, MeOH].

Compound 12: N,N-diethyl-4-[(R)-{3-[(2-phenylethyl)amino]phenyl}(piperazin-1-yl)methyl]benzamide

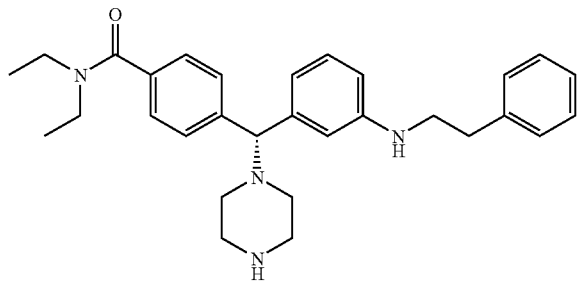

To a solution of INTERMEDIATE 5b (70 mg) in 1,2-dichloroethane (5 mL) was added phenyl acetaldehyde (253 μL/0.65 M in DCE; 1.1 eq) and sodium triacetoxyborohydride (35 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 12 (23 mg, 11% yield) as a colourless solid. Purity (HPLC): >99%; Optical purity (Chiral HPLC): >99%; $^1$H NMR (400 MHz, CD$_3$OD) 1.06 (t, J=7.27 Hz, 3H), 1.21 (t, J=6.66 Hz, 3H), 2.60-2.69 (m, 4H), 2.85 (t, J=7.27 Hz, 2H), 3.20-3.26 (m, 6H), 3.35 (t, J=6.96 Hz, 2H), 3.46-3.54 (m, 2H), 4.37 (s,1H), 6.66-6.70 (m, 1H), 6.87-6.92 (m, 2H), 7.15 (t, J=7.88 Hz, 1H), 7.19 (s, 1H), 7.21 (s, 1H), 7.32 (d, J=8.17 Hz, 2H), 7.56 (d, J=8.17 Hz). Found: C, 58.72; H, 5.79; N, 8.25. C$_{30}$H$_{38}$N$_4$O×1.9CF$_3$CO$_2$H×0.2H$_2$O has C, 58.76; H, 5.88; N, 8.11%. $[\alpha]_D$=-1 deg [c 0.571, MeOH].

Compound 13: 4-[(R)-{3-[(cyclohexylmethyl)amino]phenyl}(piperazin-1-yl)methyl]-N,N-diethyl-benzamide

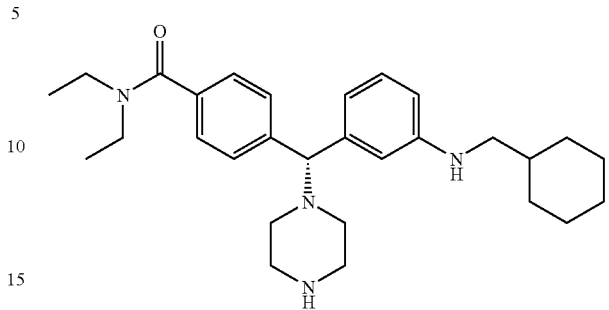

To a solution of INTERMEDIATE 5b (200 mg) in 1,2-dichloroethane (10 mL) was added cyclohexyl carboxaldehyde (57 μL; 1.1 eq) and sodium triacetoxyborohydride (99 g; 1.1 eq). The reaction was stirred at room temperature under nitrogen. After 18 hours, trifluoroacetic acid (1 mL) was added to the reaction and stirred for 4 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 13 (37 mg, 11% yield) as a colourless solid. Purity (HPLC): >99%; Optical purity (Chiral HPLC): >99%; $^1$H NMR (400 MHz, CD$_3$OD) 0.98-1.06 (m, 2H), 1.06-1.11 (m, 4H), 1.17-1.26 (m, 6H), 1.58-1.68 (m, 1H), 1.72-1.84 (m, 4H), 2.65 (br s, 4H), 3.09 (d, J=6.85 Hz, 2H), 3.22-3.28 (m, 6H), 3.48-3.55 (m, 2H), 4.49 (s, 1H), 7.00-7.04 (m, 1H), 7.24-7.30 (m, 2H), 7.31-7.36 (m, 3H), 7.55 (d, J=8.17 Hz, 2H). $[a]_D^{20}$=-4.28 deg [c 0.864, MeOH].

Compound 14: N,N-diethyl-4-[(R)-piperazin-1-yl(3-{[4-trifluoromethyl)benzyl]amino}phenyl)methyl]benzamide

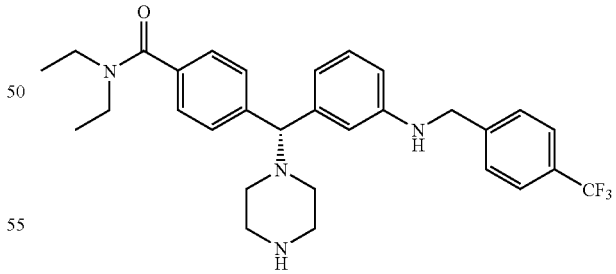

To a solution of INTERMEDIATE 5b (102 mg) in 1,2-dichloroethane (4 mL) was added 4-trifluoromethyl benzaldehyde (45 μL; 1.5 eq) and sodium triacetoxyborohydride (70 g; 1.5 eq). The reaction was stirred at room temperature under nitrogen. After 18 hours, trifluoroacetic acid (0.5 mL) was added to the reaction and stirred for 5 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 14 (51 mg, 27% yield) as a colourless solid. Purity (HPLC): >99%; Optical purity (Chiral HPLC): >99%; $^1$H NMR (400 MHz, CD$_3$OD) 1.06 (t, J=6.64 Hz, 3H), 1.19 (t, J=6.83 Hz, 3H), 2.54-2.63 (m, 4H), 3.08-3.16 (m, 4H), 3.17-3.25 (m, 2H), 3.44-3.53 (m, 2H), 4.23 (s, 1H), 4.39 (s, 2H), 6.49 (ddd, J=8.15, 2.39, 0.98 Hz, 1H), 6.61 (t, J=1.85 Hz, 1H), 6.63-6.67 (m, 1H), 7.00 (t, J=7.81 Hz, 1H), 7.22 (d, J=8.32 Hz, 2H), 7.39 (d, J=8.20 Hz, 2H), 7.49 (d, J=8.01 Hz, 2H), 7.57 (d, J=8.21 Hz, 2H). Found: C, 56.14; H, 5.49; N, 7.91. C$_{30}$H$_{35}$N$_4$O×1.0H$_2$O×1.4CF$_3$COOH has C, 56.10; H, 5.51; N, 10.94%. [a]$_D^{20}$=−21.90 deg [c 1.073, MeOH].

Compound 15: 4-[(R)-{3-[(cyclopentylmethyl)amino]phenyl}(piperazin-1-yl)methyl]-N,N-diethyl-benzamide

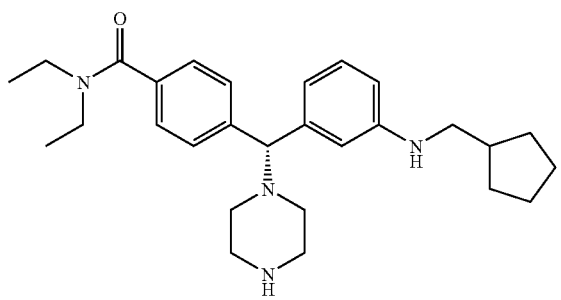

To a solution of INTERMEDIATE 5b (80 mg) in 1,2-dichloroethane (3 mL) was added cyclopentane carboxaldehyde (20 g; 1.5 eq) and sodium triacetoxyborohydride (51 g; 1.5 eq). The reaction was stirred at room temperature under nitrogen. After 18 hours, trifluoroacetic acid (0.5 mL) was added to the reaction and stirred for 5 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by flash chromatography on silica gel, eluting 1% NH$_4$OH 10% MeOH in dichloromethane. The pure product was obtained and dissolved in dichloromethane in which 200 μL of 1M HCl in ether was added. Solvent was removed and the product was isolated as the hydrochloride salt to give COMPOUND 15 (27 mg, 28% yield) as a colourless solid. Purity (HPLC): >99%; Optical purity (Chiral HPLC): >99%; $^1$H NMR (400 MHz, CD$_3$OD) 1.06 (t, J=6.59 Hz, 3H), 1.19 (t, J=6.79 Hz, 3H), 1.22-1.28 (m, 2H), 1.52-1.68 (m, 4H), 1.76-1.86 (m, 2H), 2.05-2.15 (m, 1H), 2.56-2.68 (m, 4H), 3.11 (d, J=7.32 Hz, 2H), 3.18-3.25 (m, 6H), 3.46-3.53 (m, 2H), 4.42 (s, 1H), 6.85-6.87 (m, 1H), 7.07-7.13 (m, 2H), 7.24 (t, J=8.15 Hz, 1H), 7.30 (d, J=8.39 Hz, 2H), 7.53 (d, J=8.08 Hz, 2H). Found: C, 53.18; H, 7.35; N, 8.26. C$_{28}$H$_{40}$N$_4$O×2.4H$_2$O×0.6HCl×1.9CH$_2$Cl$_2$ has C, 53.19; H, 7.35; N, 8.06%. [a]$_D^{20}$=−15.25 deg [c 0.223, MeOH].

Compound 16: 4-[(S)-{3-[(cyclohexylmethyl)amino]phenyl}(piperazin-1-yl)methyl]-N,N-diethyl-benzamide

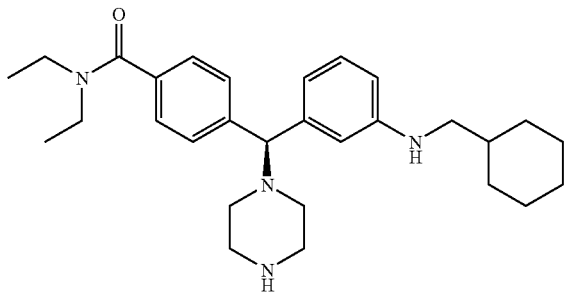

To a solution of INTERMEDIATE 5a (101 mg) in 1,2-dichloroethane (2 mL) was added cyclohexane carboxaldehyde (36 μL; 1.5 eq) and sodium triacetoxyborohydride (67 g; 1.5 eq). The reaction was stirred at room temperature under nitrogen. After 18 hours, trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 40% acetonitrile in water containing 0.1% trifluoroacetic acid. The product was obtained as the trifluoroacetic acid salt and was lyophilized to give COMPOUND 16 (52 mg, 30% yield) as a colourless solid. Purity (HPLC): >99%; Optical purity (Chiral HPLC): >99%; $^1$H NMR (400 MHz, CD$_3$OD) 0.95-1.10 (m, 5H), 1.15-1.30 (m, 6H), 1.55-1.70 (m, 2H), 1.71-1.83 (m, 4H), 2.58-2.67 (m, 4H), 3.07 (d, J=6.93 Hz, 2H), 3.17-3.26 (m, 6H), 3.45-3.55 (m, 2H), 4.47 (s, 1H), 6.98-7.03 (m, 1H), 7.22-7.26 (m, 2H), 7.28-7.35 (m, 3H), 7.53 (d, J=8.10 Hz, 2H). Found: C, 52.34; H, 5.82; N, 7.13. C$_{29}$H$_{42}$N$_4$O×0.7H$_2$O×2.8CF$_3$COOH has C, 52.30; H, 5.82; N, 7.13%. [a]$_D^{20}$=+4.07 deg [c 0.639, MeOH].

Compound 17: 4-[(R)-{3-[(cyclohex-1-en-1-ylmethyl)amino]phenyl}(piperazin-1-yl)methyl]-N,N-diethylbenzamide

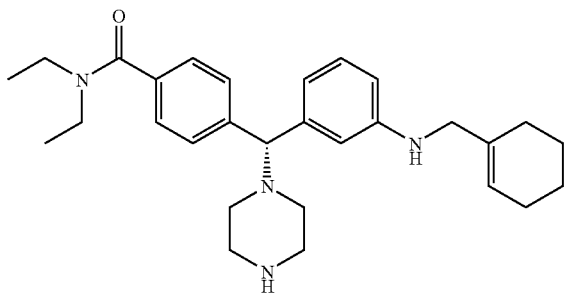

To a solution of INTERMEDIATE 5b (60 mg) in Methanol (2 mL) was added 1-cyclohexene carboxaldehyde (15 mg; 1.1 eq) and decaborane (5 g; 0.3 eq). The reaction was stirred at room temperature under nitrogen. After 18 hours, the solvent was evaporated and the crude product dissolved in dichloromethane and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 12% to 35% acetonitrile in water containing 0.1% trifluoroacetic acid. The product was obtained as the trifluoroacetic acid salt and was lyophilized to give COMPOUND 17 (25 mg, 24% yield) as a colourless solid. Purity (HPLC): >99%; Optical purity (Chiral HPLC): >99%; $^1$H NMR (400 MHz, CD$_3$OD) 1.06 (t, J=5.57 Hz, 3H), 1.19 (t, J=6.64 Hz, 3H), 1.48-1.55 (m, 2H), 1.55-1.63 (m, 2H), 1.89-2.00 (m, 4H), 2.56-2.66 (m, 4H), 3.17-3.25 (m, 6H), 3.39-3.53 (m, 2H), 3.68 (br s, 2H), 4.42 (s, 1H), 5.56 (br s, 1H), 6.83-6.88 (m, 1H), 7.08-7.13 (m, 2H), 7.23 (t, J=8.01 Hz, 1H), 7.30 (d, J=8.45 Hz, 2H), 7.53 (d, J=8.15 Hz, 2H). Found: C, 52.18; H, 5.37; N, 7.41. $C_{29}H_{40}N_4O \times 0.5H_2O \times 2.9CF_3COOH$ has C, 52.23; H, 5.53; N, 7.00%. $[a]_D^{20}$=−4.25 deg [c 0.870, MeOH].

Compound 18: N,N-diethyl-4-[(S)-{3-[methyl(phenyl)amino]phenyl}piperazin-1-yl)methyl]benzamide

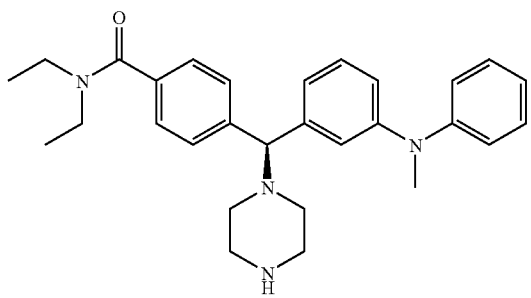

To a solution of INTERMEDIATE 6a (225 mg) in methanol (3 mL) was added formaldehyde (67 μL; 2 eq) and decaborane (15 g; 0.3 eq). The reaction was stirred at room temperature under nitrogen and after 30 min the solution was concentrated. The residue was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated. The residue was purified by purified by flash chromatography on silica gel, eluting 1% NH$_4$OH 5% MeOH in dichloromethane. The pure product was obtained and dissolved in dichloromethane in which 650 μL of 1M HCl in ether was added. Solvent was removed and the product was isolated as the hydrochloride salt to give COMPOUND 18 (99 mg, 52% yield) as a colourless solid. Purity (HPLC): >99%; Optical purity (Chiral BPLC): >99%; $^1$H NMR (400 MHz, d$_6$-DMSO) 1.00-1.16 (m, 6H), 2.25-2.37 (m, 4H), 2.76-2.86 (m, 4H), 3.10-3.22 (m, 2H), 3.24 (s, 3H), 3.35-3.43 (m, 2H), 4.30 (s, 1H), 6.83-6.86 (m, 1H), 6.63-7.00 (m, 4H), 7.10 (br s, 1H), 7.20 (t, J=7.81 Hz, 1H), 7.24-7.29 (m, 4H), 7.41 (d, J=8.01 Hz, 2H) $[a]_D^{20}$=+0.97 deg [c 0.310, MeOH].

Compound 19: N,N-diethyl-4-[(S)-{3-[ethyl(phenyl)amino]phenyl}(piperazin-1-yl)methyl]benzamide

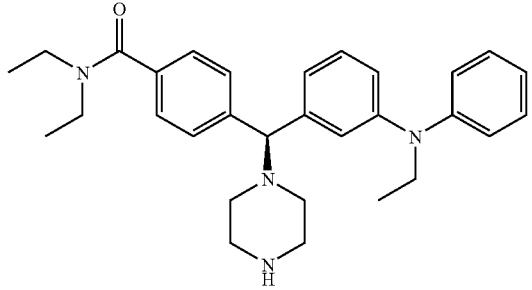

To a solution of INTERMEDIATE 6a (170 mg) in methanol (3 mL) was added acetaldehyde (3-4 mL) and decaborane (11 g; 0.3 eq). The reaction was stirred at 0° C. and after 6 hours the solution was concentrated. The residue was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated. The residue was purified by purified by flash chromatography on silica gel, eluting 1% NH$_4$OH 5% MeOH in dichloromethane. The pure product was obtained and dissolved in dichloromethane in which 650 μL of 1M HCl in ether was added. Solvent was removed and the product was isolated as the hydrochloride salt to give COMPOUND 19 (121 mg, 74% yield) as a colourless solid. Purity (HPLC): >99%; Optical purity (Chiral HPLC): >99%; $^1$H NMR (400 Mz, CD$_3$OD) 1.07 (t, J=6.86 Hz, 3H), 1.12 (t, J=7.15 Hz, 3H), 1.19 (t, J=6.86 Hz, 3H), 2.32-2.43 (m, 4H), 2.80-2.87 (m, 4H), 3.20-3.26 (m, 2H), 3.45-3.52 (m, 2H), 3.73 (q, J=6.86 Hz, 2H), 4.19 (s, 1H), 6.75 (ddd, J=8.13, 2.47, 0.93 Hz, 1H), 6.87-6.90 (m, 1H), 6.91-6.95 (m, 3H), 7.03 (t, J=1.96 Hz, 1H), 7.11 (t, J=7.96 Hz, 1H), 7.19-7.23 (m, 2H), 7.26 d, J=8.28 Hz, 2H), 7.45 (d, J=8.50 Hz, 2H).

Compound 20: N,N-diethyl-4-[(R)-{3-[methyl(phenyl)amino]phenyl}(piperazin-1-yl)methyl]benzamide

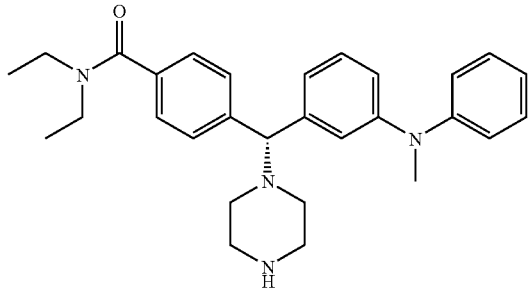

To a solution of INTERMEDIATE 6b (170 mg)) in methanol (3 mL) was added formaldehyde (45 μL; 2 eq) and decaborane (11 g; 0.3 eq). The reaction was stirred at room temperature under nitrogen and after 30 min the solution was concentrated. The residue was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated. The residue was purified by purified by flash chromatography on silica gel, eluting 1% $NH_4OH$ 5% MeOH in dichloromethane. The pure product was obtained and dissolved in dichloromethane in which 200 μL of 1M HCl in ether was added. Solvent was removed and the product was isolated as the hydrochloride salt to give COMPOUND 20 (129 mg, 80% yield) as a colourless solid. Purity (HPLC): >99%; Optical purity (Chiral HPLC): >99%; $^1$H NMR (400 MHz, $d_6$-DMSO) 1.00-1.16 (m, 6H), 2.25-2.37 (m, 4H), 2.76-2.86 (m, 4H), 3.10-3.22 (m, 2H), 3.24 (s, 3H), 3.35-3.43 (m, 2H), 4.30 (s, 1H), 6.83-6.86 (m, 1H), 6.63-7.00 (m, 4H), 7.10 (br s, 1H), 7.20 (t, J=7.81 Hz, 1H), 7.24-7.29 (m, 4H), 7.41 (d, J=8.01 Hz, 2H) $[a]_D^{20}$=+2.31 deg [c 0.368, MeOH].

Compound 21: N,N-diethyl-4-[(R)-{3-[ethyl(phenyl)amino]phenyl}(piperazin-1-yl)methyl]benzamide

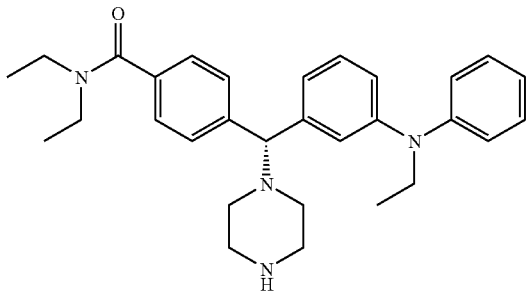

To a solution of INTERMEDIATE 6b (171 mg) in methanol (3 mL) was added acetaldehyde (3-4 mL) and decaborane (11 g; 0.3 eq). The reaction was stirred at 0° C. and after 6 hours the solution was concentrated. The residue was diluted with dichloromethane and washed with saturated aqueous sodium bicarbonate. The aqueous was extracted with two portions of dichloromethane and the combined organics were dried over anhydrous sodium sulfate, filtered and concentrated. The residue was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated. The residue was purified by purified by flash chromatography on silica gel, eluting 1% $NH_4OH$ 5% MeOH in dichloromethane. The pure product was obtained and dissolved in dichloromethane in which 650 μL of 1M HCl in ether was added. Solvent was removed and the product was isolated as the hydrochloride salt to give COMPOUND 21 (155 mg, 81% yield) as a colourless solid. Purity (HPLC): >99%; Optical purity (Chiral HPLC): >99%; $^1$H NMR (400 MHz, $CD_3OD$) 1.07 (t, J=6.86 Hz, 3H), 1.12 (t, J=7.15 Hz, 3H), 1.19 (t, J=6.86 Hz, 3H), 2.32-2.43 (m, 4H), 2.80-2.87 (m, 4H), 3.20-3.26 (m, 2H), 3.45-3.52 (m, 2H), 3.73 (q, J=6.86 Hz, 2H), 4.19 (s, 1H), 6.75 (ddd, J=8.13, 2.47, 0.93 Hz, 1H), 6.87-6.90 (m, 1H), 6.91-6.95 (m, 3H), 7.03 (t, J=1.96 Hz, 1H), 7.11 (t, J=7.96 Hz, 1H), 7.19-7.23 (m, 2H), 7.26 d, J=8.28 Hz, 2H), 7.45 (d, J=8.50 Hz, 2H).

Compound 22: 4-[(R)-{3-[(cyclohexylmethyl)amino]phenyl}(piperazin-1-yl)methyl]-N,N-diethylbenzamide

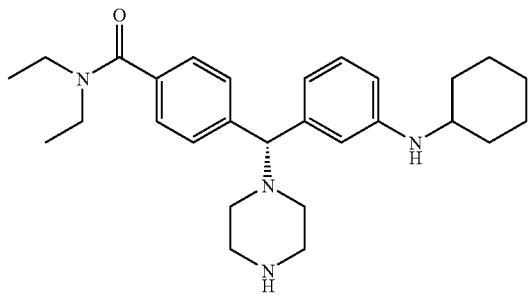

To a solution of INTERMEDIATE 5b (106 mg) in 1,2-dichloroethane (2 mL) was added cyclohexanone (35 μL; 1.5 eq) and sodium triacetoxyborohydride (72 g; 1.5 eq). The reaction was stirred at room temperature under nitrogen. After 18 hours, the reaction was concentrated and diluted with dichloromethane, washed with saturated aqueous sodium bicarbonate and concentrated. The product was purified on silica gel eluting 30% acetone in hexane and pure fractions collected were concentrated. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 12% to 45% acetonitrile in water containing 0.1% trifluoroacetic acid. The product was obtained as the trifluoroacetic acid salt and was lyophilized to give COMPOUND 22 (41 mg, 23% yield) as a colourless solid. Purity (HPLC): >99%; Optical purity (Chiral HPLC): >99%; $^1$H NMR (400 MHz, $CD_3OD$) 1.06 (t, J=7.42 Hz, 3H), 1.19 (t, J=6.93 Hz, 3H), 1.22-1.39 (m, 5H), 1.62-1.69 (m, 1H), 1.76-1.83 (m, 2H), 1.84-1.94 (m, 2H), 2.58-2.67 (m, 4H), 3.17-3.26 (m, 6H), 3.32-3.39 (m, 1H), 3.45-3.52 (m, 2H), 4.54 (s, 1H), 7.14 (ddd, J=7.61, 2.18, 1.16 Hz, 1H), 7.32 (d, J=8.44 Hz, 2H), 7.43 (t, J=7.66 Hz, 2H), 7.45-7.49 (m, 1H), 7.53 (d, J=8.19 Hz). Found: C, 54.10; H, 6.13; N, 7.77. $C_{28}H_{40}N_4O \times 0.7H_2O \times 2.3CF_3COOH$ has C, 54.12; H, 6.09; N, 7.74%. $[a]_D^{20}$=−6.39 deg [c 0.939, MeOH].

Compound 23: 4-[(R)-[3-(cyclopentylamino)phenyl](piperazin-1-yl)methyl]-N,N-diethylbenzamide

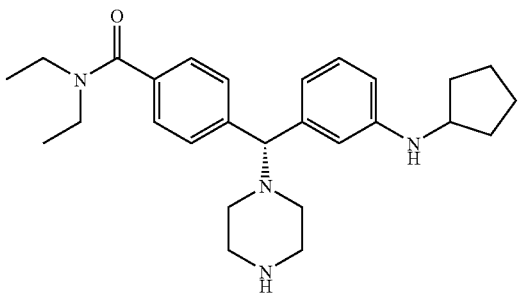

To a solution of INTERMEDIATE 5b (116 mg) in methanol (3 mL) was added cyclopentanone (24 μL; 1.1 eq) and decaborane (10 g; 0.3 eq). The reaction was stirred at room temperature under nitrogen. After 18 hours, the solvent was evaporated and the crude product dissolved in dichloromethane and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 35% acetonitrile in water containing 0.1% trifluoroacetic acid. The product was obtained as the trifluoroacetic acid salt and was lyophilized to give COMPOUND 23 (70 mg, 36% yield) as a colourless solid. Purity (HPLC): >99%; Optical purity (Chiral HPLC): >99%; $^1$H NMR (400 MHz, CD$_3$OD) 1.06 (t, J=6.64 Hz, 3H), 1.19 (t, J=6.74 Hz, 3H), 1.60-1.66 (m, 4H), 1.74-1.80 (m, 2H), 1.90-1.96 (m, 2H), 2.60-2.66 (m, 4H), 3.18-3.27 (m, 6H), 3.45-3.52 (m, 2H), 3.81-3.92 (m, 1H), 4.54 (s, 1H), 7.14 (dt, J=7.32, 1.90 Hz, 1H), 7.31 (d, J=8.40 Hz, 2H), 7.38-7.46 (m, 3H), 7.53, (d, J=8.20 Hz, 2H). Found: C, 52.17; H, 5.68; N, 7.63. $C_{27}H_{38}N_4O \times 0.6H_2O \times 2.6CF_3COOH$ has C, 53.13; H, 5.68; N, 7.55%. $[a]_D^{20}$=7.44 deg [c 0.806, MeOH].

Compound 24: 4-[(R)-[3-(cycloheptylamino)phenyl](piperazin-1-yl)methyl]-N,N-diethylbenzamide

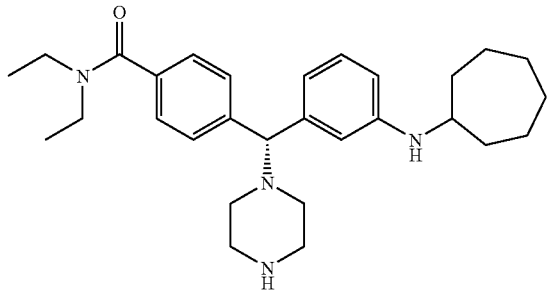

To a solution of INTERMEDIATE 5b (95 mg) in methanol (3 mL) was added cycloheptanone (26 μL; 1.1 eq) and decaborane (7.4 g; 0.3 eq). The reaction was stirred at room temperature under nitrogen. After 18 hours, the solvent was evaporated and the crude product dissolved in dichloromethane and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 35% acetonitrile in water containing 0.1% trifluoroacetic acid. The product was obtained as the trifluoroacetic acid salt and was lyophilized to give COMPOUND 24 (55 mg, 34% yield) as a colourless solid. Purity (HPLC): >99%; Optical purity (Chiral HPLC): >99%; $^1$H NMR (400 MHz, CD$_3$OD) 1.06 (t, J=6.54 Hz, 3H), 1.19 (t, J=6.64 Hz, 3H), 1.40-1.49 (m, 2H), 1.53-1.63 (m, 6H), 1.65-1.75 (m, 2H), 1.89-1.97 (m, 2H), 2.60-2.66 (m, 4H), 3.18-3.26 (m, 6H), 3.45-3.52 (m, 2H), 3.52-3.59 (m, 1H), 4.54 (s, 1H), 7.13 (dt, J=7.37, 1.68 Hz, 1H), 7.31 (d, J=8.40 Hz, 2H), 7.38-7.47 (m, 3H), 7.53 (d, J=8.20 Hz, 2H). Found: C, 54.35; H, 5.98; N, 7.57. $C_{29}H_{42}N_4O \times 0.2H_2O \times 2.5CF_3COOH$ has C, 54.35; H, 6.02; N, 7.46%. $[a]_D^{20}$=−7.70 deg [c 0.649, MeOH].

Compound 25: 4-[(R)-[3-(cyclooctylamino)phenyl](piperazin-1-yl)methyl]-N,N-diethylbenzamide

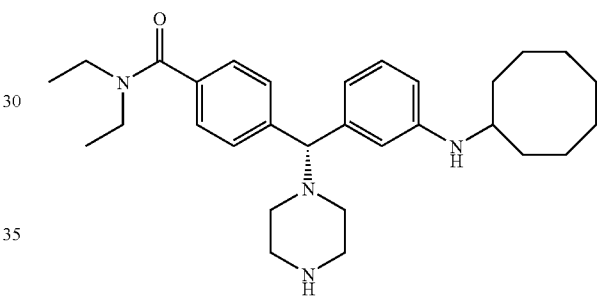

To a solution of INTERMEDIATE 5b (148 mg) in methanol (3 mL) was added cyclooctanone (48 g; 1.2 eq) and decaborane (11 g; 0.3 eq). The reaction was stirred at room temperature under nitrogen. After 18 hours, the solvent was evaporated and the crude product dissolved in dichloromethane and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 15% to 35% acetonitrile in water containing 0.1% trifluoroacetic acid. The product was obtained as the trifluoroacetic acid salt and was lyophilized to give COMPOUND 25 (88 mg, 34% yield) as a colourless solid. Purity (HPLC): >99%; Optical purity (Chiral HPLC): >99%; $^1$H NNIR (400MHz, CD$_3$0D) 1.06 (t, J=6.74Hz, 3H), 1.19 (t, J=6.69 Hz, 3H), 1.40-1.52 (m, 3H), 1.52-1.60 (m, 4H), 1.60-1.76 (m, 5H), 180-190 (m, 2H), 2.58-2.66 (m, 4H), 3.18-3.25 (m, 6H), 3.45-3.53 (m, 2H), 3.61-3.66 (m, 1H), 4.56 (s, 1H), 7.20 (ddd, J=7.81, 2.15, 0.98 Hz, 1H), 7.32 (d, J=8.47 Hz, 2H), 7.45 (t, J=7.81 Hz, 2H), 7.49 (br s, 1H), 7.51-7.55 (m, 3H). Found: C, 54.26; H, 6.10; N, 7.24. $C_{30}H_{40}N_4O \times 0.3H_2O \times 2.6CF_3COOH$ has C, 54.30; H, 6.11; N, 7.20%. $[a]_D^{20}$=−8.86 deg [c 0.700, MeOH].

Compound 26: 4-[(R)-[3-(cyclononylamino)phenyl](piperazin-1-yl)methyl]-N,N-diethylbenzamide

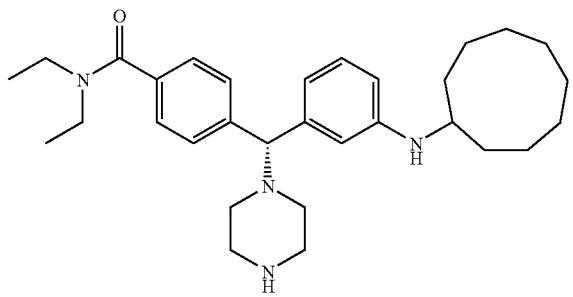

To a solution of INTERMEDIATE 5b (106 mg) in methanol (3 mL) was added cyclononanone (40 µL; 1.2 eq) and decaborane (8 g; 0.3 eq). The reaction was stirred at room temperature under nitrogen. After 18 hours, the reaction was concentrated and diluted with dichloromethane, washed with saturated aqueous sodium bicarbonate and concentrated. The product was purified on silica gel eluting 35% acetone in hexane and pure fractions collected were concentrated. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 15% to 35% acetonitrile in water containing 0.1% trifluoroacetic acid. The product was obtained as the trifluoroacetic acid salt and was lyophilized to give COMPOUND 26 (64 mg, 34% yield) as a colourless solid. Purity (HPLC): >99%; Optical purity (Chiral HPLC): >99%; $^1$H NMR (400 MHz, CD$_3$OD) 1.00-1.10 (m, 3H), 1.15-1.23 (m, 3H), 1.31-1.45 (m, 4H), 1.45-1.55 (m, 6H), 1.55-1.68 (m, 2H), 1.70-1.83 (m, 4H), 2.55-2.70 (m, 4H), 3.15-3.25 (m, 6H), 3.43-3.54 (m, 2H), 3.63-3.70 (m, 1H), 4.56 (s, 1H), 7.18-7.25 (m, 1H), 7.28-7.34 (m, 2H), 7.45-7.50 (m, 1H), 7.51-7.56 (m, 4H). Found: C, 54.34; H, 6.29; N, 7.06. C$_{31}$H$_{46}$N$_4$O×0.7H$_2$O×2.6CF$_3$COOH has C, 54.36; H, 6.30; N, 7.01%. [a]$_D^{20}$=−10.40 deg [c 0.625, MeOH].

COMPOUND 27: 4-[(S)-[3-(cyclohexylamino)phenyl](piperazin-1-yl)methyl]-N,N-diethylbenzamide

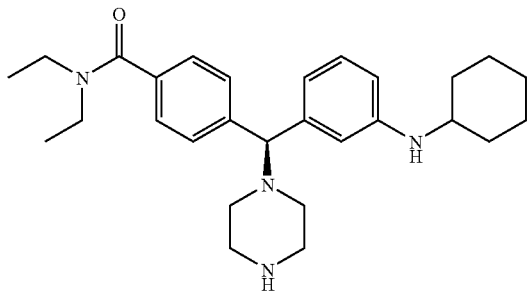

To a solution of INTERMEDIATE 5a (94 mg) in methanol (3 mL) was added cyclohexanone (23 µL; 1.1 eq) and decaborane (7.4 g; 0.3 eq). The reaction was stirred at room temperature under nitrogen. After 18 hours, the solvent was evaporated and the crude product dissolved in dichloromethane and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 12% to 40% acetonitrile in water containing 0.1% trifluoroacetic acid. The product was obtained as the trifluoroacetic acid salt and was lyophilized to give COMPOUND 27 (74 mg, 46% yield) as a colourless solid. Purity (HPLC): >99%; Optical purity (Chiral HPLC): >99%; $^1$H NMR (400 MHz, CD$_3$OD) 1.06 (t, J=7.42 Hz, 3H), 1.19 (t, J=6.93 Hz, 3H), 1.22-1.39 (m, 5H), 1.62-1.69 (m, 1H), 1.76-1.83 (m, 2H), 1.84-1.94 (m, 2H), 2.58-2.67 (m, 4H), 3.17-3.26 (m, 6H), 3.32-3.39 (m, 1H), 3.45-3.52 (m, 2H), 4.55 (s, 1H), 7.14 (ddd, J=7.61, 2.18, 1.16 Hz, 1H), 7.32 (d, J=8.44 Hz, 2H), 7.43 (t, J=7.66 Hz, 2H), 7.45-7.49 (m, 1H), 7.53 (d, J=8.19 Hz, 2H). Found: C, 53.79; H, 5.91; N, 7.66. C$_{28}$H$_{40}$N$_4$O×0.2H$_2$O×2.5CF$_3$COOH has C, 53.76; H, 5.86; N, 7.60%. [a]$_D^{20}$=+7.44 deg [c 0.632, MeOH].

COMPOUND 28: N,N-diethyl-4-[(R)-{3-[(4-methylphenyl)amino]phenyl}(piperazin-1-yl)methyl]benzamide

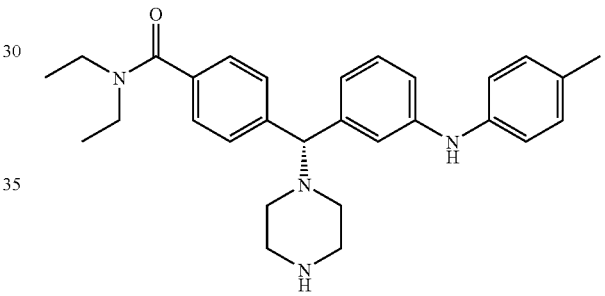

To a solution of INTERMEDIATE 5b (108 mg) in toluene (2 mL) was added 4-bromo toluene (51 g; 1.3 eq), Pd$_2$(dba)$_3$ (25 g; 0.04 eq), Sodium tert-butoxide (93 g; 1.4 eq) and BINAP (34 g; 0.08 eq). The solution was heated in the microwave in a sealed tube for 5 min at 110° C. The resulting mixture filtered through celite and concentrated. The crude was purified by a normal phase MPLC with a disposable silica gel column (40 g); eluting 40% to 60% ethyl acetate in hexane. Pure fraction collected and concentrated to afford yellow foam. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated to about 2 mL of solvent. In the solution was added 475 µL of 1M HCl in ether and the solvent were removed and the product was isolated as the hydrochloride salt to give COMPOUND 28 (62 mg, 59% yield) as beige solid. Purity (HPLC): >99%; Optical purity (Chiral HPLC): >99%; $^1$H NMR (400 MHz, CD$_3$OD) 1.07 (t, J=6.88 Hz, 3H), 1.20 (t, J=6.83 Hz, 3H), 2.24 (s, 3H), 3.00-3.16 (m, 3H), 3.18-3.26 (m, 3H), 3.42-3.53 (m, 6H), 6.91 (br s, 1H), 6.93 (d, J=8.30 Hz, 2H), 7.00 (br s, 1H), 7.04 (d, J=8.29 Hz, 2H), 7.18 (t, J=7.91 Hz, 1H), 7.22 (br s, 1H), 7.39 (d, J=7.91 Hz, 2H), 7.72 (d, J=7.22 Hz, 2H). Found: C, 62.07; H, 6.92; N, 9.42. $C_{29}H_{36}N_4O\times2.9HCl\times0.3C_4H_{10}O$ has C, 62.05; H, 7.22 N, 9.58%. $[\alpha]_D^{20}$=−4.04 deg [c 0.339, MeOH].

COMPOUND 29: N,N-diethyl-4-[(S)-{3-[(4-methylphenyl)amino]phenyl}(piperazin-1-yl)methyl]benzamide

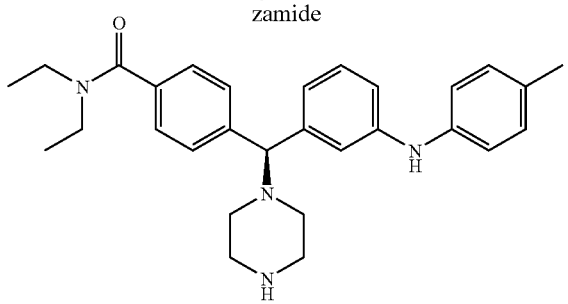

To a solution of INTERMEDIATE 5a (101 mg) in toluene (2 mL) was added 4-bromo toluene (48 g; 1.3 eq), $Pd_2(dba)_3$ (8.2 g; 0.04 eq), Sodium tert-butoxide (29 g; 1.4 eq) and BINAP (11 g; 0.08 eq). The solution was heated in the microwave in a sealed tube for 5 min at 110° C. The resulting mixture filtered through celite and concentrated. The crude was purified by a normal phase MPLC with a disposable silica gel column (40 g); eluting 40% to 60% ethyl acetate in hexane. Pure fraction collected and concentrated to afford yellow foam. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated to about 2 mL of solvent. In the solution was added 490 μL of 1M HCl in ether and the solvent was removed and the product was isolated as the hydrochloride salt to give COMPOUND 29 (67 mg, 68% yield) as beige solid. Purity (HPLC): >99%; Optical purity (Chiral HPLC): >99%; $^1$H NMR (400 MHz, $CD_3OD$) 1.07 (t, J=6.88 Hz, 3H), 1.20 (t, J=6.83 Hz, 3H), 2.24 (s, 3H), 3.00-3.16 (m, 3H), 3.18-3.26 (m, 3H), 3.42-3.53 (m, 6H), 6.91 (br s, 1H), 6.93 (d, J=8.30 Hz, 2H), 7.00 (br s, 1H), 7.04 (d, J=8.29 Hz, 2H), 7.18 (t, J=7.91 Hz, 1H), 7.22 (br s, 1H), 7.39 (d, J=7.91 Hz, 2H), 7.72 (d, J=7.22 Hz, 2H). Found: C, 61.50; H, 6.97; N, 9.43. $C_{29}H_{36}N_4O\times0.1H_2O\times3.0HCl$ $0.3C_4H_{10}O$ has C, 61.47; H, 7.21; N, 9.50%. $[\alpha]_D^{20}$=+3.03 deg [c 0.343, MeOH].

COMPOUND 30: 4-[(R)-{3-[(3-chlorophenyl)amino]phenyl}(piperazin-1-yl)methyl]-N,N-diethylbenzamide

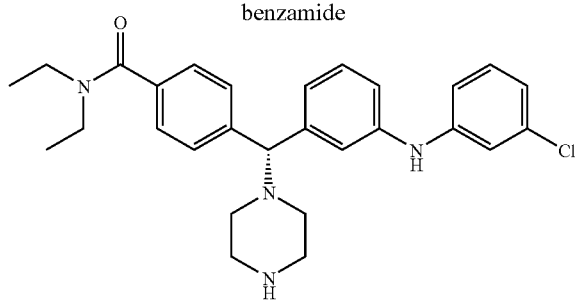

To a solution of INTERMEDIATE 5b (108 mg) in toluene (2 mL) was added 3-chloro-bromobenzene (35 μL; 1.3 eq), $Pd_2(dba)_3$ (8.2 g; 0.04 eq), Sodium tert-butoxide (31 g; 1.4 eq) and BINAP (11 g; 0.08 eq). The solution was heated in the microwave in a sealed tube for 5 min at 110° C. The resulting mixture filtered through celite and concentrated. The crude was purified by a normal phase MPLC with a disposable silica gel column (40 g); eluting 40% to 60% ethyl acetate in hexane. Pure fraction collected and concentrated to afford yellow foam. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated to about 2 mL of solvent. In the solution was added 560 μL of 1M HCl in ether and the solvent was removed and the product was isolated as the hydrochloride salt to give COMPOUND 30 (77 mg, 70% yield) as beige solid. Purity (HPLC): >99%; Optical purity (Chiral HPLC): >99%; $^1$H NMR (400 MHz, $CD_3OD$) 1.07 (t, J=6.40 Hz, 3H), 1.20 (t, J=6.64 Hz, 3H), 3.05-3.27 (m, 6H), 3.43-3.57 (m, 6H), 6.80 (dd, J=8.01, 1.27 Hz, 1H), 6.92 (dd, J=8.15, 1.51 Hz, 1H), 6.99 (t, J=2.00 Hz, 1H), 7.00-7.04 (m, 1H), 7.13-7.17 (m, 2H), 7.27 (t, J=7.76 Hz, 1H), 7.39 (br s, 1H), 7.41 (d, J=7.81 Hz, 2H), 7.75 (d, J=6.74 Hz, 2H). Found: C, 58.16; H, 6.39; N, 9.10. $C_{28}H_{33}N_4OCl\times2.9HCl\times0.40C_4H_{10}O$ has C, 58.05; H, 6.57; N, 9.15%. $[\alpha]_D^{20}$=−17.37 deg [c 0.499, MeOH].

COMPOUND 31: 4-[(S)-{3-[(3-chlorophenyl)amino]phenyl}(piperazin-1-yl)methyl]-N,N-diethylbenzamide

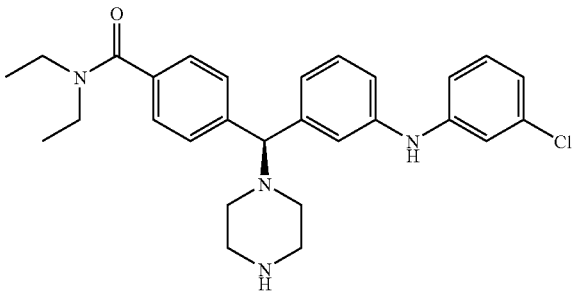

To a solution of INTERMEDIATE 5a (103 mg) in toluene (2 mL) was added 3-chloro-bromobenzene (34 μL; 1.3 eq), $Pd_2(dba)_3$ (8.2 g; 0.04 eq), Sodium tert-butoxide (29 g; 1.4 eq) and BINAP (11 g; 0.08 eq). The solution was heated in the microwave in a sealed tube for 5 min at 110° C. The resulting mixture filtered through celite and concentrated. The crude was purified by a normal phase MPLC with a disposable silica gel column (40 g); eluting 40% to 60% ethyl acetate in hexane. Pure fraction collected and concentrated to afford yellow foam. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated to about 2 mL of solvent. In the solution was added 560 μL of 1M HCl in ether and the solvent was removed and the product was isolated as the hydrochloride salt to give COMPOUND 30 (77 mg, 73% yield) as beige solid. Purity (HPLC): >99%; Optical purity (Chiral HPLC): >99%; $^1$H NMR (400 MHz, $CD_3OD$) 1.07 (t, J=6.40 Hz, 3H), 1.20 (t, J=6.64 Hz, 3H), 3.05-3.27 (m, 6H), 3.43-3.57 (m, 6H), 6.80 (dd, J=8.01, 1.27 Hz, 1H), 6.92

(dd, J=8.15, 1.51 Hz, 1H), 6.99 (t, J=2.00 Hz, 1H), 7.00-7.04 (m, 1H), 7.13-7.17 (m, 2H), 7.27 (t, J=7.76 Hz, 1H), 7.39 (br s, 1H), 7.41 (d, J=7.81 Hz, 2H), 7.75 (d, J=6.74 Hz, 2H). $[\alpha]_D^{20}$=+20.77 deg [c 0.467, MeOH].

COMPOUND 32: 4-[(R)-{3-[(2-fluorophenyl) amino]phenyl}(piperazin-1-yl)methyl]-N,N-diethyl-benzamide

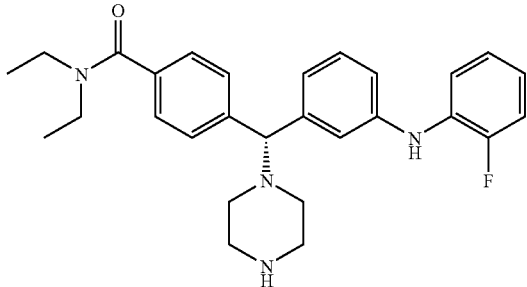

To a solution of INTERMEDIATE 5b (131 mg) in toluene (2 mL) was added 2-fluoro-bromobenzene (40 µL; 1.3 eq), Pd$_2$(dba)$_3$ (10 g; 0.04 eq), Sodium tert-butoxide (37 g; 1.4 eq) and BINAP (13 g; 0.08 eq). The solution was heated in the microwave in a sealed tube for 5 min at 110° C. The resulting mixture filtered through celite and concentrated. The crude was purified by a normal phase MPLC with a disposable silica gel column (40 g); eluting 40% to 60% ethyl acetate in hexane. Pure fraction collected and concentrated to afford yellow foam. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated to about 2 mL of solvent. In the solution was added 631 µL of 1M HCl in ether and the solvent was removed and the product was isolated as the hydrochloride salt to give COMPOUND 32 (83 mg, 64% yield) as beige solid. Purity (HPLC): >99%; Optical purity (Chiral HPLC): >99%; $^1$H NMR (400 MHz, CD$_3$OD) 1.07 (t, J=6.25 Hz, 3H), 1.20 (t, J=7.08 Hz, 3H), 3.05-3.17 (m, 2H), 3.18-3.25 (m, 4H), 3.40-3.55 (m, 6H), 6.87-6.96 (m, 2H), 7.01-7.06 (m, 1H), 7.06-7.14 (m, 2H), 1.18-7.25 (m, 3H), 7.40 (d, J=7.81 Hz, 2H), 7.74 (d, J=7.13 Hz, 2H). Found: C, 59.59; H, 6.56; N, 9.29. $C_{28}H_{33}FN_4O\times2.9HCl\times0.4C_4H_{10}O$ has C, 59.65; H, 6.75; N, 9.40%. $[\alpha]_D^{20}$=+2.59 deg [c 0.617, MeOH].

COMPOUND 33: 4-[(S)-{3-[(2-fluorophenyl) amino]phenyl}(piperazin-1-yl)methyl]-N,N-diethyl-benzamide

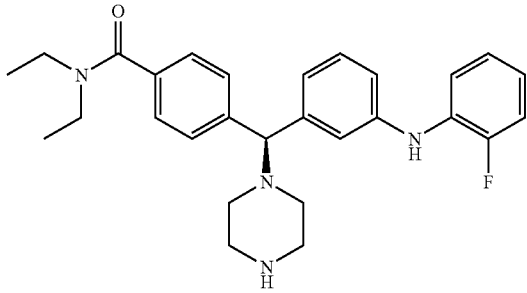

To a solution of INTERMEDIATE 5a (99 mg) in toluene (2 mL) was added 2-fluoro-bromobenzene (30 µL; 1.3 eq), Pd$_2$(dba)$_3$ (7 g; 0.04 eq), Sodium tert-butoxide (28 g; 1.4 eq) and BINAP (11 g; 0.08 eq). The solution was heated in the microwave in a sealed tube for 5 min at 110° C. The resulting mixture filtered through celite and concentrated. The crude was purified by a normal phase MPLC with a disposable silica gel column (40 g); eluting 40% to 60% ethyl acetate in hexane. Pure fraction collected and concentrated to afford yellow foam. The resulting product was dissolved in dichloromethane (5 mL) and trifluoroacetic acid (0.5 mL) was added and the solution stirred for 18 hours until complete removal of the boc group. The reaction was concentrated and diluted with dichloromethane, washed with saturated aqueous sodium bicarbonate. The aqueous was extracted with two portions of dichloromethane and the combined organics were dried over anhydrous sodium sulfate, filtered and concentrated to about 2 mL of solvent. In the solution was added 460 µL of 1M HCl in ether and the solvent was removed and the product was isolated as the hydrochloride salt to give COMPOUND 33 (61 mg, 63% yield) as beige solid. Purity (HPLC): >99%; Optical purity (Chiral HPLC): >99%; $^1$H NMR (400 MHz, CD$_3$OD) 1.07 (t, J=6.25 Hz, 3H), 1.20 (t, J=7.08 Hz, 3H), 3.05-3.17 (m, 2H), 3.18-3.25 (m, 4H), 3.40-3.55 (m, 6H), 6.87-6.96 (m, 2H), 7.01-7.06 (m, 1H), 7.06-7.14 (m, 2H), 1.18-7.25 (m, 3H), 7.40 (d, J=7.81 Hz, 2H), 7.74 (d, J=7.13 Hz, 2H). Found: C, 59.14; H, 6.51; N, 9.41. $C_{29}H_{42}N_4O\times3.0HCl\times0.3C_4H_{10}O$ has C, 59.22; H, 6.64; N, 9.46%. $[\alpha]_D^{20}$=+4.26 deg [c 0.329, MeOH].

COMPOUND 34: 4-[(R)-[3-(benzoylamino)phenyl] (piperazin-1-yl)methyl]-N,N-diethylbenzamide

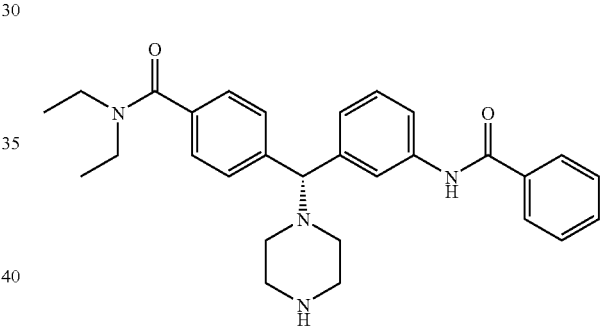

To a solution of INTERMEDIATE 5b (150 mg) in dichloromethane (10 mL) was added benzoic anhydride (80 g; 1.1 eq) and triethylamine (139 µL; 3.1 eq). The reaction was stirred at room temperature under nitrogen. After 18 hours, trifluoroacetic acid (1 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 40% acetonitrile in water containing 0.1% trifluoroacetic acid. The product was obtained as the trifluoroacetic acid salt and was lyophilized to give COMPOUND 34 (110 mg, 49% yield) as a colourless solid. Purity (HPLC): >98%; Optical purity (Chiral HPLC): >99%; $^1$H NMR (400 MHz, CD$_3$OD) 1.08 (t, J=7.27 Hz 3H), 1.21 (t, J=6.62 Hz, 3H), 2.6-2.73 (m, 4H), 3.21-3.28 (m, 6H), 3.46-3.54 (m, 2H), 4.49 (s, 1H), 7.21-7.25 (m, 1H), 7.30 (d, J=8.07 Hz, 1H), 7.34 (d, J=8.57 Hz, 2H), 7.42-7.47 (m, 1H), 7.47-7.53 (m, 3H), 7.55-7.61 (m, 3H), 7.88-7.92 (m, 2H), 7.99-8.02 (m, 1H). Found: C, 57.77; H, 5.61; N, 8.61. $C_{29}H_{34}N_4O_2\times1.6\ CF_3CO_2H\times0.9\ H_2O$ has C, 57.79; H, 5.63; N, 8.37%. $[\alpha]_D^{20}$=-27.83 deg [c 0.873, MeOH].

COMPOUND 35: N,N-diethyl-4-[(R)-{3-[(phenylacetyl)amino]phenyl}(piperazin-1-yl)methyl]benzamide

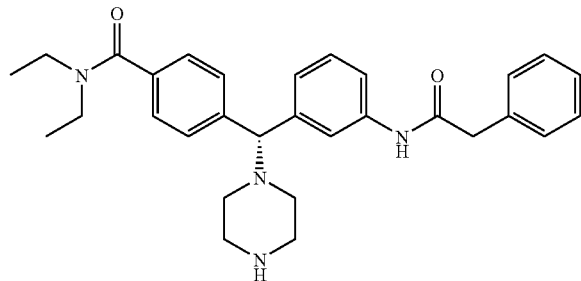

To a solution of INTERMEDIATE 5b (120 mg) in dichloromethane (8 mL) was added phenyl acetylchloride (41 μL; 1.2 eq) and triethylamine (43 μL; 1.2 eq). The reaction was stirred at room temperature under nitrogen. After 18 hours, the trifluoroacetic acid (1 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 40% acetonitrile in water containing 0.1% trifluoroacetic acid. The product was obtained as the trifluoroacetic acid salt and was lyophilized to give COMPOUND 35 (46 mg, 25% yield) as a colourless solid. Purity (HPLC): >99%; Optical purity (Chiral HPLC): >99%; $^1$H NMR (400 MHz, CD$_3$OD) 1.05 (t, J=6.81 Hz, 3H), 1.19 (t, J=6.80 Hz, 3H), 2.50-2.67 (m, 4H), 3.16-3.25 (m, 6H), 3.44-3.52 (m, 2H), 3.63 (s, 2H), 4.41 (s, 1H), 7.12-7.16 (m, 1H), 7.19-7.26 (m, 3H), 7.26-7.33 (m, 6H), 7.52 (d, J=7.85 Hz, 2H), 7.84-7.87 (m, 1H). Found: C, 60.56; H, 6.08; N, 8.65. C$_{30}$H$_{36}$N$_4$O$_2$×2.4 H$_2$O× 0.9 CF$_2$COOH has C, 60.58; H, 6.67; N, 8.89%. [a]$_D^{20}$=−17.21 deg [c 0.825, MeOH].

COMPOUND 36: 4-[(S)-[3-(benzoylamino)phenyl](piperazin-1-yl)methyl]-N,N-diethylbenzamide

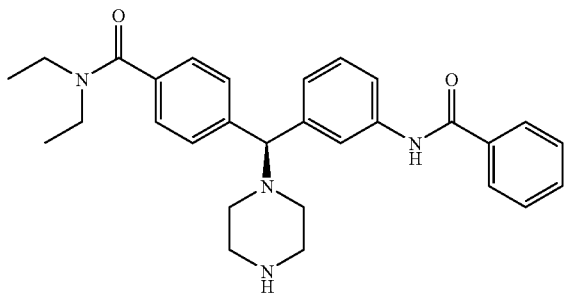

To a solution of INTERMEDIATE 5a (111 mg) in pyridine (3 mL) was added benzoyl chloride (31 g; 1.2 eq). The reaction was stirred at room temperature under nitrogen. After 18 hours, reaction was concentrated and the crude dissolved in dichloromethane and trifluoroacetic acid (1 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 40% acetonitrile in water containing 0.1% trifluoroacetic acid. The product was obtained as the trifluoroacetic acid salt and was lyophilized to give COMPOUND 36 (100 mg, 60% yield) as a colourless solid. Purity (HPLC): >99%; Optical purity (Chiral HPLC): >99%; $^1$H NMR (400 MHz, CD$_3$OD) 1.06 (t, J=6.74 Hz, 3H), 1.19 (t, J=6.74 Hz, 3H), 2.87-2.99 (m, 4H), 3.18-3.25 (m, 2H), 3.36-3.42 (m, 4H), 3.46-3.53 (m, 2H), 7.33-7.38 (m, 4H), 7.46-7.51 (m, 2H), 7.52-7.58 (m, 2H), 7.69 (d, J=8.10 Hz, 2H), 7.88-7.92 (m, 2H), 8.02-8.04 (m, 1H). Found: C, 54.19; H, 5.55; N, 7.85. C$_{29}$H$_{34}$N$_4$O$_2$× 2.2H$_2$O×1.9CF$_3$COOH has C, 54.20; H, 5.59; N, 7.71%. [a]$_D^{20}$=+16.30 deg [c 1.550, MeOH].

COMPOUND 37: N,N-diethyl-4-[(S)-{3-[(phenylacetyl)amino]phenyl}(piperazin-1-yl)methyl]benzamide

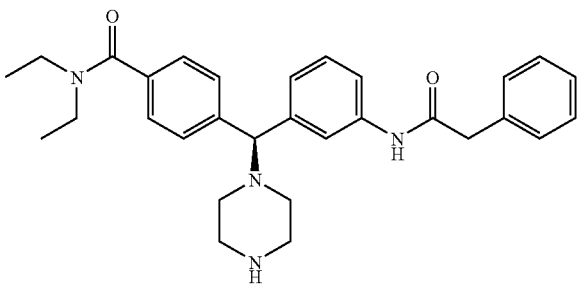

To a solution of INTERMEDIATE 5a (101 mg) in dichloromethane (8 mL) was added phenyl acetylchloride (34 μL; 1.2 eq) and triethylamine (57 μL; 2 eq). The reaction was stirred at room temperature under nitrogen. After 18 hours, the trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 12% to 35% acetonitrile in water containing 0.1% trifluoroacetic acid. The product was obtained as the trifluoroacetic acid salt and was lyophilized to give COMPOUND 37 (67 mg, 43% yield) as a colourless solid. Purity (HPLC): >99%; Optical purity (Chiral HPLC): >99%; $^1$H NMR (400 MHz, CD$_3$OD) 1.05 (t, J=6.74 Hz, 3H), 1.19 (t, J=6.69 Hz, 3H), 2.52-2.65 (m, 4H), 3.17-3.25 (m, 6H), 3.45-3.53 (m, 2H), 3.63 (s, 2H), 4.41 (s, 1H), 7.13 (dt, J=7.03, 1.71 Hz, 1H), 7.19-7.26 (m, 3H), 7.26-7.32 (m, 5H), 7.51 (d, J=8.20 Hz, 2H), 7.85-7.87 (m, 1H). Found: C, 57.21; H, 5.71; N, 7.95. C$_{30}$H$_{36}$N$_4$O$_2$×0.9H$_2$O×1.8CF$_3$COOH has C, 57.15; H, 5.65; N, 7.93%. [a]$_D^{20}$=+21.60 deg [c 0.375, MeOH].

COMPOUND 38: N,N-diethyl-4-[(R)-{3-[(2-methyl-2-phenylpropanoyl)amino]phenyl}(piperazin-1-yl)methyl]benzamide

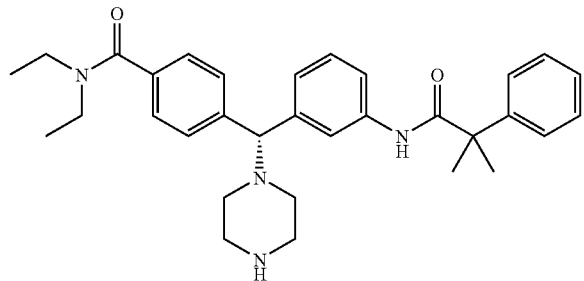

To a solution of INTERMEDIATE 5b (105 mg) in dimethylformamide (4 mL) was added α,α-dimethylphenylacetic acid (74 g; 2 eq), HATU (156 g; 4 eq) and N,N-diisopropylethylamine (173 μL; 4 eq). The reaction was stirred at room temperature under nitrogen. After 18 hours, the reaction was concentrated and the crude dissolved in dichloromethane (5 mL) and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 38 (51 mg, 31% yield) as a colourless solid. Purity (HPLC): >99%; Optical purity (Chiral HPLC): >99%; $^1$H NMR (400 MHz, CD$_3$OD) 1.06 (t, J=7.66 Hz, 3H), 1.19 (t, J=6.92 Hz, 3H), 1.58 (s, 6H), 2.53-2.68 (m, 4H), 3.17-3.25 (m, 6H), 3.44-3.53 (m, 2H), 4.40 (s, 1H), 7.11-7.17 (m, 1H), 7.18-7.24 (m, 3H), 7.29 (d, J=8.34 Hz, 2H), 7.31-7.38 (m, 4H), 7.52 (d, J=8.22 Hz, 2H), 7.71-7.73 (m, 1H). Found: C, 60.46; H, 6.23; N, 8.18. C$_{32}$H$_{40}$N$_4$O$_2$×0.6H$_2$O×1.5CF$_3$COOH has C, 60.53; H, 6.20; N, 8.07%. [a]$_D^{20}$=−8.58 deg [c 0.792, MeOH].

COMPOUND 39: N,N-diethyl-4-[(R)-(3-{[(3-fluorophenyl)acetyl]amino}phenyl)(piperazin-1-yl)methyl]benzamide

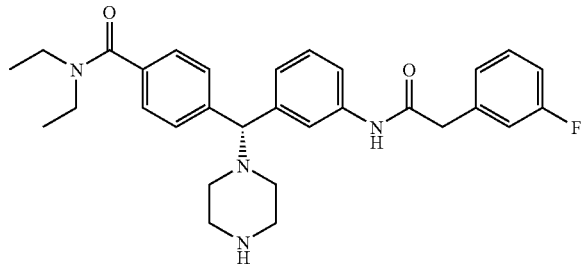

To a solution of INTERMEDIATE 5b (105 mg) in dimethylformamide (4 mL) was added 3-fluoro-phenylacetic acid (76 g; 2 eq), HATU (141 g; 1.5 eq) and N,N-diisopropylethylamine (173 μL; 4 eq). The reaction was stirred at room temperature under nitrogen. After 18 hours, the DMF was concentrated and the crude dissolved in dichloromethane (5 mL) and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 39 (91 mg, 50% yield) as a colourless solid. Purity (HPLC): >99%; Optical purity (Chiral HPLC): >99%; $^1$H NMR (400 MHz, CD$_3$OD) 1.05 (t, J=6.70 Hz, 3H), 1.19 (t, J=6.71 Hz, 3H), 2.50-2.69 (m, 4H), 3.15-3.25 (m, 6H), 3.44-3.53 (m, 2H), 3.65 (s, 2H), 4.41 (s, 1H), 6.96 (td, J=8.59, 2.73 Hz, 1H), 7.05-7.12 (m, 1H), 7.12-7.17 (m, 2H), 7.23 (t, J=7.85 Hz, 1H), 7.25 (t, J=1.80 Hz, 1H), 7.29 (d, J=8.34 Hz, 2H), 7.28-7.34 (m, 1H), 7.52 (d, J=8.34 Hz, 2H), 7.86 (t, J=1.65 Hz, 1H). Found: C, 57.56; H, 5.65; N, 8.21. C$_{30}$H$_{35}$N$_4$O$_2$F×1.2H$_2$O×1.4CF$_3$COOH has C, 57.61; H, 5.72; N, 8.19%. [a]$_D^{20}$=−23.52 deg [c 0.863, MeOH].

COMPOUND 40: 4-[(R)-{3-[(cyclohexylacetyl)amino]phenyl}(piperazin-1-yl)methyl]-N,N-diethylbenzamide

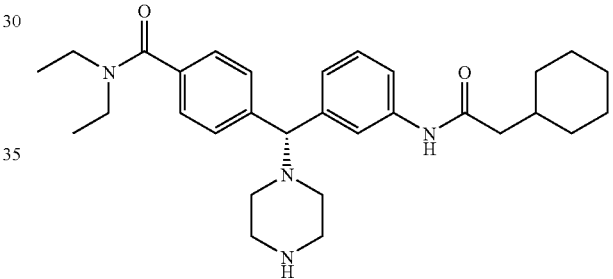

To a solution of INTERMEDIATE 5b (96 mg) in dimethylformamide (4 mL) was added cyclohexylacetic acid (58 g; 2 eq), HATU (117 g; 1.5 eq) and N,N-diisopropylethylamine (143 μL; 4 eq). The reaction was stirred at room temperature under nitrogen. After 18 hours, the reaction was concentrated and the crude dissolved in dichloromethane (5 mL) and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 40 (59 mg, 40% yield) as a colourless solid. Purity (HPLC): >99%; Optical purity (Chiral HPLC): >99%; $^1$H NMR (400 MHz, CD$_3$OD) 0.95-1.03 (m, 2H), 1.03-1.08 (m, 3H), 1.16-1.21 (m, 3H), 1.22-1.32 (m, 2H), 1.61-1.76 (m, 6H), 1.76-1.85 (m, 1H), 2.19 (d, J=7.14 Hz, 2H), 2.55-2.67 (m, 4H), 3.18-3.25 (m, 6H), 3.45-3.52 (m, 2H), 4.42 (s, 1H), 7.14 (dt, J=7.18, 1.59 Hz, 1H), 7.21 (t, J=7.66 Hz, 1H), 7.25 (dt, J=8.02, 1.96 Hz, 1H), 7.30 (d, J=8.20 Hz, 2H), 7.53 (d, J=8.30 Hz, 2H). [a]$_D^{20}$=−14.43 deg [c 0.420, MeOH].

COMPOUND 41: N,N-diethyl-4-[(R)-{3-[(3-phenylpropanoyl)amino]phenyl}(piperazin-1-yl)methyl]benzamide

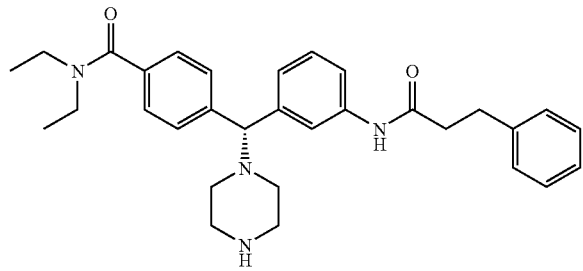

To a solution of INTERMEDIATE 5b (128 mg) in dimethylformamide (3 mL) was added hydrocinammic acid (49 g; 1.2 eq), HATU (156 g; 1.5eq) and N,N-diisopropylethylamine (190 μL; 4 eq). The reaction was stirred at room temperature under nitrogen. After 18 hours, the reaction was concentrated and the crude dissolved in dichloromethane (5 mL) and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified twice by reverse phase chromatography, eluting 10% to 45% acetonitrile in water containing 0.1% trifluoroacetic acid. The product was obtained as the trifluoroacetic acid salt and was lyophilized to give COMPOUND 41 (24 mg, 12% yield) as a colourless solid. Purity (HPLC): >99%; Optical purity (Chiral HPLC): >99%; $^1$H NMR (400 MHz, CD$_3$OD) 1.06 (t, J=6.64 Hz, 3H), 1.19 (t, J=6.88 Hz, 3H), 2.61 (t, J=7.66 Hz, 2H), 2.56-2.67 (m, 4H), 2.95 (t, J=7.66 Hz, 2H), 3.18-3.26 (m, 6H), 3.45-3.53 (m, 2H), 4.41 (s, 1H), 7.13-7.16 (m, 2H), 7.19-7.24 (m, 6H), 7.30 (d, J=8.30 Hz, 2H), 7.52 (d, J=8.20 Hz, 2H). $[a]_D^{20}$=−14.34 deg [c 0.442, MeOH].

COMPOUND 42: 4-[(R)-{3-[(cyclohexylcarbonyl)amino]phenyl}(piperazin-1-yl)methyl]-N,N-diethylbenzamide

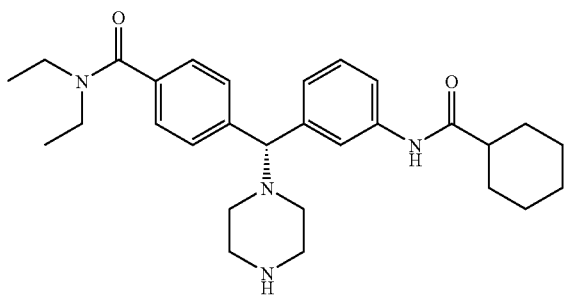

To a solution of INTERMEDIATE 5b (150 mg) in dimethylformamide (5 mL) was added cyclohexanecarboxylic acid (50 g; 1.2 eq), HATU (182 g; 1.5 eq) and N,N-diisopropylethylamine (222 μL; 4 eq). The reaction was stirred at room temperature under nitrogen. After 18 hours, the reaction was concentrated and the crude dissolved in dichloromethane (5 mL) and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 42 (41 mg, 18% yield) as a colourless solid. Purity (HPLC): >99%; Optical purity (Chiral HPLC): >99%; $^1$H NMR (400 MHz, CD$_3$OD) 1.06 (t, J=6.83 Hz, 3H), 1.19 (t, J=3.83 Hz, 3H), 1.25-1.37 (m, 2H), 1.42-1.54 (m, 2H), 1.66-1.73 (m, 1H), 1.76-1.86 (m, 5H), 2.31 (tt, J=11.69, 3.25 Hz, 1H), 2.55-2.67 (m, 4H), 3.20-3.25 (m, 6H), 3.45-3.53 (m, 2H), 4.41 (s, 1H), 7.11-7.14 (m, 1H), 7.19-7.24 (m, 2H), 7.30 (d, J=8.20 Hz, 2H), 7.52 (d, J=8.20 Hz, 2H), 7.87 (s, 1H). $[a]_D^{20}$=−21.39 deg [c 0.345, MeOH].

COMPOUND 43: N,N-diethyl4-[(R)-{3-[(phenylsulfonyl)amino]phenyl}(piperazin-1-yl)methyl]benzamide

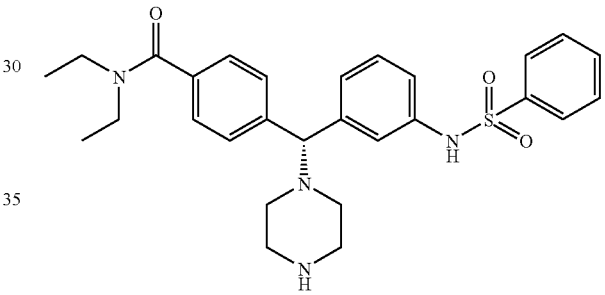

To a solution of INTERMEDIATE 5b (110 mg) in dichloromethane (10 mL) was added benzene sulfonyl chloride (33 μL; 1.1 eq) and triethylamine (108 μL; 3.3 eq). The reaction was stirred at room temperature under nitrogen. After 18 hours, the trifluoroacetic acid (1 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 40% acetonitrile in water containing 0.1% trifluoroacetic acid. The product was obtained as the trifluoroacetic acid salt and was lyophilized to give COMPOUND 43 (60 mg, 35% yield) as a colourless solid. Purity (HPLC): >99%; Optical purity (Chiral BPLC): >99%; $^1$H NMR (400 MHz, CD$_3$OD) 1.06 (t, J=6.44 Hz, 3H), 1.20 (t, J=6.44 Hz, 3H), 2.47-2.57 (m, 2H), 3.14-3.25 (m, 6H), 3.43, 3.53 (m, 2H), 4.34 (s, 1H), 6.81-6.86 (m, 1H), 7.06-7.14 (m, 2H), 7.25-7.32 (m, 3H), 7.36-7.44 (m, 4H), 7.48-7.55 (m, 1H), 7.06-7.65 (m, 2H).

Found: C, 53.38; H, 5.29; N, 8.22. $C_{28}H_{34}N_4O_3S \times 1.6$ $CF_3CO_2H \times 0.7$ $H_2O$ has C, 53.40; H, 5.31; N, 7.98%. $[a]_D^{20}$=−7.45 deg [c 0.845, MeOH].

COMPOUND 44: 4-[(R)-{3-[(benzylsulfonyl)amino]phenyl}(piperazin-1-yl)methyl]-N,N-diethylbenzamide

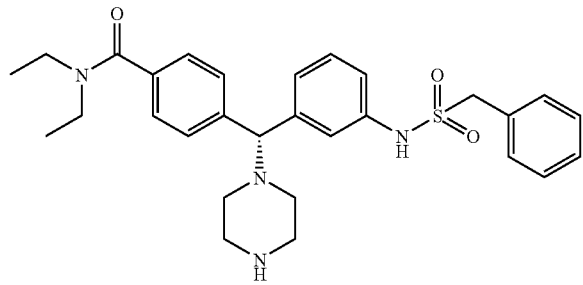

To a solution of INTERMEDIATE 5b (82 mg) in pyridine (3 mL) was added α-toluene sulfonyl chloride (40 g; 1.2 eq). The reaction was stirred at room temperature under nitrogen. After 18 hours, reaction was concentrated and the crude product dissolved in dichloromethane (10 mL) and trifluoroacetic acid (1 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 40% acetonitrile in water containing 0.1% trifluoroacetic acid. The product was obtained as the trifluoroacetic acid salt and was lyophilized to give COMPOUND 44 (47 mg, 36% yield) as a colourless solid. Purity (HPLC): >99%; Optical purity (Chiral HPLC): >99%; $^1$H NMR (400 MHz, CD$_3$OD) 1.01 (t, J=6.91 Hz, 3H), 1.18 (t, J=6.75 Hz, 3H), 2.56-2.66 (m, 4H), 3.15-3.26 (m, 6H), 3.43-3.52 (m, 2H), 4.29 (s, 2H), 4.42 (s, 1H), 6.96 (ddd, J=7.96, 2.25, 1.12 Hz, 1H), 7.12-7.16 (m, 3H), 7.19-7.28 (m, 4H), 7.31-7.35 (m, 3H), 7.53 (d, J=8.02 Hz, 2H). Found: C, 55.53; H, 5.52; N, 8.11. $C_{29}H_{36}N_4O_3 \times 1.1H_2O \times 0.6CF_3COOH$ has C, 55.57; H, 5.58; N, 7.95%. $[a]_D^{20}=-7.23$ deg [c 0.844, MeOH].

COMPOUND 45: N,N-diethyl-4-[(S)-{3-[(phenylsulfonyl)amino]phenyl}(piperazin-1-yl)methyl]benzamide

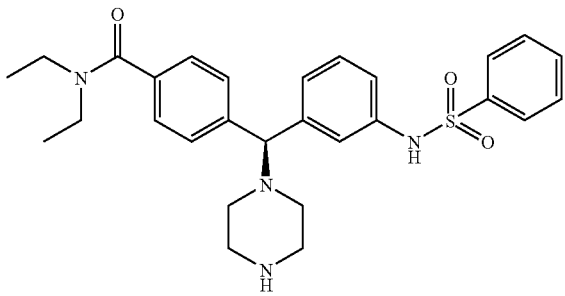

To a solution of INTERMEDIATE 5a (108 mg) in pyridine (2 mL) was added benzene sulfonyl chloride (38 μL; 1.3 eq). The reaction was stirred at room temperature under nitrogen. After 18 hours, reaction was concentrated and the crude product dissolved in dichloromethane (5 mL) and trifluoroacetic acid (0.5 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 10% to 40% acetonitrile in water containing 0.1% trifluoroacetic acid. The product was obtained as the trifluoroacetic acid salt and was lyophilized to give COMPOUND 45 (86 mg, 50% yield) as a colourless solid. Purity (HPLC): >99%; Optical purity (Chiral HPLC): >99%; $^1$H NMR (400 MHz, CD$_3$OD) 1.06 (t, J=6.69 Hz, 3H), 1.20 (t, J=6.69 Hz, 3H), 2.46-2.56 (m, 4H), 3.15-3.26 (m, 6H), 3.45-3.53 (m, 2H), 4.35 (s, 1H), 6.83 (dt, J=7.59, 1.67 Hz, 1H), 7.05-7.08 (m, 1H), 7.11 (t, J=7.62 Hz, 1H), 7.28 (d, J=8.10 Hz, 2H), 7.29-7.32 (m, 1H), 7.34-7.43 (m, 4H), 7.47-7.53 (m, 1H), 7.61-7.65 (m, 2H). Found: C, 51.87; H, 5.04; N, 7.59. $C_{28}H_{34}N_4O_3S \times 0.7H_2O \times 1.9CF_3COOH$ has C, 51.90; H, 5.11; N, 7.61%. $[a]_D^{20}=+0.43$ deg [c 0.917, MeOH].

COMPOUND 46: 4-[(R)-{3-[(aminocarbonyl)amino]phenyl}(piperazin-1-yl)methyl]-N,N-diethylbenzamide

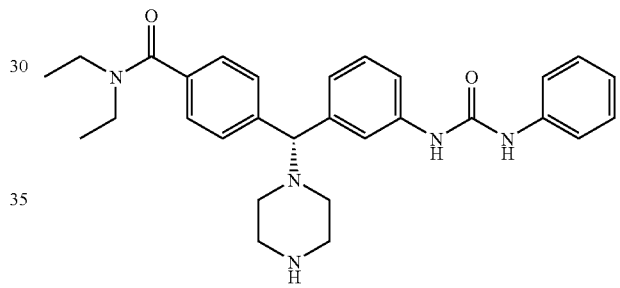

To a solution of INTERMEDIATE 5b (110 mg) in dichloromethane (3 mL) was added phenyl isocyanate (31 μL; 1.2 eq) and triethylamine (1 drop). The reaction was stirred at room temperature under nitrogen. After 18 hours, trifluoroacetic acid (1 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 12% to 35% acetonitrile in water containing 0.1% trifluoroacetic acid. The product was obtained as the trifluoroacetic acid salt and was lyophilized to give COMPOUND 46 (64 mg, 38% yield) as a colourless solid. Purity (HPLC): >99%; Optical purity (Chiral HPLC): >99%; $^1$H NMR (400 MHz, CD$_3$OD) 1.06 (t, J=6.69 Hz, 3H), 1.19 (t, J=6.93 Hz, 3H), 2.55-2.67 (m, 4H), 3.20-3.26 (m, 6H), 3.44-3.51 (m, 2H), 4.42 (s, 1H), 6.99 (tt, J=7.37, 1.12 Hz, 1H), 7.05-7.11 (m, 2H), 7.20 (t, J=7.81 Hz, 1H), 7.22-7.28 (m, 2H), 7.30 (d, J=8.20 Hz, 2H), 7.38 (d, J=7.52 Hz, 2H), 7.55 (d, J=8.20 Hz, 2H), 7.76 (t, J=1.76 Hz, 1H). Found: C, 54.42; H, 5.28; N, 9.67. $C_{29}H_{35}N_5O_2 \times 0.8H_2O \times 2.0CF_3COOH$ has C, 54.44; H, 5,34; N, 9.62%. $[a]_D^{20}=-28.95$ deg [c 0.836, MeOH].

COMPOUND 47: 4-[(R)-{3-[(anilinocarbonothioyl)amino]phenyl}(piperazin-1-yl)methyl]-N,N-diethylbenzamide

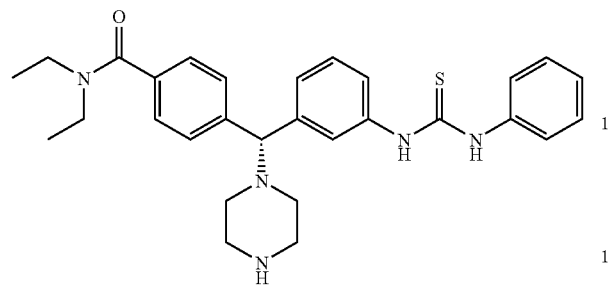

To a solution of INTERMEDIATE 5b (115 mg) in dichloromethane (3 mL) was added phenyl isothiocyanate (35 μL; 1.2 eq) and triethylamine (1 drop). The reaction was stirred at room temperature under nitrogen. After 18 hours, reaction was concentrated and purified by normal phase chromatography eluting with 35% acetone in hexane. The pure fractions were concentrated and dissolved in dichloromethane (10 mL) in which trifluoroacetic acid (1 mL) was added to the reaction and stirred for 18 hours until complete removal of the boc group. The reaction was diluted with dichloromethane and washed with saturated aqueous sodium bicarbonate. The aqueous was extracted with two portions of dichloromethane and the combined organics were dried over anhydrous sodium sulfate, filtered and concentrated. The residue was purified by reverse phase chromatography, eluting 12% to 35% acetonitrile in water containing 0.1% trifluoroacetic acid. The product was obtained as the trifluoroacetic acid salt and was lyophilized to give COMPOUND 48 (33 mg, 18% yield) as a colourless solid. Purity (HPLC): >99%; Optical purity (Chiral HPLC): >99%; $^1$H NMR (400 MHz, CD$_3$OD) 1.07 (t, J=6.5 Hz, 3H), 1.22 (t, J=6.8 Hz, 3H), 2.54-2.81 (m, 3H), 3.18-3.29 (m, 7H), 3.46-3.58 (m, 2H), 4.49 (s, 1H), 7.09-7.16 (m, 1H), 7.17-7.24 (m, 2H), 7.25-7.45 (m, 7H), 7.56 (d, J=8.2 Hz, 2H), 7.84 (t, J=1.8 Hz, 1H)

COMPOUND 48: N,N-diethyl-4-[(S)-1-piperazinyl[3-(propylamino)phenyl]methyl]benz-amide and
COMPOUND 49: 4-[(S)-[3-(dipropylamino)phenyl]-1-piperazinylmethyl]-N,N-diethylbenzamide

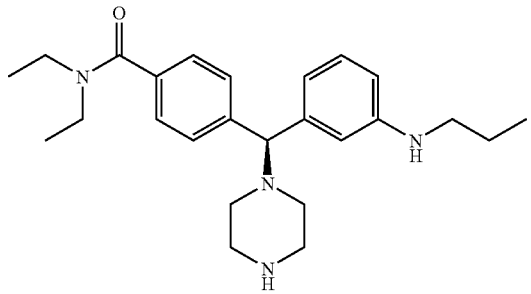

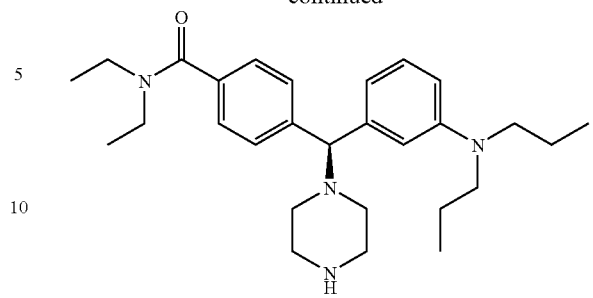

Using the same method as for COMPOUND 17 and using INTERMEDIATE 5a (208 mg, 0.45 mmol), propionaldehyde (0.036 mL, 0.50 mmol), and decaborane (16.4 mg, 0.13 mmol) afforded COMPOUND 48 (174 mg, 52% yield) and COMPOUND 49 (43.5 mg, 12% yield) as their TFA salts. Each compound was lyophilized from CH$_3$CN/H$_2$O to produce colourless solids. COMPOUND 48: Purity (HPLC): >99%; Optical purity (Chiral HPLC): >99%; $^1$H NMR (400 MHz, CD$_3$OD) δ1.01 (t, J=7.4 Hz, 3H), 1.09 (br t, J=6.7 Hz, 3H), 1.22 (br t, J=6.3 Hz, 3H), 1.69 (sextet, J=7.6 Hz, 2H), 2.65 (br s, 4H), 3.20-3.29 (m, 8H), 3.52 (br q, J=6.4 Hz, 2H), 4.54 (s, 1H), 7.11-7.17 (m, 1H), 7.34 (d, J=8.0 Hz, 2H), 7.39-7.43 (m, 3H), 7.56 (d, J=8.2 Hz, 2H). Found: C, 51.41; H, 5.79; N, 7.98. C$_{25}$H$_{36}$N$_4$O×0.8 H$_2$O×2.4 CF$_3$COOH has C, 51.38; H, 5.79; N, 8.04%. [α]$_D^{20}$=+7.18 deg [c 1.64, MeOH].

COMPOUND 49: Purity (HPLC): >82%; $^1$H NMR (400 MHz, CD$_3$OD) δ0.83 (t, J=7.3 Hz, 6H), 1.04 (br t, J=6.4 Hz, 3H), 1.18 (br t, J=6.5 Hz, 3H), 1.30-1.44 (m, 4H), 2.63 (d, J=5.1 Hz, 4H), 3.14-3.28 (m, 6H), 3.43-3.52 (m, 6H), 4.59 (s, 1H), 7.31 (d, J=8.2 Hz, 2H), 7.36 (d, J=7.4 Hz, 1H), 7.47-7.58 (m, 4H), 7.66 (s, 1H).

COMPOUND 50: N,N-diethyl-4-[(R)-1-piperazinyl[3-(propylamino)phenyl]methyl]benz-amide and COMPOUND 51: 4-[(R)-[3-(dipropylamino)phenyl]-1-piperazinylmethyl]-N,N-diethylbenzamide

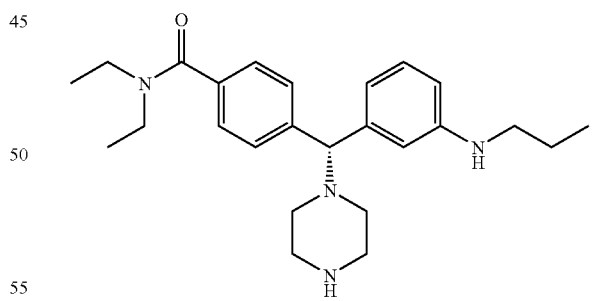

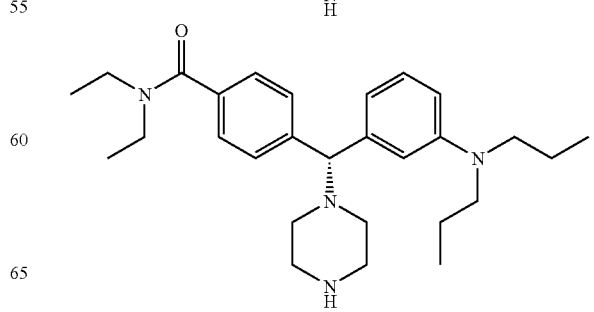

Using the same method as for COMPOUND 17 and using INTERMEDIATE 5b (404 mg, 0.87 mmol), propionaldehyde (0.069 mL, 0.96 mmol), and decaborane (31.7 mg, 0.26 mmol) afforded COMPOUND 50 (217 mg, 34% yield) and COMPOUND 51 (128 mg, 19% yield) as their TFA salts. Each compound was lyophilized from $CH_3CN/H_2O$, producing COMPOUND 50 as a slightly yellow solid and COMPOUND 51 as a colourless solid. COMPOUND 50: Purity (HPLC): >99%; Optical purity (Chiral HPLC): >99%; $^1H$ NMR (400 MHz, $CD_3OD$) $\delta$1.01 (t, J=7.4 Hz, 3H), 1.09 (br t, J=6.8 Hz, 3H), 1.22 (br t, J=7.0 Hz, 3H), 1.70 (sextet, J=7.6 Hz, 2H), 2.65 (br s, 4H), 3.20-3.29 (m, 8H), 3.52 (br q, J=6.7 Hz, 2H), 4.56 (s, 1H), 7.21 (ddd, J=7.8, 2.3, 1.3 Hz, 1H), 7.35 (d, J=8.4 Hz, 2H), 7.43-7.52 (m, 3H), 7.56 (d, J=8.2 Hz, 2H). Found: C, 46.23; H, 5.02; N, 6.58. $C_{25}H_{36}N_4O \times 1.0\ H_2O \times 3.6\ CF_3COOH$ has C, 46.20; H, 5.01; N, 6.69%. $[\alpha]_D^{18}$=−2.6 deg [c 0.657, MeOH].

COMPOUND 51: Purity (HPLC): >99%; Optical purity (Chiral HPLC): >99%; $^1H$ NMR (400 MHz, $CD_3OD$) $\delta$0.83 (t, J=7.4 Hz, 6H), 1.04 (br t, J=6.6 Hz, 3H), 1.18 (br t, J=6.8 Hz, 3H), 1.29-1.44 (m, 4H), 2.62 (d, J=4.5 Hz, 4H), 3.15-3.29 (m, 6H), 3.42-3.55 (m, 6H), 4.59 (s, 1H), 7.31 (d, J=8.0 Hz, 2H), 7.37 (d, J=7.6 Hz, 1H), 7.47-7.61 (m, 4H), 7.67 (s, 1H). Found: C, 45.63; H, 5.04; N, 6.21. $C_{28}H_{42}N_4O \times 1.5\ H_2O \times 4.2\ CF_3COOH$ has C, 45.70; H, 5.18; N, 5.86%. $[\alpha]_D^{17}$=−6.3 deg [c 0.914, MeOH].

COMPOUND 52: N,N-diethyl-4-[(S)-1-piperazinyl [3-[[[4-(3-pyridinyl)phenyl]methyl]-amino]phenyl] methyl]benzamide

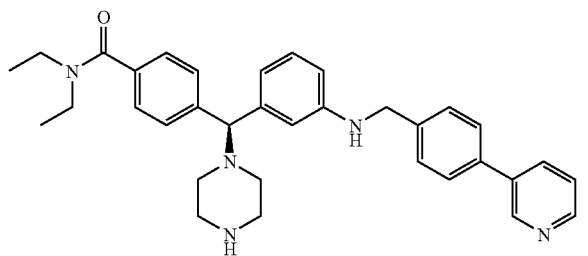

Using the same method as for COMPOUND 17 and using INTERMEDIATE 5a (205 mg, 0.44 mmol), 4-(3-pyridinyl) benzaldehyde (88.7 mg, 0.48 mmol), and decaborane (16.4 mg, 0.13 mmol) afforded COMPOUND 52 (266 mg, 61% yield) as its TFA salt. This material was lyophilized from $CH_3CN/H_2O$ to produce a slightly yellow solid.

Purity (HPLC): >99%; Optical purity (Chiral HPLC): >99%; $^1H$ NMR (400 MHz, $CD_3OD$) $\delta$ 1.07 (br t, J=6.9 Hz, 3H), 1.20 (br t, J=6.6 Hz, 3H), 2.65 (br s, 4H), 3.21 (br s, 6H), 3.49 (br q, J=7.2 Hz, 2H), 4.38 (s, 1H), 4.47 (s, 2H), 6.66 (dd, J=8.1, 1.5 Hz, 1H), 6.85 (d, J=7.8 Hz, 1H), 6.89 (s, 1H), 7.10 (t, J=7.8 Hz, 1H), 7.25 (d, J=8.2 Hz, 2H), 7.49 (d, J=8.2 Hz, 2H), 7.55 (d, J=8.2 Hz, 2H), 7.76 (d, J=8.4 Hz, 2H), 8.08 (dd, J=8.0, 5.7 Hz, 1H), 8.79 (d, J=4.9 Hz, 1H), 8.82 (d, J=8.2 Hz, 1H), 9.14 (s, 1H). Found: C, 53.11; H, 4.81; N, 7.56. $C_{34}H_{39}N_5O \times 0.5\ H_2O \times 3.3\ CF_3COOH$ has C, 53.06; H, 4.75; N, 7.62%. $[\alpha]_D^{18}$=+10.7 deg [c 1.43, MeOH].

COMPOUND 53: N,N-diethyl-4-[(S)-[3-[[[4-(1H-imidazol-1-yl)phenyl]methyl]amino]-phenyl]-1-piperazinylmethyl]benzamide

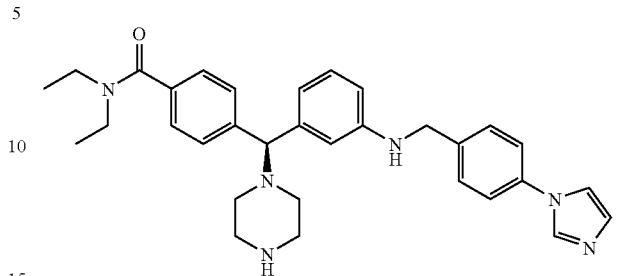

Using the same method as for COMPOUND 17 and using INTERMEDIATE 5a (206 mg, 0.44 mmol), 4-(1H-imidazol-1-yl)benzaldehyde (83.6 mg, 0.49 mmol), and decaborane (16.4 mg, 0.13 mmol) afforded COMPOUND 53 (181 mg, 42% yield) as its TFA salt. This material was lyophilized from $CH_3CN/H_2O$ to produce a colourless solid. Purity (HPLC): >99%; Optical purity (Chiral HPLC): >99%; $^1H$ NMR (400 MHz, $CD_3OD$) $\delta$ 1.09 (br t, J=6.7 Hz, 3H), 1.21 (br t, J=6.7 Hz, 3H), 2.63 (br s, 4H), 3.15-3.28 (m, 6H), 3.51 (q, J=6.1 Hz, 2H), 4.32 (s, 1H), 4.43 (s, 2H), 6.47-6.52 (m, 1H), 6.71-6.76 (m, 2H), 7.02 (t, J=8.0 Hz, 1H), 7.26 (d, J=8.2 Hz, 2H), 7.49 (d, J=8.2 Hz, 2H), 7.58 (d, J=8.6 Hz, 2H), 7.64 (d, J=8.6 Hz, 2H), 7.76 (s, 1H), 8.05 (s, 1H), 9.44 (s, 1H). Found: C, 51.44; H, 4.89; N, 9.63. $C_{32}H_{38}N_6O \times 1.2\ H_2O \times 3.0\ CF_3COOH$ has C, 51.49; H, 4.94, N, 9.48%. $[\alpha]_D^{17}$=−2.1 deg [c 0.872, MeOH].

COMPOUND 54: N,N-diethyl-4-[(S)-1-piperazinyl [3-[(2-quinolylmethyl)amino]phenyl]-methyl]benzamide

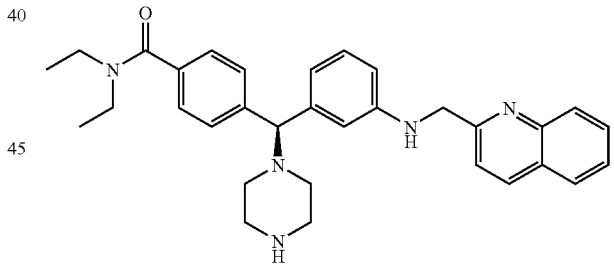

Using the same method as for COMPOUND 17 and using INTERMEDIATE 5a (209 mg, 0.45 mmol), 2-quinolinecarboxaldehyde (77.6 mg, 0.49 mmol), and decaborane (16.4 mg, 0.13 mmol) afforded COMPOUND 54 (162 mg, 38% yield) as its TFA salt. This material was lyophilized from $CH_3CN/H_2O$ to produce a yellow solid. Purity (HPLC): >98%; Optical purity (Chiral HPLC): >99%; $^1H$ NMR (400 MHz, $CD_3OD$) $\delta$ 1.07 (br t, J=6.7 Hz, 3H), 1.23 (br t, J=6.6 Hz, 3H), 2.59 (br s, 4H), 3.18 (br t, J=4.4 Hz, 6H), 3.52 (br q, J=7.2 Hz, 2H), 4.30 (s, 1H), 4.89 (s, 2H), 6.58 (dd, J=7.9, 2.1 Hz, 1H), 6.72 (s, 1H), 6.82 (d, J=7.4 Hz, 1H), 7.04-7.12 (m, 3H), 7.36 (d, J=8.2 Hz, 2H), 7.85-7.93 (m, 2H), 8.09 (td, J=7.8, 1.2 Hz, 1H), 8.22 (d, J=8.2 Hz, 1H), 8.27 (d, J=8.4 Hz, 1H), 8.87 (d, J=8.6 Hz, 1H). Found: C, 50.15; H, 4.57; N, 7.46. $C_{32}H_{37}N_5O \times 1.1\ H_2O \times 3.6\ CF_3COOH$ has C, 50.20; H, 4.60; N, 7.47%. $[\alpha]_D^{17}$=+20.8 deg [c 0.726, MeOH].

COMPOUND 55: 4-[(R)-[3-[(2,2-diphenylethyl)amino]phenyl]-1-piperazinylmethyl]-N,N-diethylbenzamide

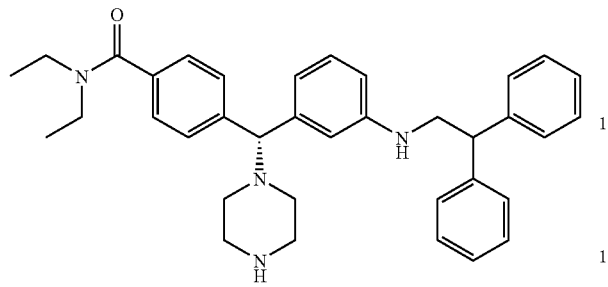

Using the same method as for COMPOUND 17 and using INTERMEDIATE 5b (251 mg, 0.54 mmol), diphenylacetaldehyde (0.11 mL, 0.62 mmol), and decaborane (21.6 mg, 0.18 mmol) afforded COMPOUND 55 (186 mg, 39% yield) as its TFA salt. This material was lyophilized from CH$_3$CN/H$_2$O to produce a white solid. Purity (HPLC): >96%; Optical purity (Chiral HPLC): >99%; $^1$H NMR (400 MHz, CD$_3$OD) δ 1.06 (br t, J=7.0 Hz, 3H), 1.22 (br t, J=7.0 Hz, 3H), 2.65 (br s, 4H), 3.19-3.28 (m, 6H), 3.51 (br q, J=7.2 Hz, 2H), 3.79 (d, J=7.6 Hz, 2H), 4.24 (t, J=7.6 Hz, 1H), 4.38 (s, 1H), 6.65 (dd, J=8.1, 1.5 Hz, 1H), 6.86 (s, 1H), 6.91 (d, J=7.6 Hz, 1H), 7.14 (t, J=7.9 Hz, 1H), 7.17-7.23 (m, 2H), 7.23-7.35 (m, 10H), 7.55 (d, J=8.2 Hz, 2H). Found: C, 56.89; H, 5.33; N, 6.32. C$_{36}$H$_{42}$N$_4$O×0.7 H$_2$O×2.8 CF$_3$COOH has C, 56.87; H, 5.30; N, 6.38%. $[\alpha]_D^{18}$=+2.5 deg [c 1.023, MeOH].

COMPOUND 56: 4-[(R)-[3-[[[4-(1,1-dimethylethyl)phenyl]methyl]amino]phenyl]-1-piperazinylmethyl]-N,N-diethylbenzamide

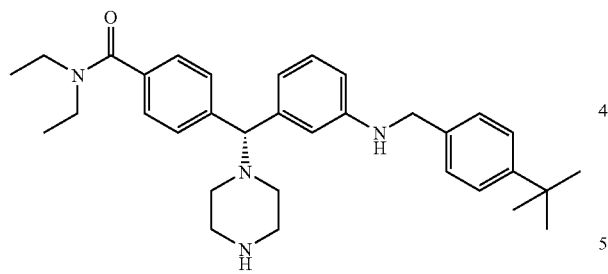

Using the same method as for COMPOUND 17 and using INTERMEDIATE 5b (254 mg, 0.54 mmol), 4-(1,1-dimethylethyl)benzaldehyde (0.10 mL, 0.60 mmol), and decaborane (21.6 mg, 0.18 mmol) afforded COMPOUND 56 (326 mg, 70% yield) as its TFA salt. This material was lyophilized from CH$_3$CN/H$_2$O to produce a white solid. Purity (HPLC): >99%; Optical purity (Chiral HPLC): >99%; $^1$H NMR (400 MHz, CD$_3$OD) δ 1.09 (br t, J=6.7 Hz, 3H), 1.22 (br t, J=6.5 Hz, 3H), 1.30 (s, 9H), 2.63 (br s, 4H), 3.21-3.27 (m, 6H), 3.52 (br q, J=7.0 Hz, 2H), 4.45 (s, 2H), 4.49 (s, 1H), 7.02 (d, J=7.4 Hz, 1H), 7.25-7.36 (m, 7H), 7.40 (d, J=8.4 Hz, 2H), 7.50 (d, J=8.0 Hz, 2H). Found: C, 49.54; H, 4.95; N, 5.67. C$_{33}$H$_{44}$N$_4$O×0.7 H$_2$O×4.2 CF$_3$COOH has C, 49.52; H, 4.98; N, 5.58%. $[\alpha]_D^{19}$=−9.23 deg [c 1.387, MeOH].

COMPOUND 57: N,N-diethyl-4-[(R)-[3-[[(4-phenoxyphenyl)methyl]amino]phenyl]-1-piperazinylmethyl]benzamide

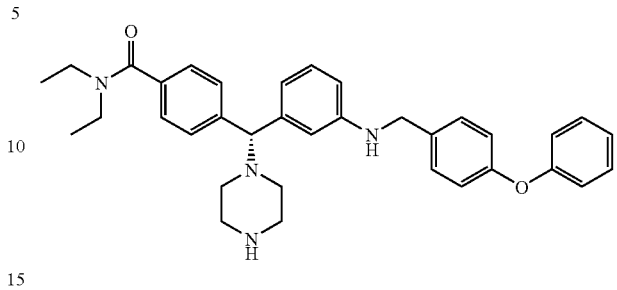

Using the same method as for COMPOUND 17 and using INTERMEDIATE 5b (252 mg, 0.54 mmol), 4-phenoxybenzaldehyde (0.10 mL, 0.59 mmol), and decaborane (21.6 mg, 0.18 mmol) afforded COMPOUND 57 (269 mg, 56% yield) as its TFA salt. This material was lyophilized from CH$_3$CN/H$_2$O to produce a white solid. Purity (HPLC): >99%; Optical purity (Chiral HPLC): >99%; $^1$H NMR (400 MHz, CD$_3$OD) δ 1.07 (br t, J=6.4 Hz, 3H), 1.21 (br t, J=6.4 Hz, 3H), 2.60 (br s, 4H), 3.17-3.27 (m, 6H), 3.51 (br q, J=6.6 Hz, 2H), 4.42 (s, 1H), 4.44 (s, 2H), 6.90-7.00 (m, 5H), 7.07 (s, 1H), 7.09-7.17 (m, 2H), 7.24-7.38 (m, 7H), 7.46 (d, J=8.0 Hz, 2H). Found: C, 58.02; H, 5.40; N, 6.77. C$_{35}$H$_{40}$N$_4$O$_2$× 0.5 H$_2$O×2.3 CF$_3$COOH has C, 58.01; H, 5.32, N, 6.83%. $[\alpha]_D^{17}$=−19.7 deg [c 1.340, MeOH].

COMPOUND 58: N,N-diethyl-4-[(R)-[4-(2-propenyl)-1-piperazinyl][3-(propylamino)-phenyl]methyl]benzamide

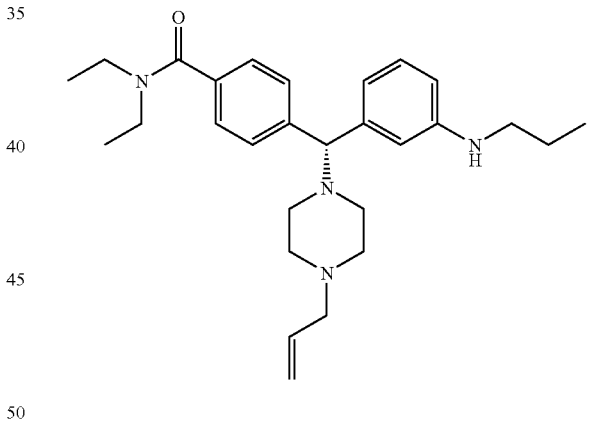

A solution of COMPOUND 50 (54.8 mg, 0.13 mmol) in CH$_3$CN (4 mL) was cooled to 0° C. Triethylamine (22.4 µL, 0.16 mmol) and alkyl bromide (11.6 µL, 0.13 mmol) were added, and the reaction was allowed to warm to room temperature and stir for 2.5 hours. The reaction was then concentrated, and the residue was dissolved in CH$_2$Cl$_2$ and washed twice with water. The organic phase was dried over anhydrous sodium sulfate, filtered and concentrated. The residue was purified by reverse phase chromatography, eluting 5% to 50% acetonitrile in water containing 0.1% trifluoroacetic acid. The product was obtained as the trifluoroacetic acid salt and was lyophilized to give COMPOUND 58 (54 mg, 51% yield) as a hygroscopic, white solid. Purity (HPLC): >99%; Optical purity (Chiral HPLC): >99%; $^1$H NMR (400 MHz, CD$_3$OD) δ 1.01 (t, J=7.4 Hz, 3H), 1.09 (br t, J=6.6 Hz, 3H), 1.22 (br t, J=6.7 Hz, 3H), 1.70 (sextet, J=7.6 Hz, 2H), 2.38 (br s, 2H), 3.02 (br s, 2H), 3.12-3.29 (m, 6H), 3.44-3.57 (m, 4H), 3.78 (d, J=7.0 Hz, 2H), 4.57 (s, 1H), 5.57-5.63 (m, 2H), 5.87-6.00 (m, 1H), 7.20 (dt, J=7.4, 1.9 Hz, 1H), 7.34 (d, J=8.2 Hz, 2H), 7.41-7.50 (m, 3H), 7.56 (d, J=8.2 Hz, 2H). Found: C, 51.99; H, 5.85; N, 7.25. $C_{28}H_{40}N_4O \times 0.8\ H_2O \times 2.7\ CF_3COOH$ has C, 52.04; H, 5.79; N, 7.27%. $[\alpha]_D^{17}=-2.6$ deg [c 1.03, MeOH].

COMPOUND 59: 4-{(R)-(3-aminophenyl)[4-(2-methoxyethyl)piperazin-1-yl]methyl}-N,N-diethyl-benzamide

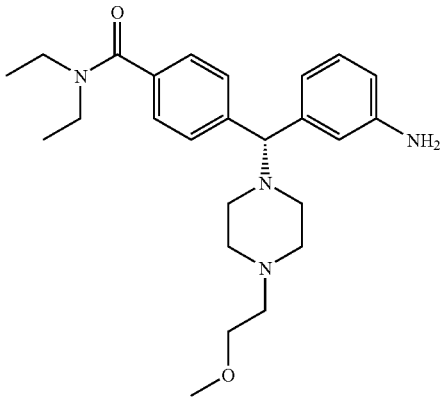

In a 5 mL microwave vial was added INTERMEDIATE 4b (1.7 g; 4.29 mmol) in DMF (4 mL) followed by potassium carbonate (1.19 g; 8.58 mmol) and 2-bromoethyl methyl ether (0.53 mL; 5.58 mmol). The reaction mixture was heated to 130° C. for 15 minutes then was concentrated under reduced pressure. The residue was dissolved in dichloromethane and washed with saturated sodium bicarbonate followed by water. The organic phase was dried over anhydrous sodium sulphate, filtered and concentrated under reduced pressure. Column chromatography eluting with 4% methanol in dichloromethane gave the desired product (0.9 g; 46% yield).

The above product was dissolved in a mixture of ethanol=/water/NH$_4$Cl (2.1 mL) and iron (1.1 g; 19.8 mmol) was added. The reaction mixture was heated to 90° C. for 5 hours, then was allowed to cool to room temperature, filtered on a celite pad and concentrated under reduced pressure. The residue was dissolved in ethyl acetate and washed with water. The organic phase was dried over anhydrous sodium sulphate, filtered and concentrated under reduced pressure. Column chromatography eluting with 2% methanol and 1% NH$_4$OH in dichloromethane gave COMPOUND 59 (620 g; 74% yield). Purity (HPLC-215 nm): >99%; Optical purity (Chiral HPLC-215 nm): >99%. $^1$H NMR (400 MHz, CD$_3$OD) δ 0.99 (t, J=7.52 Hz, 3H), 1.12 (t, J=6.54 Hz, 3H), 3.08-3.17 (br s, 3H), 3.18-3.23 (m, 6H), 3.29 (s, 3H), 3.26-3.32 (m, 3H), 3.44-3.51 (br s, 1H), 3.59-3.64 (m, 3H), 5.38 (s, 1H), 7.20 (d, J=7.42 Hz, 1H), 7.26 (d, J=8.01 Hz, 2H), 7.43 (t, J=7.81 Hz, 1H), 7.47-7.54 (br s, 3H), 7.59 (d, J=7.62 Hz, 1H). Found: C, 52.41; H, 7.54; N, 9.16. $C_{25}H_{36}N_4O_2 \times 3.2HCl \times 1.8H_2O$ has C, 52.34; H, 7.52; N, 9.77%. $[\alpha]_D^{17}=-7.0$ deg [c 0.50, MeOH].

COMPOUND 60: 4-{(R)-(3-aminophenyl)[4-(3-methoxypropyl)piperazin-1-yl]methyl}-N,N-diethyl-benzamide

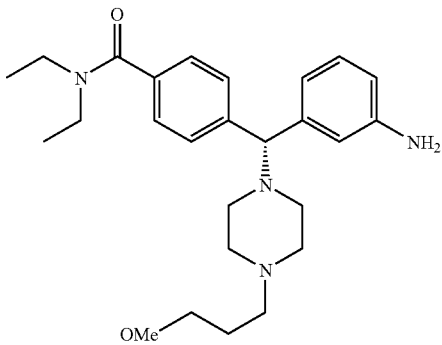

In a 5 mL microwave vial was added INTERMEDIATE 4b (1.7 g; 4.29 mmol) in DMF (3 mL) followed by potassium carbonate (1.19 g; 8.58 mmol) and 1-bromo-3-methoxypropane (0.85 g; 5.58 mmol). The reaction mixture was heated to 130° C. for 15 minutes then was concentrated under reduced pressure. The residue was dissolved in dichloromethane and washed with saturated sodium bicarbonate followed by water. The organic phase was dried over anhydrous sodium sulphate, filtered and concentrated under reduced pressure. Column chromatography eluting with 3% methanol in dichloromethane gave the desired product (1.67 g; 83% yield).

The above product was dissolved in a mixture of ethanol/THF/water/NH$_4$Cl (3.5 mL) and iron (2.0 g; 35.6 mmol) was added. The reaction mixture was heated to 90° C. for 5 hours, then was allowed to cool to room temperature, filtered on a celite pad and concentrated under reduced pressure. The residue was dissolved in ethyl acetate and washed with water. The organic phase was dried over anhydrous sodium sulphate, filtered and concentrated under reduced pressure. Column chromatography eluting with 2% methanol and 1% NH$_4$OH in dichloromethane gave COMPOUND 60 (240 mg+140 mg (93% pure); 24% yield). Purity (HPLC-215 nm): >99%; Optical purity (Chiral HPLC-215 nm): >99%. $^1$H NMR (400 MHz, CD$_3$OD) δ 0.98 (t, J=6.64 Hz, 3H), 1.11 (t, J=7.03 Hz, 3H), 1.86-1.94 (m, 2H), 3.12-3.16 (br s, 3H), 3.17-3.21 (m, 9H), 3.22 (s, 3H), 3.41-3.46 (br s, 1H), 3.47-3.54 (br s, 3H), 5.38 (s, 1H), 7.21 (d, J=7.03 Hz, 1H), 7.27 (d, J=7.62 Hz, 2H), 7.44 (t, J=7.91 Hz, 1H), 7.52-7.57 (br s, 3H), 7.59-7.66 (br s, 1H). Found: C, 50.17; H, 7.48; N, 8.70. $C_{26}H_{38}N_4O_2 \times 4.0HCl \times 2.1H_2O$ has C, 50.18; H, 7.48; N, 9.00%. $[\alpha]_D^{17}=-7.1$ deg [c 0.52, MeOH].

COMPOUND 61: N,N-diethyl-4-[(R)-[4-(2-methoxyethyl)-1-piperazinyl][3-(propylamino)-phenyl]methyl]benzamide

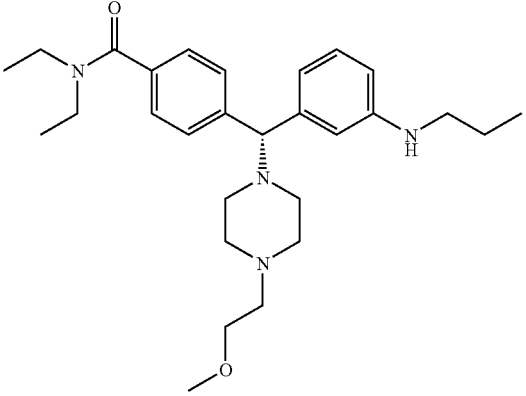

A solution of COMPOUND 59 (93.0 mg, 0.22 mmol), propionaldehyde (0.016 mL, 0.22 mmol) and decaborane (8.0 mg, 0.065 mmol) in methanol (5 mL) was stirred at room temperature for 16 hours. The reaction was concentrated and then filtered through a short plug of silica gel using 4:1 $CH_2Cl_2$:MeOH as the eluent. The appropriate fractions were concentrated, and the residue was purified by reverse phase chromatography, eluting 5% to 50% acetonitrile in water containing 0.1% trifluoroacetic acid. The product was obtained as the trifluoroacetic acid salt and was lyophilized to give COMPOUND 61 (90 mg, 51% yield) as a hygroscopic, slightly yellow solid. Purity (HPLC): >95%; Optical purity (Chiral HPLC): >93%; $^1$H NMR (400 MHz, $CD_3OD$) δ 1.01 (t, J=7.5 Hz, 3H), 1.09 (br t, J=6.9 Hz, 3H), 1.22 (br t, J=6.6 Hz, 3H), 1.70 (sextet, J=7.6 Hz, 2H), 2.44 (br s, 2H), 2.98 (br s, 2H), 3.19-3.28 (m, 5H), 3.34-3.40 (m, 3H), 3.38 (s, 3H), 3.52 (br q, J=6.6 Hz, 4H), 3.68-3.73 (m, 2H), 4.55 (s, 1H), 7.12-7.18 (m, 1H), 7.34 (d, J=8.2 Hz, 2H), 7.40-7.46 (m, 3H), 7.56 (d, J=8.2 Hz, 2H). Found: C, 50.65; H, 6.08; N, 7.02. $C_{28}H_{42}N_4O_2 \times 1.4 H_2O \times 2.6 CF_3COOH$ has C, 50.58; H, 6.06; N, 7.11%. $[\alpha]_D^{18}=-0.6$ deg [c 0.688, MeOH].

COMPOUND 62: N,N-diethyl-4-[(R)-[4-(3-methoxypropyl)-1-piperazinyl][3-(propyl-amino)phenyl]methyl]benzamide

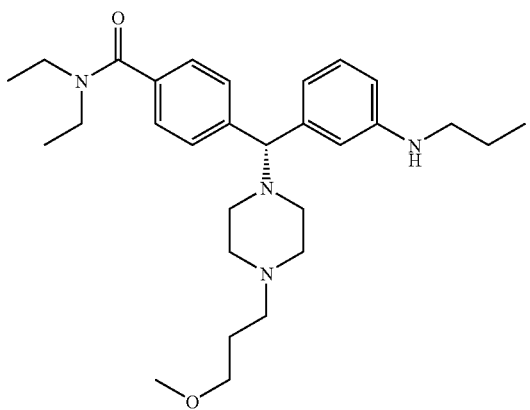

Using the same method as for COMPOUND 61 and using COMPOUND 60 (86.0 mg, 0.20 mmol), propionaldehyde (0.014 mL, 0.19 mmol) and decaborane (7.2 mg, 0.059 mmol) afforded COMPOUND 62 (89 mg, 55% yield) as its TFA salt. This material was lyophilized from $CH_3CN/H_2O$ to produce a hygroscopic, slightly yellow solid. Purity (HPLC): >97%; Optical purity (Chiral HPLC): >93%; $^1$H NMR (400 MHz, $CD_3OD$) δ 1.01 (t, J=7.4 Hz, 3H), 1.09 (br t, J=6.6 Hz, 3H), 1.22 (br t, J=6.6 Hz, 3H), 1.70 (sextet, J=7.6 Hz, 2H), 1.95-2.04 (m, 2H), 2.39 (br s, 2H), 3.01 (br s, 2H), 3.15-3.28 (m, 8H), 3.33 (s, 3H), 3.45-3.61 (m, 6H), 4.55 (s, 1H), 7.10-7.16 (m, 1H), 7.34 (d, J=8.2 Hz, 2H), 7.37-7.44 (m, 3H), 7.57 (d, J=8.0 Hz, 2H). Found: C, 53.22; H, 6.76; N, 7.48. $C_{29}H_{44}N_4O_2 \times 2.0 H_2O \times 2.0 CF_3COOH$ has C, 53.22; H, 6.77; N, 7.52%. $[\alpha]_D^{17}=-1.5$ deg [c 0.779, MeOH].

COMPOUND 63: 4-[(S)-[3-(cycloheptylamino)phenyl](piperazin-1-yl)methyl]-N,N-diethylbenzamide

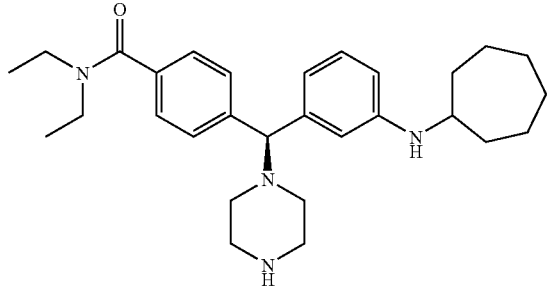

Synthesized according to the method used for COMPOUND 24 except that INTERMEDIATE 5a was used. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 63 as a colourless solid. Purity (HPLC): >99%; Optical purity (Chiral HPLC): >99%; $^1$H NMR (400 MHz, $CD_3OD$) 1.06 (t, J=6.54 Hz, 3H), 1.19 (t, J=6.64 Hz, 3H), 1.40-1.49 (m, 2H), 1.53-1.63 (m, 6H), 1.65-1.75 (m, 2H), 1.89-1.97 (m, 2H), 2.60-2.66 (m, 4H), 3.18-3.26 (m, 6H), 3.45-3.52 (m, 2H), 3.52-3.59 (m, 1H), 4.54 (s, 1H), 7.13 (dt, J=7.37, 1.68 Hz, 1H), 7.31 (d, J=8.40 Hz, 2H), 7.38-7.47 (m, 3H), 7.53 (d, J=8.20 Hz, 2H). Found: C, 52.27; H, 5.72; N, 6.94. $C_{29}H_{42}N_4O \times 0.4H_2O \times 2.9TFA$ has C, 52.21; H, 5.75; N, 7.00%. $[a]_D^{20}=+8.69$ deg [c 0.61, MeOH].

COMPOUND 64: 4-[(S)-[3-(cyclooctylamino)phenyl](piperazin-1-yl)methyl]-N,N-diethylbenzamide

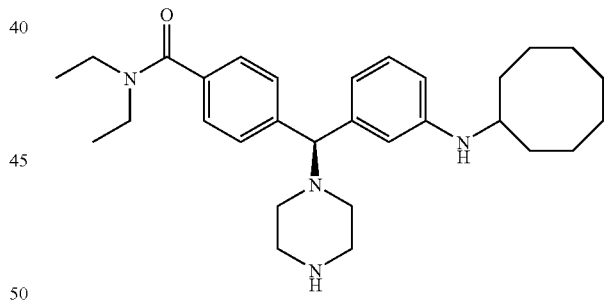

Synthesized according to the method used for COMPOUND 25 except that INTERMEDIATE 5a was used. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 64 as a colourless solid. Purity (HPLC): >99%; Optical purity (Chiral HPLC): >99%; $^1$H NMR (400 MHz, $CD_3OD$) 1.06 (t, J=6.74 Hz, 3H), 1.19 (t, J=6.69 Hz, 3H), 1.40-1.52 (m, 3H), 1.52-1.60 (m, 4H), 1.60-1.76 (m, 5H), 180-190 (m, 2H), 2.58-2.66 (m, 4H), 3.18-3.25 (m, 6H), 3.45-3.53 (m, 2H), 3.61-3.66 (m, 1H), 4.56 (s, 1H), 7.20 (ddd, J=7.81, 2.15, 0.98 Hz, 1H), 7.32 (d, J=8.47 Hz, 2H), 7.45 (t, J=7.81 Hz, 1H), 7.49 (br s, 1H), 7.51-7.55 (m, 3H). Found: C, 53.11; H, 6.01; N, 6.85. $C_{30}H_{44}N_4O \times 0.5H_2O \times 2.8TFA$ has C, 53.12; H, 5.00, N, 6.96%. $[a]_D^{20}=+8.09$ deg [c 0.45, MeOH].

COMPOUND 65: N,N-diethyl-4-[(S)-{3-[(3-phenylpropanoyl)amino]phenyl}(piperazin-1-yl)methyl]benzamide

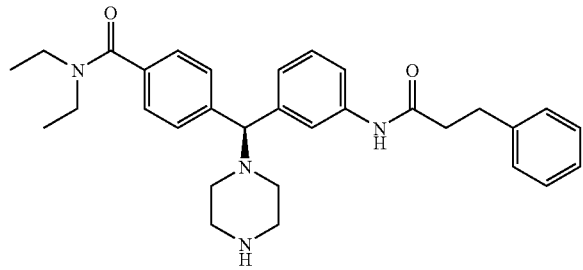

Synthesized according to the method used for COMPOUND 41 except that INTERMEDIATE 5a was used. The residue was purified by flash chromatography, eluting 25% methanol in dichloromethane, rising to 40% methanol in dichloromethane. The product was converted to the hydrochloride salt using 2M HCl in diethyl ether to give COMPOUND 65 as a colourless solid. Purity (HPLC): >99%; Optical purity (Chiral HPLC): >99%; $^1$H NMR (400 MHz, CD$_3$OD) 1.06 (t, J=6.64 Hz, 3H), 1.19 (t, J=6.88 Hz, 3H), 2.61 (t, J=7.66 Hz, 2H), 2.56-2.67 (m, 4H), 2.95 (t, J=7.66 Hz, 2H), 3.18-3.26 (m, 6H), 3.45-3.53 (m, 2H), 4.41 (s, 1H), 7.13-7.16 (m, 2H), 7.19-7.24 (m, 6H), 7.30 (d, J=8.30 Hz, 2H), 7.52 (d, J=8.20 Hz, 2H), Found: C, 61.14; H, 6.86; N, 9.10. C$_{31}$H$_{38}$N$_4$O$_2$×2.9HCl×0.3H$_2$O has C, 61.06; H, 6.86; N, 9.19%. [a]$_D^{20}$=−0.96 deg [c 0.73, MeOH].

COMPOUND 66: 4-[(R)-(3-aminophenyl)[4-(2-propenyl)-1-piperazinyl]methyl]-N,N-diethyl-benzamide

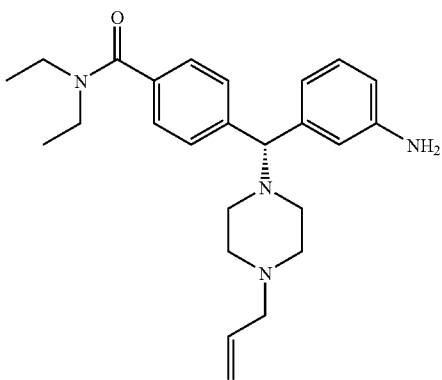

To a solution of INTERMEDIATE 4b (212 mg) in acetone (2 mL) in a microwave vial was added cesium carbonate (261 g; 1.5 eq) and alkyl bromide (55 μL, 1.2 eq). The reaction was heated to 120° C. for 5 minutes then was concentrated. The residue was dissolved in dichloromethane (20 mL) and washed with saturated aqueous sodium bicarbonate (20 mL) and water (20 mL). The organic layer was dried (MgSO$_4$), filtered and concentrated. Purification by flash chromatography, eluting 30% to 50% acetone in hexanes afforded the alkylated product as a colourless foam (191 mg, 82% yield).

The above product was dissolved in a mixture of ethanol/tetrahydrofuran/water/saturated ammonium chloride (2 mL, 4:2:1:1 ratio) and placed in a microwave vial. To the solution was added iron (26 mg, 1.1 eq) and the reaction was heated to 140° C. for 10 minutes. Reaction was filtered through celite and dichlormethane/saturated sodium bicarbonate was added. The organic layer was separated, dried (MgSO$_4$), filtered and concentrated. Purification by flash chromatography, eluting 30% to 50% acetone in hexanes afforded COMPOUND 66 as a colourless foam (101 mg, 53% yield). Purity (HPLC): >99%; Optical purity (Chiral HPLC): >99%; (400 MHz, CDCl$_3$) 1.06-1.15 (m, 3H), 1.16-1.27 (m, 3H), 2.30-2.60 (m, 6H), 3.00 (d, J=6.32 Hz, 2H), 3.19-3.32 (m, 2H), 3.48-3.57 (m, 2H), 4.11 (s, 1H), 5.11-5.20 (m, 2H), 5.85 (ddt, J=17.16 Hz, 10.25 Hz, 6.57 Hz, 1H), 6.52 (ddd, J=7.82 Hz, 2.25 Hz, 1.07 Hz, 1H), 6.72-6.75 (m, 1H), 6.78-6.82 (m, 1H), 7.05 (t, J=7.64 Hz; 1H), 7.27 (d, J=8.21 Hz, 2H), 7.43 (d, J=8.20 Hz, 2H). Found: C, 58.49; H, 7.24; N, 10.49. C$_{25}$H$_{34}$N$_4$O×3.0 HCl, 0.2 C$_4$H$_{10}$O has C, 58.38; H, 7.41; N, 10.56% [a]$_D^{20}$=+6.09 deg [c 0.852, MeOH]

COMPOUND 67: 4-[(R)-(3-aminophenyl)[4-(3-methyl-2-butenyl)-1-piperazinyl]methyl]-N,N-diethyl-benzamide

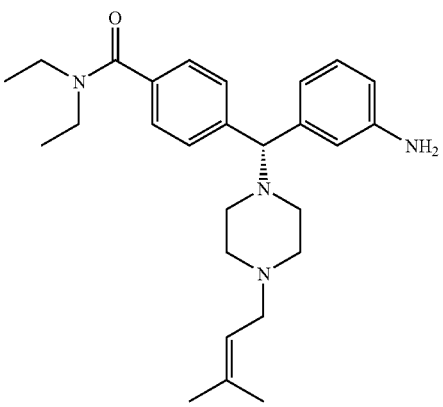

Synthesized according to the method of COMPOUND 66 except that 1-bromo-3-methyl but-2-ene was used in place of alkyl bromide. From 206 mg of INTERMEDIATE 4b was generated 95 mg of COMPOUND 67. Purity (HPLC): >99%; Optical purity (Chiral HPLC): >99%; (400 MHz, CD$_3$OD) 1.06 (m, 3H), 1.19 (m, 3H), 1.63 (s, 3H), 1.70 (s, 3H), 2.13-2.77 (m, 8H), 2.96 (d, J=7.54 Hz, 2H), 3.18-3.26 (m, 2H), 3.43-3.52 (m, 2H), 4.11 (s, 1H), 5.16-5.24 (m, 1H), 6.51 (d, J=7.67 Hz, 1H), 6.72 (d, J=7.68 Hz, 1H), 6.80 (s, 1H), 6.97 (t, J=7.67 Hz, 1H), 7.25 (d, J=8.23 Hz, 2H), 7.49 (d, J=7.68 Hz, 2H). Found: C, 56.55; H, 7.33; N, 9.59. C$_{27}$H$_{38}$N$_4$O×3.8HCl, 0.1 H$_2$O, 0.1 C$_{10}$H$_4$O has C, 56.51; H, 7.44; N, 9.62%. [a]$_D^{20}$=+5.68 deg [c 0.545, MeOH]

COMPOUND 68: 4-[(R)-(3-aminophenyl)[4-(cyclopropylmethyl)-1-piperazinyl]methyl]-N,N-diethyl-benzamide

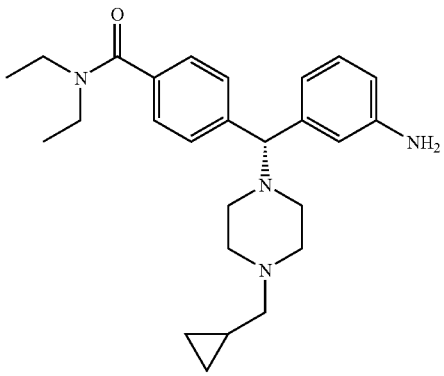

To a solution of INTERMEDIATE 4b (198 mg) in 1,2-dichloroethane was added cyclopropane carboxaldehyde (75 μL, 2 eq) and sodium triacetoxyborohydride (212 mg, 2 eq). The reaction was stirred at room temperature for 20 hours than was diluted with dichloromethane (20 mL) and washed with saturated sodium bicarbonate (10 mL). The organic layer was dried (MgSO$_4$), filtered and concentrated. The crude material was dissolved in a mixture of ethanol/tetrahydrofuran/water/saturated ammonium chloride (2 mL, 4:2:1:1 ratio) and placed in a microwave vial. To the solution was added iron and the reaction was heated to 140° C. for 10 minutes. This procedure was repeated, with the addition of fresh iron until the reaction was completed. Reaction was filtered through celite and dichlormethane/saturated sodium bicarbonate was added. The organic layer was separated, dried (MgSO$_4$), filtered and concentrated. Purification by flash chromatography, eluting 70% acetone, 5% methanol, 3% concentrated ammonium hydroxide, 22% hexanes afforded COMPOUND 68 as a colourless foam (50 mg, 24% yield over two steps). Purity (HPLC): >99%; Optical purity (Chiral HPLC): >99%; (400 MHz, CD$_3$OD) 0.07-0.13 (m, 2H), 0.46-0.53 (m, 2H), 1.06 (t, J=6.56 Hz, 3H), 1.19 (t, J=6.84 Hz, 3H), 2.24 (d, J=6.70 Hz, 2H), 2.25-2.98 (m, 8H), 3.16-3.26 (m, 2H), 3.41-3.56 (m, 2H), 4.13 (s, 1H), 6.51 (ddd, J=8.01, 2.34, 0.98 Hz, 1H), 6.72 (dt, J=7.62, 1.17 Hz, 1H), 6.80 (t, J=1.95 Hz, 1H), 6.96 (t, J=7.81 Hz, 1H), 7.26 (d, J=8.39 Hz, 2H), 7.50 (d, J=8.01 Hz, 2H). Found: C, 56.28; H, 7.33; N, 9.49. C$_{26}$H$_{36}$N$_4$O×3.8 HCl, 0.4 C$_4$H$_{10}$O has C, 56.30; H, 7.50; N, 9.52%. [a]$_D^{20}$=+5.61 deg [c 0.641, MeOH].

COMPOUND 69: N,N-diethyl 4-[(R)-[4-(2-propenyl)-1-piperazinyl][3-[(2-thienylmethyl)amino]phenyl]methyl]-benzamide

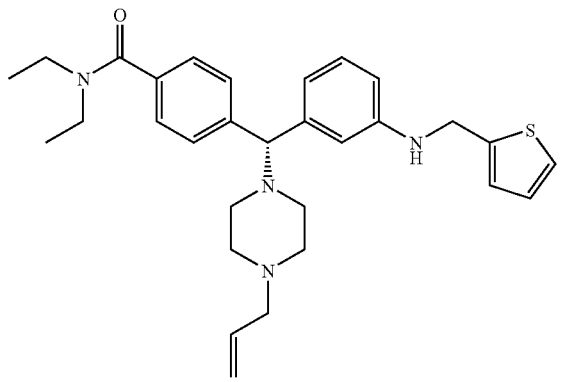

To a solution of COMPOUND 66 (80 mg) in 1,2-dichloroethane (5 mL) was added 2-thiophene carboxaldehyde (22 μL, 1.2 eq), sodium triacetoxyborohydride (83 mg, 2 eq) and two drops of acetic acid. The reaction was stirred at room temperature for 20 hours than was diluted with dichloromethane (20 mL) and washed with saturated sodium bicarbonate (10 mL). The organic layer was dried (MgSO$_4$), filtered and concentrated. The residue was purified by reverse phase chromatography, eluting 10% to 45% acetonitrile in water containing 0.1% trifluoroacetic acid. The product was obtained as the trifluoroacetic acid salt and was lyophilized to give COMPOUND 69 (59 mg, 40% yield) as a colourless solid. Purity (HPLC): >99%; Optical purity (Chiral HPLC): >99%; (400 MHz, CD$_3$OD) 1.06 (t, J=6.74 Hz, 3H), 1.19 (t, J=6.74 Hz, 3H), 3.17-3.26 (m, 2H), 3.45-3.53 (m, 2H), 3.73 (d, J=7.42 Hz, 2H), 4.32 (s, 1H), 4.53 (s, 2H), 5.54-5.61 (m, 2H), 5.89 (ddt, J=17.27, 9.82, 7.26 Hz, 1H), 6.68 (ddd, J=7.94, 2.15, 0.78 Hz, 1H), 6.81-6.86 (m, 2H), 6.91 (dd, J=5.08, 3.51 Hz, 1H), 6.94-6.99 (m, 1H), 7.09 (t, J=7.81 Hz, 1H), 7.23-7.30 (m, 3H), 7.46 (d, J=8.21 Hz, 2H). Found: C, 52.32; H, 5.51; N, 7.16. C$_{30}$H$_{38}$N$_4$OS×1.6H$_2$O, 2.3CF$_3$COOH has C, 52.35; H, 5.52; N, 7.06%. [a]$_D^{20}$=−18.03 deg [c 0.743, MeOH]

COMPOUND 70: N,N-diethyl-4-[(R)-[4-(3-methyl-2-butenyl)-1-piperazinyl][3-[(2-thienylmethyl)amino]phenyl]methyl]-benzamide

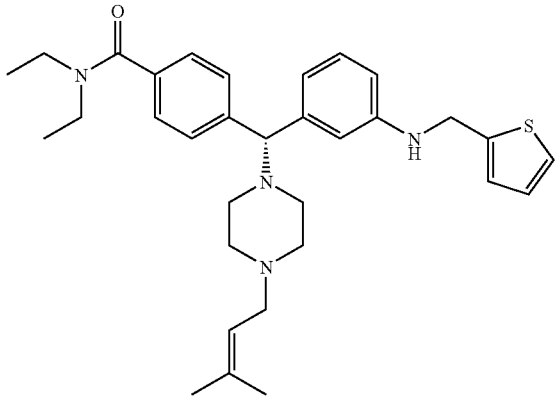

Synthesized using COMPOUND 67 and the method described for COMPOUND 69. Purity (HPLC): >99%; Optical purity (Chiral HPLC): >99%; (400 MHz, CD$_3$OD) 1.06 (t, J=6.61 Hz, 3H), 1.19 (t, J=6.61 Hz, 3H), 1.76 (s, 3H), 1.82 (s, 3H), 2.11-2.27 (m, 2H), 2.89-3.14 (m, 4H), 3.14-3.26 (m, 2H), 3.32-3.42 (m, 2H), 3.45-3.54 (m, 2H), 3.71 (d, J=7.93 Hz, 2H), 4.27 (s, 1H), 4.47 (s, 2H), 5.22-5.29 (m, 1H), 6.56 (ddd, J=7.94 Hz, 2.37 Hz, 1.02Hz, 1H), 6.68-6.71 (m, 1H), 6.77 (t, J=2.20Hz, 1H), 6.91 (dd, J=5.07 Hz, 3.38 Hz, 1H), 6.95-6.97 (m, 1H), 7.02 (t, J=7.77 Hz, 1H), 7.21 (dd, J=5.07 Hz, 1.19 Hz, 1H), 7.26 (d, J=8.05 Hz, 1H), 7.47 (d, J=8.12 Hz, 2H). Found: C, 59.49; H, 6.40; N, 7.85. C$_{32}$H$_{42}$N$_4$O×0.7H$_2$O 1.4 CF$_3$COOH has C, 59.46; H, 6.42; N, 7.97%. [a]$_D^{20}$=−20.30 deg [c 0.650, MeOH]

COMPOUND 71: 4-[(R)-[4-(cyclopropylmethyl)-1-piperazinyl][3-[(2-thienylmethyl)amino]phenyl]methyl]-N,N-diethyl-benzamide

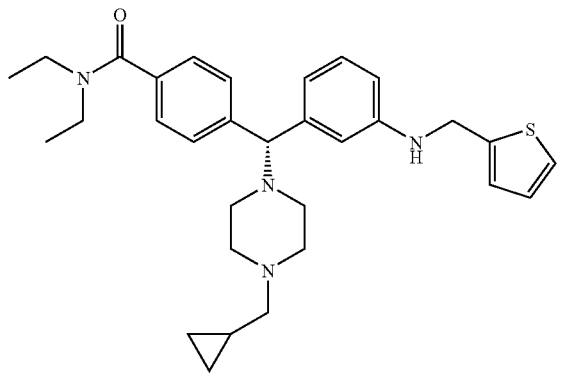

Synthesized using COMPOUND 68 and the method described for COMPOUND 69. Purity (HPLC): >99%; Optical purity (Chiral HPLC): >99%; (400 MHz, CD$_3$OD) 0.39-0.44 (m, 2H), 0.72-0.78 (m, 2H), 1.04-1.10 (m, 1H), 1.07-1.11 (m, 3H), 1.22 (t, J=6.99 Hz, 3H), 2.20-2.36 (m, 2H), 2.91-3.08 (m, 2H), 3.04 (d, J=7.49 Hz, 2H), 3.06-3.19 (m, 2H), 3.21-3.30 (m, 2H), 3.46-3.60 (m, 4H), 4.33 (s, 1H), 4.52 (s, 2H), 6.62 (dd, J=8.00, 2.44 Hz, 1H), 6.77 (d, J=7.58 Hz, 1H), 6.83 (t, J=1.81 Hz, 1H), 6.94 (dd, J=5.04, 3.53 Hz, 1H), 6.98-7.00 (m, 1H), 7.07 (t, J=7.80 Hz, 1H), 7.25 (dd, J=5.00, 122 Hz, 1H), 7.30 (d, J=8.17 Hz, 2H), 7.50 (d, J=8.16 Hz, 2H). Found. C, 53.58; H, 5.46; N, 7.10. C$_{31}$H$_{40}$N$_4$OS×0.70H$_2$O 2.4CF$_3$COOH has C, 53.55; H, 5.50; N, 6.98%. [a]$_D^{20}$=−19.74 deg [c 0.947, MeOH]

COMPOUND 72: 4-{(S)-[3-(cyclohexylamino)phenyl][4-(cyclopropylmethyl)piperazin-1-yl]methyl}-N,N-diethylbenzamide

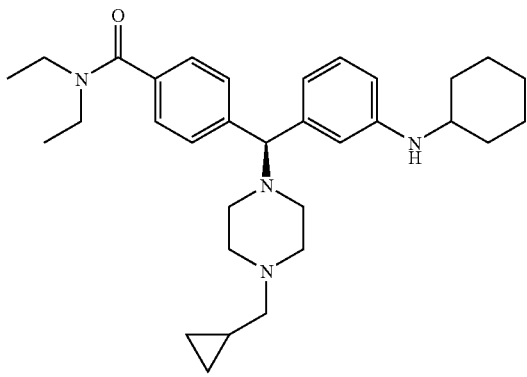

To a solution of COMPOUND 27 (250 mg; 0.56 mmol) in acetonitrile (8 mL) was added triethylamine (92.7 μL; 0.67 mmol). The solution was cooled to 0° C. than bromomethylcyclopropane (53.5 μL; 0.56 mmol) was added. Reaction mixture was stirred overnight then was concentrated under reduced pressure. The residue was dissolved in dichloromethane and washed with water. The organic layer was dried over anhydrous sodium sulphate, filtered and concentrated under reduced pressure. Column chromatography eluting with 5% methanol in dichloromethane gave COMPOUND 72 (229 g; 82% yield). Purity (HPLC-215 nm): >99%; Optical purity (Chiral HPLC-215 nm): >99%. $^1$H NMR (400 MHz, CD$_3$OD) δ 0.34-0.40 (m, 2H), 0.65-0.71 (m, 2H), 0.99-1.04 (m, 3H), 1.14 (t, J=6.83 Hz, 3H), 1.30-1.35 (m, 6H), 1.61-1.64 (m, 1H), 1.75-1.78 (m, 2H), 1.85-1.90 (m, 2H), 2.46-2.54 (br s, 1H), 2.95-3.03 (br s, 6H), 3.10-3.18 (br s, 2H), 3.37-3.44 (br s, 5H), 3.54-3.60 (br s, 2H), 7.27-2.31 (m, 3H), 7.50-7.53 (m, 3H), 7.64-7.68 (m, 2H). Found: C, 59.91; H, 8.10; N, 10.28. C$_{32}$H$_{46}$N$_4$O× 3.2HCl×1.1H$_2$O has C, 60.13; H, 8.10; N, 8.76%. [α]$_D^{16}$=+12.4 deg [c 0.51, MeOH].

COMPOUND 73: 4-[(S)-[3-(cyclohexylamino)phenyl](4-propylpiperazin-1-yl)methyl]-N,N-diethyl-benzamide

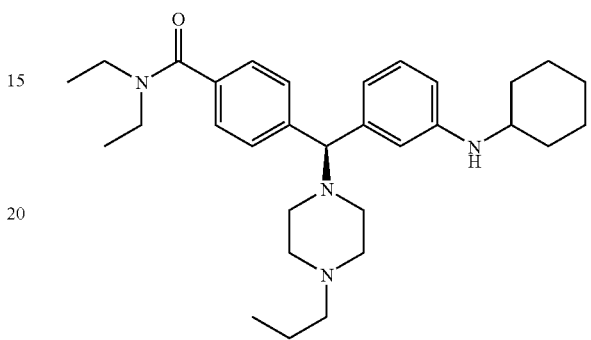

To a room temperature solution of propionaldehyde (40.6 μL 0.56 mmol) and COMPOUND 27 (250 mg; 0.56 mmol) in 1,2-dichloroethane was added sodium triacetoxy borohydride (380 mg; 1.79 mmol) and acetic acid (31.9 μL; 0.56 mmol). The reaction mixture was stirred overnight then was washed with saturated sodium bicarbonate, followed by water. The organic phase was dried over anhydrous sodium sulphate, filtered and concentrated under reduced pressure. Column chromatography eluting with 5% methanol in dichloromethane gave COMPOUND 73 (169 g; 62% yield). Purity (HPLC-215 nm): >99%; Optical purity (Chiral HPLC-215 nm): >99%. $^1$H NMR (400 MHz, CD$_3$OD) δ 0.99 (t, J=7.91 Hz, 2H), 1.10-1.16 (m, 3H), 1.28-1.33 (m, 4H), 1.61-1.65 (m, 4H), 1.75-1.79 (m, 4H), 1.83-1.90 (m, 4H), 2.97-3.01 (m, 2H), 3.13-3.15 (m, 2H), 3.17-3.28 (m, 8H), 3.42-3.46 (m, 2H), 3.52-3.54 (m, 1H), 5.08 (s, 1H) 7.24-7.29 (m, 3H), 7.48-7.51 (m, 3H), 7.55-7.57 (m, 1H), 7.62 (d, J=7.42 Hz, 1H). Found: C, 56.59; H, 7.89; N, 8.25. C$_{31}$H$_{46}$N$_4$O×4.3HCl×0.6H$_2$O has C, 56.56; H, 7.89; N, 8.51%. [α]$_D^{16}$=+14.5 deg [c 0.50, MeOH].

COMPOUND 74: 4-[(S)-[3-(cyclohexylamino)phenyl](4-ethylpiperazin-1-yl)methyl]-N,N-diethylbenzamide

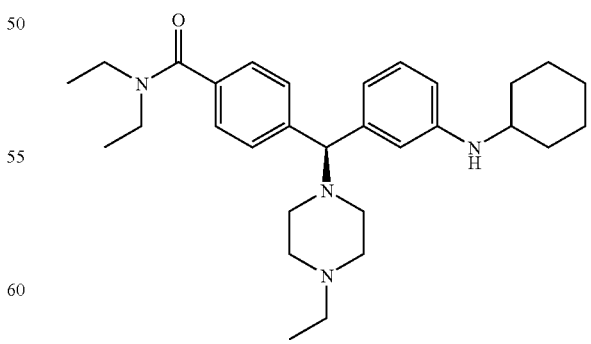

Synthesized using COMPOUND 27 (250 mg; 0.56 mmol) and the method described for COMPOUND 72. Obtained 163 g; 61% yield. Purity (HPLC-215 nm): >99%; Optical purity (Chiral HPLC-215 nm): >99%. $^1$H NMR (400 MHz, CD$_3$OD) δ 0.80 (m, 1H), 1.19 (br s, 11H), 1.59 (m, 2H), 1.88 (br s, 5H), 3.14 (br s, 11H), 3.50 (br s, 4H), 4.11 (m, 1H), 7.31 (br s, 3H), 7.67 (br s, 5H). Found: C, 53.63; H, 7.55; N, 8.05. C$_{30}$H$_{44}$N$_4$O×5.0HCl×0.7H$_2$O has C, 53.65; H, 7.56; N, 8.34%. [α]$_D^{16}$=+12.7 deg [c 0.50, MeOH].

COMPOUND 75: 4-{(S)-(4-alkylpiperazin-1-yl)[3-(cyclohexylamino)phenyl]methyl}-N,N-diethylbenzamide

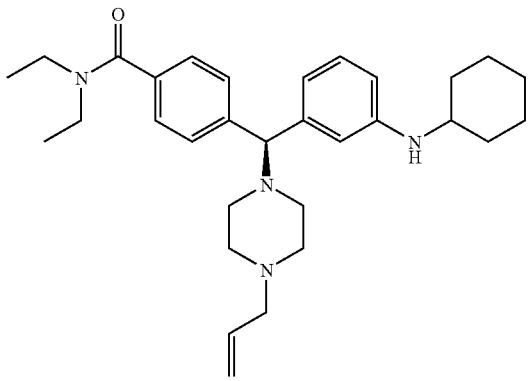

Synthesised using COMPOUND 27 (250 mg; 0.56 mmol) and the method described for COMPOUND 72. Obtained 240 g; 88% yield. Purity (HPLC-215 nm): >97%; Optical purity (Chiral HPLC-215 nm): >99%. $^1$H NMR (400 MHz, CD$_3$OD) δ 1.00 (t, J=6.44 Hz, 3H), 1.13 (t, J=7.32 Hz, 3H), 1.22-1.40 (m, 5H), 1.58-1.63 (m, 1H), 1.73-1.79 (m, 2H), 1.86-1.90 (m, 2H), 2.94-3.11 (br s, 2H), 3.12-3.19 (br s, 2H), 3.39-3.48 (br s, 7H), 3.75 (d, J=6.83 Hz, 2H), 5.49-5.53 (m, 3H), 5.54 (dd, J=11.91, 10.54 Hz, 1H), 5.87-5.91 (m, 2H), 7.27-7.33 (m, 3H), 7.49 (t, J=7.91 Hz, 1H), 7.55-7.59(m, 2H), 7.67-7.72 (m, 2H). Found: C, 56.15; H, 7.58; N, 8.34. C$_{31}$H$_{44}$N$_4$O×4.4HCl×0.8H$_2$O has C, 56.11; H, 7.60; N, 8.44%. [α]$_D^{16}$=+10.8 deg [c 0.48, MeOH].

COMPOUND 76: 4-[(S)-{3-[(cyclohexylcarbonyl)amino]phenyl}(piperazin-1-yl)methyl]-N,N-diethylbenzamide

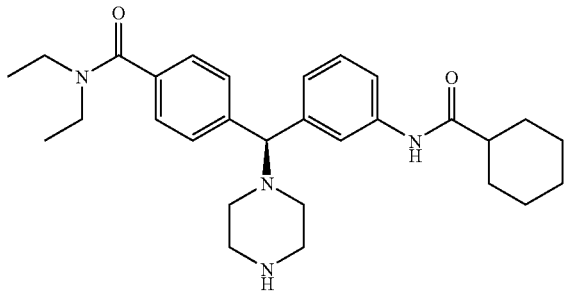

To a room temperature solution of INTERMEDIATE 5a (250 mg; 0.54 mmol) in dichloromethane (5 mL) were added triethylamine (0.15 mL; 1.08 mmol), DMAP (cat.) and cyclohexane carbonyl chloride (86 μL; 0.64 mmol). The reaction mixture was stirred for 5 hours then more triethylamine (0.08 mL; 0.58 mmol) and DMAP (cat.) were added. The reaction mixture was stirred overnight then more cyclohexane carbonyl chloride (28 μL; 0.21 mmol) was added. The reaction mixture stirred for 5 hours then was washed with two portions of saturated sodium bicarbonate. The organic phase was dried over anhydrous sodium sulphate, filtered and concentrated under reduced pressure. Column chromatography eluting with 2% methanol in dichloromethane gave the desired product.

The above product was dissolved in dichloromethane (10 mL) and TFA (1.5 mL) was added. The reaction mixture was stirred for 3 hours then was washed with one portion of saturated sodium bicarbonate followed by one portion of brine. The organic phase was dried over anhydrous sodium sulphate, filtered and concentrated under reduced pressure. Column chromatography eluting with 4.5% methanol in dichloromethane to 5% methanol in dichloromethane gave COMPOUND 76 (214 g; 83% yield for two steps). Purity (HPLC-215 nm): >99%; Optical purity (Chiral HPLC-215 nm): >99%. $^1$H NMR (400 MHz, CD$_3$OD) δ 0.98 (t, J=7.52 Hz, 3H), 1.11 (t, J=7.62 Hz, 3H), 1.16-1.34 (m, 3H), 1.37-1.42 (m, 2H), 1.58-1.64 (m, 1H), 1.70-1.78 (m, 4H), 2.18-2.31 (m, 1H), 3.10-3.17 (br s, 1H), 3.18-3.24 (m, 6H), 3.25-3.33 (br s, 3H), 3.48-3.52 (m, 5.08 (s, 1H), 7.19 (d, J=5.86 Hz, 2H), 7.26-7.31 (m, 3H), 7.57 (d, J=7.62 Hz, 2H), 7.84-7.87 (m, 1H). Found: C, 55.91; H, 6.99; N, 8.86. C$_{29}$H$_{40}$N$_4$O$_2$×4.0HCl has C, 55.95; H, 7.12; N, 9.00%. [α]$_D^{17}$=+8.3 deg [c 0.52, MeOH].

COMPOUND 77: 4-[(S)-{3-[(cyclohexylacetyl)amino]phenyl}(piperazin-1-yl)methyl]-N,N-diethylbenzamide

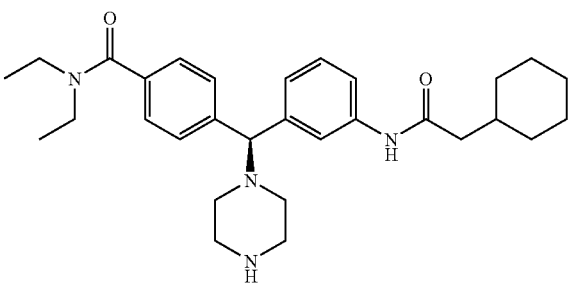

To a room temperature solution of INTERMEDIATE 5a (250 mg; 0.54 mmol) in DMF (5 mL) was added cyclohexyl acetic acid (92 mg; 0.65 mmol), DIPEA (0.38 mL; 2.16 mmol) and HATU (0.31 g; 0.81 mmol). The reaction mixture was stirred for 22 hours then was concentrated under reduced pressure. The residue was dissolved in dichloromethane, washed with sodium hydroxide (2N) then with HCl (1M). The organic phase was dried over anhydrous sodium sulphate, filtered and concentrated under reduced pressure. The residue was dissolved in dichloromethane (10 mL) and TFA (1.5 mL) was added. The reaction mixture was stirred for 4 hours then was washed with saturated sodium bicarbonate. The organic phase was dried over anhydrous sodium sulphate, filtered and concentrated under reduced pressure. Column chromatography eluting with 5% methanol in dichloromethane gave COMPOUND 77 (242 g; 92% for two steps). Purity (HPLC-215 nm): >99%; Optical purity (Chiral HPLC-215 nm): >99%. $^1$H NMR (400 MHz, CD$_3$OD) δ 0.87-0.93 (m, 2H), 0.98 (t, J=7.13 Hz, 3H), 1.08-1.14 (m, 3H), 1.20-1.23 (m, 2H), 1.52-1.71 (br s, 6H), 1.72-1.77 (m, 1H), 2.12 (d, J=7.03 Hz, 2H), 3.09-3.14 (m, 2H), 3.18-3.23 (m, 6H), 3.26-3.33 (br s, 3H), 3.48-3.52 (m, 1H), 5.08 (s, 1H), 7.20 (d, J=4.49 Hz, 2H), 7.24-7.31 (m, 3H), 7.57 (d, J=7.81 Hz, 2H), 7.83 (s, 1H). Found: C, 58.11;

H, 8.99; N, 7.46. $C_{30}H_{42}N_4O_2 \times 0.4HCl \times 6.5H_2O$ has C, 57.90; H, 8.97; N, 9.00%. $[\alpha]_D^{17}=+4.6$ deg [c 0.46, MeOH].

COMPOUND 78: 4-[(S)-{3-[cyclohexyl(methyl)amino]phenyl}(piperazin-1-yl)methyl]-N,N-diethylbenzamide

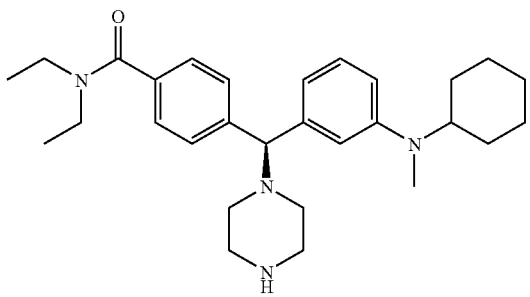

To a room temperature solution of INTERMEDIATE 5a (300 mg; 0.64 mmol) in 1,2-dichloroethane (15 mL) were added cyclohexanone (0.20 mL; 1.93 mmol), sodium triacetoxy borohydride (0.43 g; 2.05 mmol) and acetic acid (37 μL; 0.64 mmol). The reaction mixture was stirred for 6 hours then was washed with two portions of saturated sodium bicarbonate. The organic phase was dried over anhydrous sodium sulphate, filtered and concentrated under reduced pressure. Column chromatography eluting with 4% methanol in dichloromethane gave the desired product.

To a room temperature solution of the above product (320 mg; 0.58 mmol) in methanol (6 mL) was added formaldehyde (37% in $H_2O$) (130 μL; 1.74 mmol). The reaction mixture was stirred for 30 minutes then decaborane (43 mg; 0.35 mmol) was added. The reaction mixture was stirred for 18 hours then was concentrated under reduced pressure. The residue was dissolved in dichloromethane then was washed with saturated sodium bicarbonate. The organic phase was dried over anhydrous sodium sulphate, filtered and concentrated under reduced pressure to give 296 mg of crude material. The crude material was dissolved in dichloromethane (10 mL) and TFA (1.5 mL) was added. The reaction mixture was stirred for 2.5 hours then saturated sodium bicarbonate was added. The organic phase was dried over anhydrous sodium sulphate, filtered and concentrated under reduced pressure. Column chromatography eluting with 5% methanol and 1% $NH_4OH$ in dichloromethane gave COMPOUND 78 (211 g; 78% for two steps). Purity (HPLC-21.5 nm): >99%; Optical purity (Chiral HPLC-215 nm): >99%. $^1$H NMR (400 MHz, $CD_3OD$) δ 0.98 (t, J=7.13 Hz, 3H), 1.11 (t, J=7.52 Hz, 3H), 1.21-1.32 (br s, 5H), 1.51-1.58 (m, 3H), 1.71-1.86 (br s, 2H), 3.11-3.18 (m, 5H), 3.22-3.33 (br s, 3H), 3.41-3.45 (m, 3H), 3.47-3.55 (br s, 2H), 4.48 (s, 3H), 5.08 (s, 1H), 7.27 (d, J=8.40 Hz, 3H), 7.49-7.52 (m, 3H), 7.56-7.67 (br s, 1H), 7.77-7.88 (br s, 1H). Found: C, 54.78; H, 7.71; N, 8.57. $C_{29}H_{42}N_4O \times 4.1HCl \times 1.3H_2O$ has C, 54.80; H, 7.72; N, 8.81%. $[\alpha]_D^{17}=+17.9$ deg [c 0.52, MeOH].

COMPOUND 79: 4-t[R)-{3-[cyclohexyl(methyl)amino]phenyl}(piperazin-1-yl)methyl]-N,N-diethylbenzamide

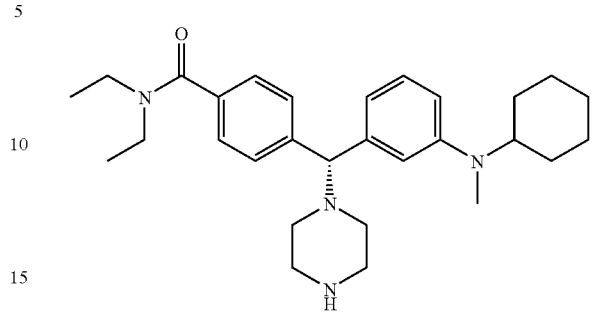

Synthesised using INTERMEDIATE 5b (250 mg; 0.54 mmol) and the method described for COMPOUND 78. Obtained 189 g; 79% yield for two steps. Purity (HPLC-215 nm): >99%; Optical purity (Chiral HPLC-215 nm): >99%. $^1$H NMR (400 MHz, $CD_3OD$) δ 0.98 (t, J=7.13 Hz, 3H), 1.11 (t, J=7.52 Hz, 3H), 1.21-1.32 (br s, 5H), 1.51-1.58 (m, 3H), 1.71-1.86 (br s, 2H), 3.11-3.18 (m, 5H), 3.22-3.33 (br s, 3H), 3.41-3.45 (m, 3H), 3.47-3.55 (br s, 2H), 4.48 (s, 3H), 5.08 (s, 1H), 7.27 (d, J=8.40 Hz, 3H), 7.49-7.52 (m, 3H), 7.56-7.67 (br s, 1H), 7.77-7.88 (br s, 1H). Found: C, 53.87; H, 7.45; N, 8.39. $C_{29}H_{42}N_4O \times 4.8HCl \times 0.5H_2O$ has C, 53.86; H, 7.45; N, 8.66%. $[\alpha]_D^{16}=-16.3$ deg [c 0.51, MeOH].

What is claimed is:

1. A compound of formula I, or a pharmaceutically acceptable salt thereof:

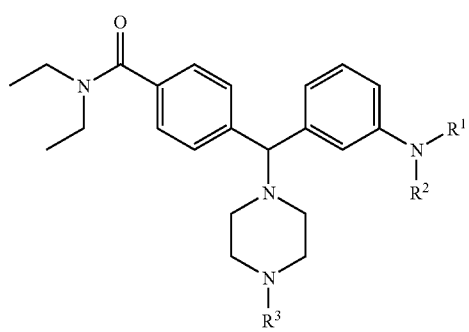

wherein $R^1$ is selected from $C_{3-6}$alkyl, $C_{6-10}$aryl, $C_{2-9}$heteroaryl, $C_{6-10}$aryl-$C_{1-4}$alkyl, $C_{2-9}$heteroaryl-$C_{1-4}$alkyl, $C_{3-10}$cycloalkyl, $C_{3-10}$cycloalkyl-$C_{1-4}$alkyl, $R^8$—C(=O)—, $R^8$—S(=O)$_2$—, $R^8$—S(=O)—, $R^8$—NHC(=O)—, $R^8$—C(=S)— and $R^8$—NH—C(=S)—, wherein $R^8$ is selected from $C_{3-6}$alkyl, $C_{6-10}$aryl, $C_{2-9}$heteroaryl, $C_{6-10}$aryl-$C_{1-4}$alkyl, $C_{2-9}$heteroaryl-$C_{1-4}$alkyl, $C_{3-10}$cycloalkyl, and $C_{3-10}$cycloalkyl-$C_{1-4}$alkyl, wherein said $C_{3-6}$alkyl, $C_{6-10}$aryl, $C_{2-9}$heteroarly, $C_{6-10}$aryl-$C_{1-4}$alkyl, $C_{2-9}$heteroarly-$C_{1-4}$alkyl, $C_{3-10}$cycloalkyl, and $C_{3-10}$cycloalkyl-$C_{1-4}$alkyl used in defining $R^1$ and $R^8$ are optionally substituted with one or more groups selected from —R, —$NO_2$, —OR, —Cl, —Br, —I, —F, —$CF_3$, —C(=O)R, —C(=O)OH, —$NH_2$, —SH, —NHR, —NR₂, —SR, —SO₃H, —SO₂R, —S(=O)R, —CN, —OH, —C(=O)OR, —C(=O)NR₂, —NRC(=O)R, and —NRC(=O)—OR, wherein R is, independently, selected from —H, $C_{1-6}$alkyl and phenyl;

$R^2$ is selected from —H and $C_{1-6}$alkyl optionally substituted with one or more groups selected from —CF₃, —OH, $C_{1-3}$alkoxy, and halogen; and $R^3$ is selected from —H, $C_{1-6}$alkyl-O—C(=O)—, $C_{1-6}$alkyl, $C_{3-6}$cycloalkyl, and $C_{3-6}$cycloalkyl-$C_{1-4}$ alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$ alkyl are optionally substituted with one or more groups selected from $C_{1-6}$alkyl, halogenated $C_{1-6}$alkyl, —NO₂, —CF₃, $C_{1-6}$alkoxy and halogen.

2. A compound according to claim 1, wherein $R^1$ is selected from $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, $C_{3-10}$cycloalkyl-$C_{1-4}$alkyl, wherein said $C_{3-6}$alkyl, $C_{6-10}$aryl, $C_{2-6}$heteroaryl, $C_{6-10}$aryl-$C_{1-4}$ alkyl, $C_{2-6}$heteroaryl-$C_{1-4}$alkyl, $C_{3-10}$cycloalkyl, $C_{3-10}$cycloalkyl-$C_{1-4}$alkyl are optionally substituted with one or more groups selected from $C_{1-4}$alkyl, —CF₃, —OH, $C_{1-3}$alkoxy, phenoxy, and halogen;

$R^2$ is selected from —H and $C_{1-3}$alkyl; and $R^3$ is selected from —H and $C_{1-6}$alkyl-O—C(=O)—.

3. A compound according to claim 2, wherein $R^1$ is $R^9$—CH₂—, wherein $R^9$ is selected from phenyl, pyridyl, thienyl, furyl, imidazolyl, triazolyl, pyrrolyl, thiazolyl, N-oxido-pyridyl, benzyl, pyridylmethyl, thienylmethyl, furylmethyl, imidazolylmethyl, triazolylmethyl, pyrrolylmethyl, thiazolylmethyl and N-oxido-pyridylmethyl, optionally substituted with one or more groups selected from $C_{1-4}$alkyl, —CF₃, —OH, $C_{1-3}$alkoxy, phenoxy and halogen; and $R^2$ and $R^3$ are hydrogen.

4. A compound according to claim 3, wherein $R^9$ is selected from benzyl, phenyl, pyridyl, thienyl, furyl, imidazolyl, pyrrolyl and thiazolyl, optionally substituted with one or more groups selected from $C_{1-4}$alkyl, —CF₃, —OH, $C_{1-3}$alkoxy, phenoxy, and halogen.

5. A compound according to claim 4, wherein $R^9$ is selected from benzyl, phenyl, pyridyl, thienyl, furyl, imidazolyl, pyrrolyl and thiazolyl.

6. A compound according to claim 1, wherein $R^1$ is selected from $C_{3-6}$alkyl, $C_{3-10}$cycloalkyl, and $C_{3-10}$cycloalkyl-$C_{1-4}$alkyl, wherein said $C_{3-6}$alkyl, $C_{3-10}$cycloalkyl, and $C_{3-10}$cycloalkyl-$C_{1-4}$alkyl are optionally substituted with one or more groups selected from $C_{1-4}$alkyl, —CF₃, —OH, $C_{1-3}$alkoxy, phenoxy, and halogen;

$R^2$ is —H or $C_{1-3}$alkyl; and $R^3$ is —H, $C_{1-6}$alkyl, $C_{3-6}$cycloalkyl, and $C_{3-6}$cycloalkyl-$C_{1-4}$alkyl, wherein said $C_{1-6}$alkyl, $C_{3-6}$cycloalkyl, $C_{3-6}$cycloalkyl-$C_{1-4}$alkyl are optionally substituted with one or more groups selected from $C_{1-4}$alkyl, halogen, —CF₃, —OH, $C_{1-3}$alkoxy, phenoxy, and halogen.

7. A compound of formula I, or a pharmaceutically acceptable salt thereof:

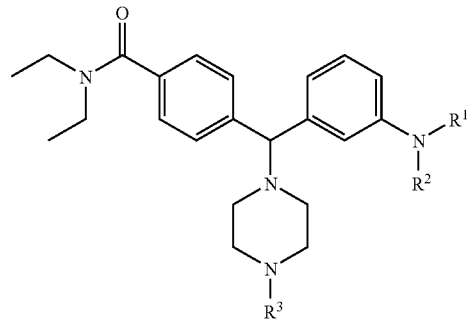

wherein $R^1$ is selected from 1-propyl, 2-propyl, 1-butyl, 2-butyl, t-butyl, 2-methyl-1-propyl, cyclopentyl, cyclohexyl, cycloheptyl, cyclooctyl, and cyclononyl;

$R^2$ is selected from —H, methyl, ethyl, 1-propyl and 2-propyl; and $R^3$ is selected from —H, methyl, ethyl, allyl, 3,3-dimethyl-allyl, cyclopropylmethyl, 2-methoxy-ethyl, and 3-methoxy-1-propyl.

8. A compound according to claim 1, wherein $R^1$ is selected from $R^8$—C(=O)—, $R^8$—S(=O)₂—, $R^8$—S(=O)—, $R^8$—NHC(=O)—, $R^8$—C(=S)— and $R^8$—NH—C(=S)—, wherein $R^8$ is selected from $C_{3-6}$alkyl, $C_{6-10}$aryl, $C_{2-6}$heteroaryl; $C_{6-10}$aryl-$C_{1-4}$ alkyl, $C_{2-6}$heteroaryl-$C_{1-4}$alkyl, $C_{3-10}$cycloalkyl, a $C_{3-10}$cycloalkyl-$C_{1-4}$alkyl; wherein said $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-6}$cycloalkyl-$C_{1-4}$alkyl are optionally substituted with $C_{1-4}$alkyl, —CF₃, —OH, $C_{1-3}$alkoxy, phenoxy, and halogen;

$R^2$ is —H; and $R^3$ is selected from —H and $C_{1-6}$alkyl-O—C(=O)—.

9. A compound according to claim 8, wherein $R^8$ is selected from phenyl, benzyl, phenethyl and cyclohexyl, wherein said phenyl, benzyl, phenethyl and cyclohexyl are optionally substituted with one or more groups selected from methyl, methoxy and halogen.

10. A compound according to claim 1, wherein the compound is selected from:

N,N-diethyl-4-((S)piperazin-1-yl{3-[(1,3-thiazol-2-ylmethyl)amino]phenyl}methyl)benzamide;

N,N-diethyl-4-((R)-piperazin-1-yl{3-[(1,3-thiazol-2-ylmethyl)amino]phenyl}methyl)benzamide;

4-[(S)-[3-(benzylamino)phenyl](piperazin-1-yl)methyl]-N,N-diethylbenzamide;

N,N-diethyl-4-((R)-piperazin-1-yl{3-[(thien-2-ylmethyl)amino]phenyl}methyl)benzamide;

N,N-diethyl-4-((S)-piperazin-1-yl{3-[(thien-2-ylmethyl)amino]phenyl}methyl)benzamide;

N,N-diethyl-4-[(S)-{3-[(2-furylmethyl)amino]phenyl}(piperazin-1-yl)methyl]benzamide;

4-[(R)-[3-(benzylamino)phenyl](piperazin-1-yl)methyl]-N,N-diethylbenzamide;

N,N-diethyl-4-[(R)-{3-[(2-furylmethyl)amino]phenyl}(piperazin-1-yl)methyl]benzamide;

N,N-diethyl-4-((R)-piperazin-1-yl{3-[(thien-3-ylmethyl)amino]phenyl}methyl)benzamide;

N,N-diethyl-4-((S)-piperazin-1-yl{3-[(thien-3-ylmethyl)amino]phenyl}methyl)benzamide;

N,N-diethyl-4-[(R)-{3-[(3-furylmethyl)amino]phenyl}(piperazin-1-yl)methyl]benzamide;
N,N-diethyl-4-[(R)-{3-[(2-phenylethyl)amino]phenyl}(piperazin-1-yl)methyl]benzamide;
4-[(R)-{3-[(cyclohexylmethyl)amino]phenyl}(piperazin-1-yl)methyl]-N,N-diethylbenzamide;
N,N-diethyl-4-[(R)-piperazin-1-yl(3-{[4-trifluoromethyl)benzyl]amino}phenyl)methyl]benzamide;
4-[(R)-{3-[(cyclopentylmethyl)amino]phenyl}(piperazin-1-yl)methyl]-N,N-diethylbenzamide;
4-[(S)-{3-[(cyclohexylmethyl)amino]phenyl}(piperazin-1-yl)methyl]-N,N-diethylbenzamide;
4-[(R)-{3-[(cyclohex-1-en-1-ylmethyl)amino]phenyl}(piperazin-1-yl)methyl]-N,N-diethylbenzamide;
N,N-diethyl-4-[(S)-{3-[methyl(phenyl)amino]phenyl}(piperazin-1-yl)methyl]benzamide;
N,N-diethyl-4-[(S)-{3-[ethyl(phenyl)amino]phenyl}(piperazin-1-yl)methyl]benzamide;
N,N-diethyl-4-[(R)-{3-[methyl(phenyl)amino]phenyl}(piperazin-1-yl)methyl]benzamide;
N,N-diethyl-4-[(R)-{3-[ethyl(phenyl)amino]phenyl}(piperazin-1-yl)methyl]benzamide;
4-[(R)-{3-[(cyclohexylmethyl)amino]phenyl}(piperazin-1-yl)methyl]-N,N-diethylbenzamide;
4-[(R)-[3-(cyclopentylamino)phenyl](piperazin-1-yl)methyl]-N,N-diethylbenzamide;
4-[(R)-[3-(cycloheptylamino)phenyl](piperazin-1-yl)methyl]-N,N-diethylbenzamide;
4-[(R)-[3-(cyclooctylamino)phenyl](piperazin-1-yl)methyl]-N,N-diethylbenzamide;
4-[(R)-[3-(cyclononylamino)phenyl](piperazin-1-yl)methyl]-N,N-diethylbenzamide;
4-[(S)-[3-(cyclohexylamino)phenyl](piperazin-1-yl)methyl]-N,N-diethylbenzamide;
N,N-diethyl-4-[(R)-{3-[(4-methylphenyl)amino]phenyl}(piperazin-1-yl)methyl]benzamide;
N,N-diethyl-4-[(S)-{3-[(4-methylphenyl)amino]phenyl}(piperazin-1-yl)methyl]benzamide;
4-[(R)-{3-[(3-chlorophenyl)amino]phenyl}(piperazin-1-yl)methyl]-N,N-diethylbenzamide;
4-[(S)-{3-[(3-chlorophenyl)amino]phenyl}(piperazin-1-yl)methyl]-N,N-diethylbenzamide;
4-[(R)-{3-[(2-fluorophenyl)amino]phenyl}(piperazin-1-yl)methyl]-N,N-diethylbenzamide;
4-[(S)-{3-[(2-fluorophenyl)amino]phenyl}(piperazin-1-yl)methyl]-N,N-diethylbenzamide;
4-[(R)-[3-(benzoylamino)phenyl](piperazin-1-yl)methyl]-N,N-diethylbenzamide;
N,N-diethyl-4-[(R)-{3-[(phenylacetyl)amino]phenyl}(piperazin-1-yl)methyl]benzamide;
4-[(S)-[3-(benzoylamino)phenyl](piperazin-1-yl)methyl]-N,N-diethylbenzamide;
N,N-diethyl-4-[(S)-{3-[(phenylacetyl)amino]phenyl}(piperazin-1-yl)methyl]benzamide;
N,N-diethyl-4-[(R)-{3-[(2-methyl-2-phenylpropanoyl)amino]phenyl}(piperazin-1-yl)methyl]benzamide;
N,N-diethyl-4-[(R)-(3-{[(3-fluorophenyl)acetyl]amino}phenyl)(piperazin-1-yl)methyl]benzamide;
4-[(R)-{3-[(cyclohexylacetyl)amino]phenyl}(piperazin-1-yl)methyl]-N,N-diethylbenzamide;
N,N-diethyl-4-[(R)-{3-[(3-phenylpropanoyl)amino]phenyl}(piperazin-1-yl)methyl]benzamide;
4-[(R)-{3-[(cyclohexylcarbonyl)amino]phenyl}(piperazin-1-yl)methyl]-N,N-diethylbenzamide;
N,N-diethyl-4-[(R)-{3-[(phenylsulfonyl)amino]phenyl}(piperazin-1-yl)methyl]benzamide;
4-[(R)-{3-[(benzylsulfonyl)amino]phenyl}(piperazin-1-yl)methyl]-N,N-diethylbenzamide;
N,N-diethyl-4-[(S)-{3-[(phenylsulfonyl)amino]phenyl}(piperazin-1-yl)methyl]benzamide;
4-[(R)-{3-[(anilinocarbonyl)amino]phenyl}(piperazin-1-yl)methyl]-N,N-diethylbenzamide;
4-[(R)-{3-[(anilinocarbonothioyl)amino]phenyl}(piperazin-1-yl)methyl]-N,N-diethylbenzamide;
N,N-diethyl-4-[(S)-1-piperazinyl[3-(propylamino)phenyl]methyl]benzamide;
4-[(S)-[3-(dipropylamino)phenyl]-1-piperazinylmethyl]-N,N-diethylbenzamide;
N,N-diethyl-4-[(R)-1-piperazinyl[3-(propylamino)phenyl]methyl]benz-amide;
4-[(R)-[3-(dipropylamino)phenyl]-1-piperazinylmethyl]-N,N-diethylbenzamide;
N,N-diethyl-4-[(S)-1-piperazinyl[3-[[[4-(3-pyridinyl)phenyl]methyl]-amino]phenyl]methyl]benzamide;
N,N-diethyl-4-[(S)-[3-[[[4-(1H-imidazol-1-yl)phenyl]methyl]amino]-phenyl]-1-piperazinylmethyl]benza-mide;
N,N-diethyl-4-[(S)-1-piperazinyl[3-[(2-quinolinylmethyl)amino]phenyl]-methyl]benzamide;
4-[(R)-[3-[(2,2-diphenylethyl)amino]phenyl]-1-piperazinylmethyl]-N,N-diethylbenzamide;
4-[(R)-[3-[[[4-(1,1-dimethylethyl)phenyl]methyl]amino]phenyl]-1-piperazinylmethyl]-N,N-diethylbenzamide;
N,N-diethyl-4-[(R)-[3-[[(4-phenoxyphenyl)methyl]amino]phenyl]-1-piperazinylmethyl]benzamide;
N,N-diethyl-4-[(R)-[4-(2-propenyl)-1-piperazinyl][3-(propylamino)-phenyl]methyl]benzamide;
N,N-diethyl-4-[(R)-[4-(2-methoxyethyl)-1-piperazinyl][3-(propylamino)-phenyl]methyl]benzamide;
N,N-diethyl-4-[(R)-[4-(3-methoxypropyl)-1-piperazinyl][3-(propyl-amino)phenyl]methyl]benzamide;
4-[(S)-[3-(cycloheptylamino)phenyl](piperazin-1-yl)methyl]-N,N-diethylbenzamide;
4-[(S)-[3-(cyclooctylamino)phenyl](piperazin-1-yl)methyl]-N,N-diethylbenzamide;
N,N-diethyl-4-[(S)-{3-[(3-phenylpropanoyl)amino]phenyl}(piperazin-1-yl)methyl]benzamide;
4-[(R)-(3-aminophenyl)[4-(2-propenyl)-1-piperazinyl]methyl]-N,N-diethyl-benzamide;
4-[(R)-(3-aminophenyl)[4-(3-methyl-2-butenyl)-1-piperazinyl]methyl]-N,N-diethyl-benzamide;
4-[(R)-(3-aminophenyl)[4-(cyclopropylmethyl)-1-piperazinyl]methyl]-N,N-diethyl-benzamide;
N,N-diethyl-4-[(R)-[4-(2-propenyl)-1-piperazinyl][3-[(2-thienylmethyl)amino]phenyl]methyl]-benzamide;
N,N-diethyl-4-[(R)-[4-(3-methyl-2-butenyl)-1-piperazinyl][3-[(2-thienylmethyl)amino]phenyl]methyl]-benzamide;
4-[(R)-[4-(cyclopropylmethyl)-1-piperazinyl][3-[(2-thienylmethyl)amino]phenyl]methyl]-N,N-diethyl-benzamide;
4-{(S)-[3-(cyclohexylamino)phenyl][4-(cyclopropylmethyl)piperazin-1-yl]methyl}-N,N-diethylbenzamide;
4-[(S)-[3-(cyclohexylamino)phenyl](4-propylpiperazin-1-yl)methyl]-N,N-diethylbenzamide;
4-[(S)-[3-(cyclohexylamino)phenyl](4-ethylpiperazin-1-yl)methyl]-N,N-diethylbenzamide;
4-{(S)-(4-alkylpiperazin-1-yl)[3-(cyclohexylamino)phenyl]methyl}-N,N-diethylbenzamide;
4-[(S)-{3-[(cyclohexylcarbonyl)amino]phenyl}(piperazin-1-yl)methyl]-N,N-diethylbenzamide;
4-[(S)-{3-[(cyclohexylacetyl)amino]phenyl}(piperazin-1-yl)methyl]-N,N-diethylbenzamide;

4-[(S)-{3-[cyclohexyl(methyl)amino]phenyl}(piperazin-1-yl)methyl]-N,N-diethylbenzamide;

4-[(R)-{3-[cyclohexyl(methyl)amino]phenyl}(piperazin-1-yl)methyl]-N,N-diethylbenzamide; enantiomers thereof; and pharmaceutically acceptable salts thereof.

11. A pharmaceutical composition comprising a compound according to claim 1 and a pharmaceutically acceptable carrier.

12. A method for the therapy of pain in a warm-blooded animal, comprising the step of administering to said animal in need of such therapy a therapeutically effective amount of a compound according to claim 1.

13. A process for preparing a compound of formula II, comprising:

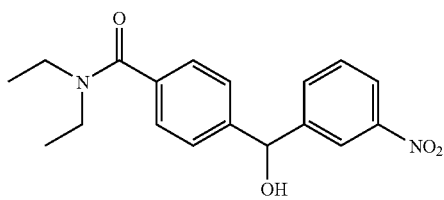

II a) reacting a compound of formula III:

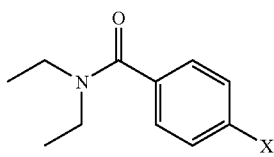

III with a compound of formula IV

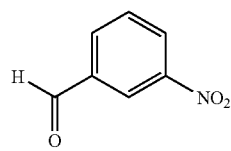

IV in the presence of a base having a pKa of more than 15 wherein X is a halogen.

14. A process for preparing a compound of formula VI:

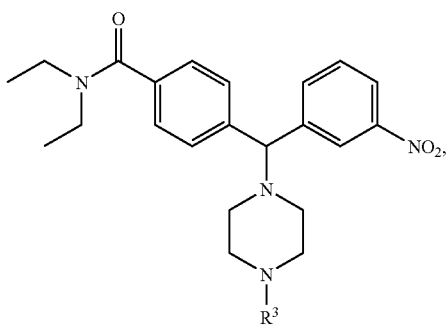

VI comprising: reacting a compound of formula II

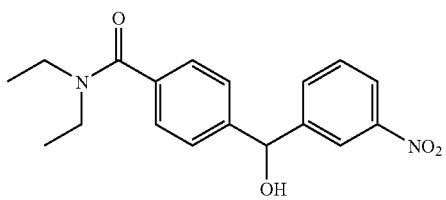

II with a compound of formula VII

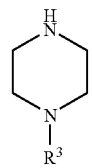

VII in the presence of $SOX_2$ to form the compound of formula VI, wherein $R^3$ is selected from —H, $C_{1-6}$alkyl-O—C(=O)—, $C_{1-6}$alkyl, $C_{3-6}$cycloalkyl, and $C_{3-6}$cycloalkyl-$C_{1-4}$ alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$ alkyl are optionally substituted with one or more groups selected from $C_{1-6}$alkyl, halogenated $C_{1-6}$alkyl, —$NO_2$, —$CF_3$, $C_{1-6}$alkoxy and halogen; and X is halogen.

15. A process for preparing a compound of formula I,

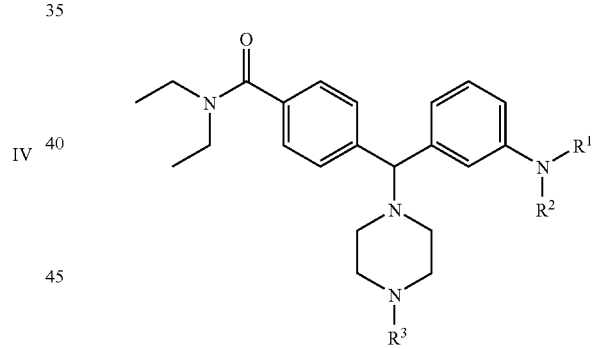

I comprising: reacting a compound of formula VIII,

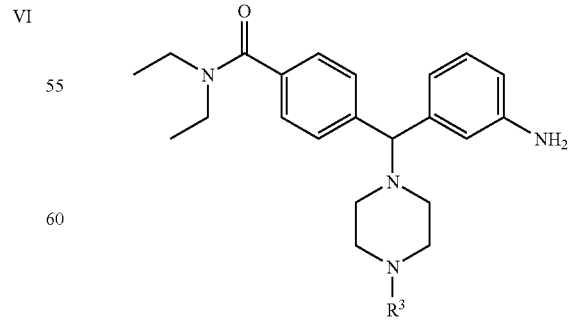

VIII with $R^9$—CHO in the presence of a reducing agent to form the compound of formula I: wherein $R^1$ is $R^9$—$CH_2$—, wherein $R^9$ is selected from phenyl, pyridyl, thienyl, furyl, imidazolyl, triazolyl, pyrrolyl, thiazolyl, N-oxido-pyridyl, benzyl, pyridylmethyl, thienylmethyl, furylmethyl, imidazolylmethyl, triazolylmethyl, pyrrolylmethyl, thiazolylmethyl and N-oxido-pyridylmethyl, optionally substituted with one or more groups selected from $C_{1-4}$alkyl, —$CF_3$, —OH, $C_{1-3}$alkoxy, phenoxy and halogen;

$R^2$ is —H; and $R^3$ is selected from $C_{1-6}$alkyl-O—C(=O)—, $C_{1-6}$alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —$NO_2$, —$CF_3$, $C_{1-6}$alkoxy and halogen.

16. A process for preparing a compound of formula IX,

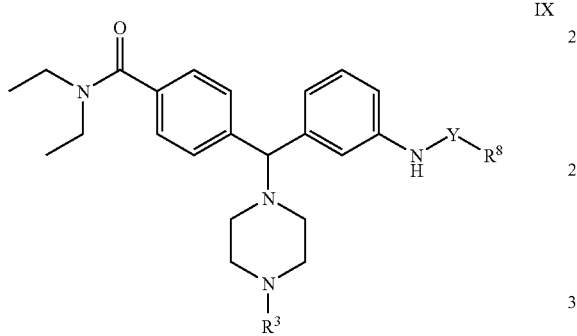

IX comprising: reacting a compound of formula VIII,

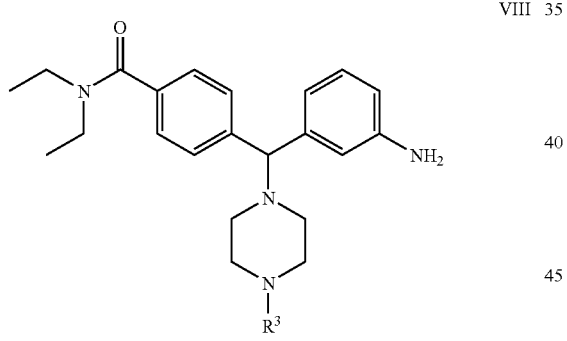

VIII with $R^8$—Y—X or $R^8$—Y—O—Y—$R^8$ to form the compound of formula IX: wherein X is halogen;

Y is selected from —C(=O)— and —S(=O)$_2$—;

$R^8$ is selected from $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl; wherein said $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl are optionally substituted with $C_{1-4}$alkyl, —$CF_3$, —OH, $C_{1-3}$alkoxy, phenoxy, and halogen; and $R^3$ is selected from $C_{1-6}$alkyl-O—C(=O)—, $C_{1-6}$alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —$NO_2$, —$CF_3$, $C_{1-6}$alkoxy and halogen.

17. A process for preparing a compound of formula IX,

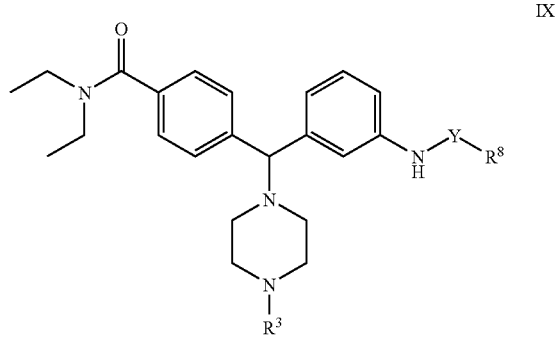

IX comprising: reacting a compound of formula VIII,

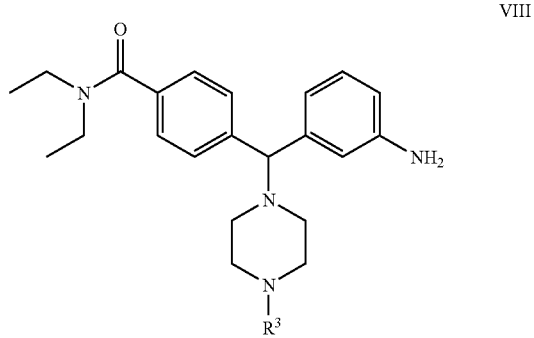

VIII with $R^8$-Z to form the compound of formula IX: wherein

Z is selected from —NCO and —NCS;

Y is selected from —C(=O)NH— and —C(=S)NH—;

$R^8$ is selected from $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl; wherein said $C_{3-6}$alkyl, $C_{6-10}$aryl, $C_{2-6}$heteroaryl, $C_{6-10}$aryl-$C_{1-4}$alkyl, $C_{2-6}$heteroaryl-$C_{1-4}$alkyl, $C_{3-10}$cycloalkyl, and $C_{3-10}$cycloalkyl-$C_{1-4}$alkyl are optionally substituted with $C_{1-4}$alkyl, —$CF_3$, —OH, $C_{1-3}$alkoxy, phenoxy, and halogen; and $R^3$ is selected from $C_{1-6}$alkyl-O—C(=O)—, $C_{1-6}$alkyl, $C_{3-6}$cycloalkyl, and $C_{3-6}$cycloalkyl-$C_{1-4}$alkyl, wherein said $C_{1-6}$alkyl-O—C(=O)—, $C_{1-6}$alkyl, $C_{3-6}$cycloalkyl, and $C_{3-6}$cycloalkyl-$C_{1-4}$alkyl are optionally substituted with one or more groups selected from $C_{1-6}$alkyl, halogenated $C_{1-6}$alkyl, —$NO_2$, —$CF_3$, $C_{1-6}$alkoxy and halogen.

* * * * *